US012698483B2

(12) United States Patent
Siller et al.

(10) Patent No.: US 12,698,483 B2
(45) Date of Patent: Aug. 4, 2026

(54) METHOD FOR BIOTRANSFORMATION OF TRICHOTHECENES

(71) Applicant: DSM Austria GmbH, Getzersdorf (AT)

(72) Inventors: Martin Siller, Vienna (AT); Gerhard Adam, Vienna (AT); Maria Doppler, Vienna (AT); Rainer Schuhmacher, Vienna (AT); Karl Kugler, Neuherberg (DE); Klaus F.X. Mayer, Neuherberg (DE); Gerlinde Wiesenberger, Vienna (AT); Herbert Michlmayr, Vienna (AT); Wolfgang Schweiger, Vienna (AT); Manuel Hofer, Vienna (AT); Hermann Bürstmayr, Vienna (AT); Barbara Steiner, Vienna (AT)

(73) Assignee: DSM Austria GmbH, Getzersdorf (AT)

( * ) Notice: Subject to any disclaimer, the term of this patent is extended or adjusted under 35 U.S.C. 154(b) by 218 days.

(21) Appl. No.: 17/620,544

(22) PCT Filed: Jun. 19, 2020

(86) PCT No.: PCT/EP2020/067125
§ 371 (c)(1),
(2) Date: Dec. 17, 2021

(87) PCT Pub. No.: WO2020/254592
PCT Pub. Date: Dec. 24, 2020

(65) Prior Publication Data
US 2022/0298521 A1 Sep. 22, 2022

(30) Foreign Application Priority Data
Jun. 19, 2019 (EP) ..................................... 19181392

(51) Int. Cl.
| | |
|---|---|
| *C12N 9/10* | (2006.01) |
| *A23K 10/14* | (2016.01) |
| *A23K 10/30* | (2016.01) |
| *A23L 5/20* | (2016.01) |
| *C07K 14/415* | (2006.01) |
| *C12N 15/82* | (2006.01) |

(52) U.S. Cl.
CPC ............ *C12N 9/1088* (2013.01); *A23K 10/14* (2016.05); *A23K 10/30* (2016.05); *A23L 5/25* (2016.08); *C07K 14/415* (2013.01); *C12N 15/8242* (2013.01)

(58) Field of Classification Search
CPC .......................... C12N 9/1088; C12N 15/8242
See application file for complete search history.

(56) References Cited

U.S. PATENT DOCUMENTS

| | | |
|---|---|---|
| 6,500,639 B2 | 12/2002 | Subramanian |
| 2002/0184661 A1 | 12/2002 | Subramanian |

FOREIGN PATENT DOCUMENTS

| | | | |
|---|---|---|---|
| CN | 103834624 A | | 6/2014 |
| JP | 2002526107 A | * | 8/2002 |
| WO | 00/20573 A2 | | 4/2000 |
| WO | 00/47747 A2 | | 8/2000 |
| WO | 2000047747 A2 | † | 8/2000 |
| WO | 00/60061 A2 | | 10/2000 |
| WO | WO-2015169847 A1 | * | 11/2015 ............. A23K 10/30 |

OTHER PUBLICATIONS

Milne et al (An approach to gene-specific transcription inhibition using oligonucleotides complementary to the template strand of the open complex. PNAS. 97:3136-3141, 2000) (Year: 2000).*
Wahibah et al.(Expression of barley Glutathione S-Transferase13 gene reduces accumulation of reactive oxygen species by trichothecenes and paraquat in *Arabidopsis* plants. Plant Biotechnology 35, p. 71-79, 2018) (Year: 2018).*
Marcussen et al (Ancient hybridizations among the ancestral genomes of bread wheat. Science 345:1250092-1250092, 2014) (Year: 2014).*
Schreiber et al (Transcriptome-scale homoeolog-specific transcript assemblies of bread wheat. BMC Genomics, p. 1-14, 2012) (Year : 2012).*
Kumar et al (Glutathione S-Transferases: Role in Combating Abiotic Stresses Including Arsenic Detoxification in Plants. Frontiers in Plant Science. p. 1-9, 2018). (Year: 2018).*
De Sutter et al (Aphids transform and detoxify the mycotoxin deoxynivalenol via a type II biotransformation mechanism yet unknown in animals. Nature Scientific Report. p. 1-9, 2016) (Year: 2016).*
Arunachalam et al., "Trichothecene toxicity in eukaryotes: Cellular and molecular mechanisms in plants and animals," Toxicology Letters, vol. 217, No. 2, Dec. 2012, pp. 149-158.
Borisjuk et al., "Genetic Modification for Wheat Improvement: From Transgenesis to Genome Editing," BioMed Research International, vol. 2019, Article ID 6216304, Mar. 2019, pp. 1-18.
De Vries et al., "Biocatalytic conversion of epoxides," Current Opinion in Biotechnology, vol. 14, No. 4, Aug. 2003, pp. 414-420.
Fjellstedt et al., "Enzymatic Conjugation of Epoxides with Glutathione," The Journal of Biological Chemistry, vol. 248, No. 10, May 1973, pp. 3702-3707.

(Continued)

*Primary Examiner* — Wayne Zhong
(74) *Attorney, Agent, or Firm* — Mueting Raasch Group

(57) ABSTRACT

The present invention relates to a novel method for detoxification of trichothecene contaminated material. More specifically the present invention pertains to a method for biotransformation of a trichothecene by contacting material contaminated with trichothecenes with an exogenous non-animal glutathione-S-transferase (GST) having substrate specificity for the epoxide ring of the trichothecene. The invention further relates to recombinant GSTs and transgenic plants and animals expressing said GSTs.

Figure 1:
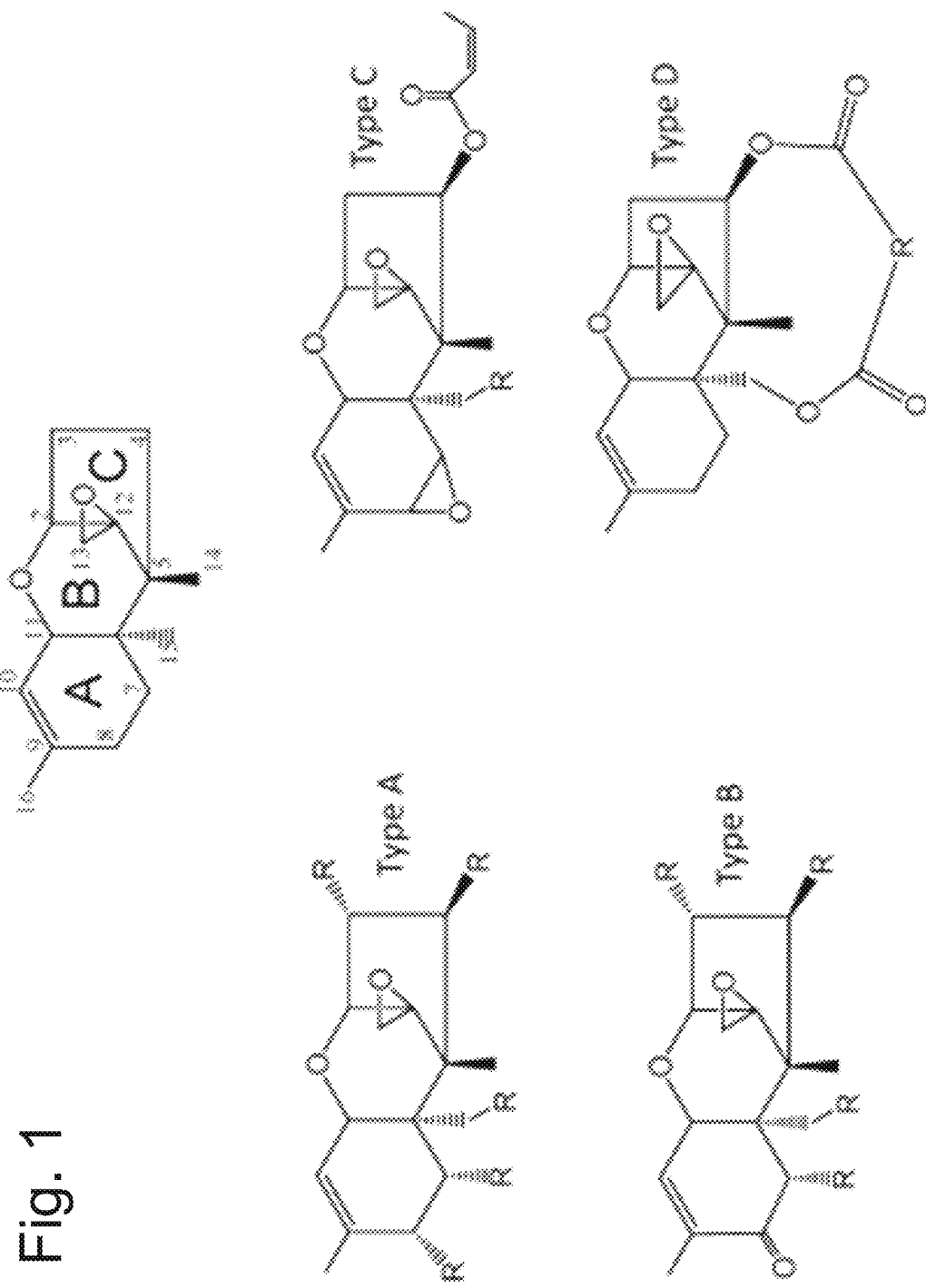

11 Claims, 13 Drawing Sheets
Specification includes a Sequence Listing.

(56)        References Cited

OTHER PUBLICATIONS

Foster et al., "A Possible Enzymic Assay for Trichothecene Mycotoxins in Animal Feedstuffs," Biochemical Society Transactions, vol. 3, No. 6, Dec. 1975, pp. 875-878.

Fruhmann et al., "Methylthiodeoxynivalenol (MTD): insight into the chemistry, structure and toxicity of thia-Michael adducts of trichothecenes," Organic and Biomolecular Chemistry, vol. 12, No. 28, May 2014, pp. 5144-5150.

Gardiner et al., "Transcriptome Analysis of the Barley-Deoxynivalenol Interaction: Evidence for a Role of Glutathione in Deoxynivalenol Detoxification," Molecular Plant-Microbe Interactions, vol. 23, No. 7, Jun. 2010, pp. 962-976,.

He et al., "Chemical and biological transformations for detoxification of trichothecene mycotoxins in human and animal food chains: a review," Trends in Food Science & Technology, vol. 21, No. 2, Feb. 2010, pp. 67-76.

He et al., "Meeting demands for increased cereal production in China," Journal of Cereal Science, vol. 59, No. 3, May 2014, pp. 235-244.

Janeway et al., "Immunobiology—The Immune System in Health and Disease" Fifth Edition, Garland Publishing, New York, 2001, 884 pp.

Karlovsky, P., "Biological detoxification of the mycotoxin deoxynivalenol and its use in genetically engineered crops and feed additives," Applied Microbiology and Biotechnology, vol. 91, No. 3, Jun. 2011, pp. 491-504.

Kluger et al., "Biotransformation of the Mycotoxin Deoxynivalenol in Fusarium Resistant and Susceptible Near Isogenic Wheat Lines," PLoS One, vol. 10, No. 3, Mar. 2015, pp. e0119659 (19 pp).

Kluger et al., "Stable isotopic labelling-assisted untargeted metabolic profiling reveals novel conjugates of the mycotoxin deoxynivalenol in wheat," Analytical and Bioanalytical Chemistry, vol. 405, No. 15, Oct. 2012, pp. 5031-5036.

McCormick, S.P., "Microbial Detoxification of Mycotoxins," Journal of Chemical Ecology, vol. 39, No. 7, Jul. 2013, pp. 907-918. (Abstract Only).

Pan et al., "Transcriptome dynamics associated with resistance and susceptibility against fusarium head blight in four wheat genotypes," BMC Genomics, vol. 19, No. 1, Article No. 642, Aug. 2018, pp. 1-26.

Sambrook et al., "Molecular Cloning—A Laboratory Manual," vols. 1-3, Third Edition, Cold Spring Harbor Laboratory Press, Cold Spring Harbor, New York, 2001, 2231 pp. (Filed in 7 parts).

Stanic et al., "Characterization of Deoxynivalenol-Glutathione Conjugates Using Nuclear Magnetic Resonance Spectroscopy and Liquid Chromatography-High Resolution Mass Spectrometry," Journal of Agricultural and Food Chemistry, vol. 64, No. 36, Aug. 2016, pp. 6903-6910.

Theodoulou et al., "Co-induction of glutathione-S-transferases and multidrug resistance associated protein by xenobiotics in wheat," Pest Management Science, vol. 59, No. 2, Jan. 2003, pp. 202-214.

Uhlig et al., "Glutathione-Conjugates of Deoxynivalenol in Naturally Contaminated Grain Are Primarily Linked via the Epoxide Group," Toxins, vol. 8, No. 11, Nov. 2016, pp. 329.

Wahibah et al., "Expression of barley Glutathione S-Transferase 13 gene reduces accumulation of reactive oxygen species by trichothecenes and paraquat in Arabidopsis plants," Plant Biotechnology, vol. 35, No. 1, Mar. 2018, pp. 71-79.

A Possible Enzymic Assay for Trichothecene Mycotoxins in Animal Feedstuffs.†

Enzymatic conjugation of epoxides with glutathione The Journal of Biological Chemistry.†

Expression of barley Glutathione S Transferase13 gene reduces accumulation of reactive oxygen species by trichothecenes and paraquat in Arabidopsis plants.†

* cited by examiner
† cited by third party

Fig. 11
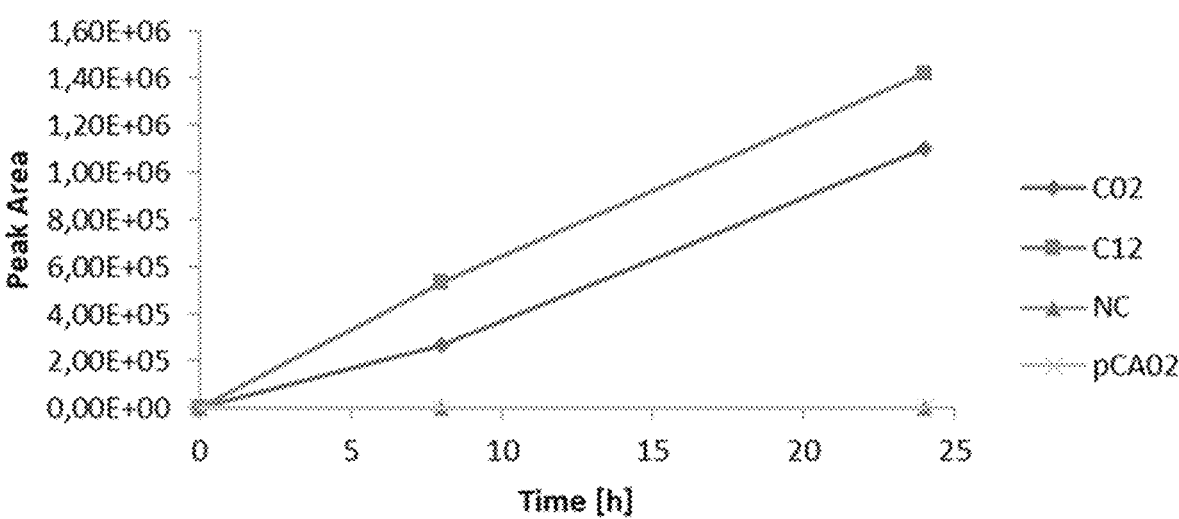
Fig. 12

METHOD FOR BIOTRANSFORMATION OF TRICHOTHECENES

PRIORITY CLAIM

This application claims priority to International Application No. PCT/EP2020/067125, filed Jun. 19, 2020, which claims priority to European Application No. 19181392.2 filed Jun. 19, 2019, wherein the contents of said applications are incorporated herein by reference in their entireties. Also, the entire contents of the ASCII text file entitled "IPM0129US_Sequence_Listing.txt" created on Dec. 17, 2021, and having a size of 52 kilobytes, is incorporated herein by reference.

The present invention relates to a novel method for detoxification of trichothecene contaminated material. More specifically, the present invention pertains to a method for biotransformation of a trichothecene by contacting material contaminated with trichothecenes with an exogenous non-animal glutathione-S-transferase (GST) having substrate specificity for the epoxide ring of the trichothecene. The invention further relates to recombinant GSTs and transgenic plants and animals expressing said GSTs.

BACKGROUND

Fungi produce a large number of metabolites that are not essential for life, but may provide the fungus with an ecological advantage in certain environments. Such metabolites are referred to as secondary metabolites. Fungal secondary metabolites include plant growth regulators (e.g., gibberellins), pharmaceutically useful compounds (e.g., penicillin, lovastatin), pigments (e.g., carotenoids), and mycotoxins (e.g., trichothecenes, fumonisins, aflatoxins, ochratoxins).

Trichothecene mycotoxins are a large family of chemically related mycotoxins with a common tricyclic 12,13-epoxytrichotec-9-ene (EPT) cores structure that are toxic to humans, animals, plants and eukaryotic cells in general. Fusaria and other trichothecene-producing fungi and molds such as *Fusarium, Myrochecium, Trichoderma, Trichothecium, Cephalosporium, Verticimonosporium*, and *Stachybotrys* infect important crop plants, for example grains of wheat, barley or maize. They have consequently become associated with human and animal intoxications throughout the world (Arunachalam C, Doohan F M., Toxicol Lett. 2013 Feb. 27; 217(2): 149-58. doi: 10.1016/j.toxlet.2012.12.003. Epub 2012 Dec. 26. Review). Trichothecenes have strong cytoxocity, as well as proinflammatory and emetogenic properties, and are harmful to hematopoietic organs and to immune function. Trichothecenes inhibit eukaryotic protein synthesis, specifically by preventing peptide bond formation at the peptidyl transferase center of the 60s ribosomal subunit, by inhibiting mitochondrial protein synthesis and by interacting with protein sulfhydryl groups. *Fusarium* toxins can occur in many types of human and animal food, including cereal grains such as barley, oats, rice, rye, teff, triticale, wheat, wild rice, finger millet, fonio, foxtail millet, Kodo millet, Japanese millet, Job's Tears, maize (corn), pearl millet, proso millet and sorghum. Toxins have also been found in hay, flax, peas, soy, rapeseed and other oilseeds such as sunflower, hemp and poppy. Trichothecene toxins may also occur in other types of food, e.g. in beets that are grown on a field where previous crop residues are plowed into the soil.

Trichothecenes are sesquiterpene compounds, small amphipathic molecules, that consist of the trichothecene core with epoxy rings at C-12 and -13 positions. Trichothecenes are classified into four types (A-D) based on the carbonyl group at the C-8 position, macrolide rings at 4- and 15-positions, and the number of epoxy rings. Among these types, type A-trichothecenes and type B-trichothecenes are of major relevance in agriculture. One of the most extensively studied trichothecenes is the type A-trichothecene T-2 toxin. Important type B-trichothecenes include deoxynivalenol (DON, vomitoxin) and nivalenol (NIV).

There are also macrocyclic trichothecenes (type D trichothecenes). Examples of macrocyclic trichothecenes include verrucarins, roridins, and satratoxin. Trichothecene mycotoxins are nonvolatile, low molecular weight compounds that are generally relatively soluble in water as well as in many organic solvents such as acetone, ethyl acetate, chloroform, dimethyl sulfoxide and ethanol.

Various enzymatic methods have been described in the literature relating to detoxification of deoxynivalenol and other trichothecenes. Most of these detoxifcation reactions are targeting side groups (e.g. reduction and epimerization of the C3-OH group, acetylation of the C3-OH, glycosylation of C3-OH, hydroxylation of C16).

The reduction of the epoxide to an olefin ($C=C$) by anaerobic bacteria has been described but a hypothetical "epoxide-reductase" is so far elusive and no gene has been cloned. The status of enzymatic (microbial) detoxification has been reviewed (Karlovsky P., 2011, Appl. Microbiol. Biotechnol., 91(3), 491-504; McCormick S P., 2013, J. Chem. Ecol., 39(7), 907-18). The epoxide of trichothecenes is remarkably unreactive. No epoxide-hydrolase (opening the epoxide by addition of water) capable to inactivate trichothecenes is known. Epoxide opening catalyzed by glutathione-S-transferase (GST) is known to occur in some cases (de Vries E J. & Janssen D B, 2003, Curr. Opin. Biotechnol., 14(4), 414-429).

Figure 2:
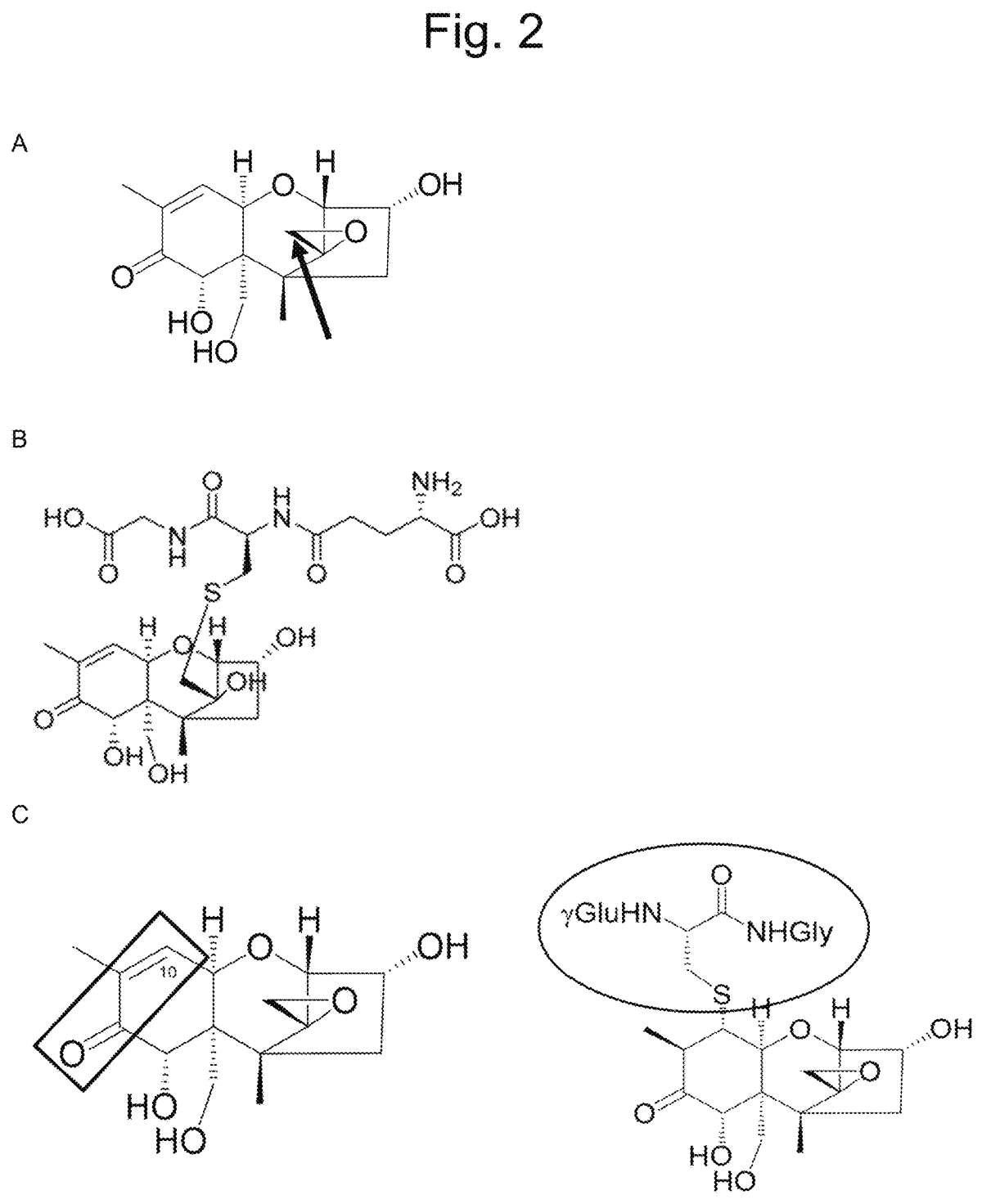

Gardiner S A. et al. (Molecular Plant-Microbe Interactions, 2010, 23 (7): 962-976) reported that glutathione can spontaneously (nonenzymatically) react with DON by forming a so-called Michael adduct (FIG. 2, left structure). DON-glutathione conjugates and processing products were found in planta (Kluger B. et al, 2013, Analytical and Bioanalytical Chemistry, 405, 15, 5031-5036). It was shown that addition of the small S-methyl group (a presumed degradation product) to the double bond considerably reduces the toxicity (Fruhmann P. et al, 2014, Org. Biomol. Chem., 12(28), 5144-5150), indicating that addition of the bulky glutathione should likewise prevent interaction with the ribosomal target. Yet, the Michael adduct is rather unstable especially under alkaline conditions and upon removal of glutathione from the equilibrium the original toxin can be regenerated.

More recently it was described that in a very slow reaction (after weeks at alkaline conditions) also the epoxide can be opened by spontaneous reaction with glutathione (Stanic A. et al., 2016, J. Agric. Food Chem, 64(36), 6903-6910). This reaction (FIGS. 2 A & B) is considered to be irreversible (yet data on stability of the product are still scarce). Further processing of the epoxide-glutathione adduct in vivo is likely, so far (Kluger B. et al., 2015, PLOS One 10 (3): e0119656.) there is only evidence for a derivative where 2 hydrogens are missing from the DON part.

The adduct to C13 (epoxide) has been found in (extensively stored) wheat, and it was proposed (Uhlig S. et al., 2016, Toxins 8 (11):329) that this is the result of a spontaneous (nonenzymatic) transfer of the glutathione from the double bond (Michael adduct) to the epoxide.

WO2015/169847A1 reports non-enzymatic detoxification of trichothecene involving trichothecene epoxide ring opening by reaction with a thiol under alkaline conditions.

WO2000/20573A2 discloses the use of nucleic acids obtained by DNA shuffling for mycotoxin detoxification, such as nucleic acids encoding an enzyme with glutathione-S-transferase activity.

Wahibah N. N., et al. report a method for detoxification of reactive oxygen species and toxic compounds with an exogenous non-animal glutathione S-transferase (Plant Biotechnology 2018, 35(1), 71-79).

He J., et al. provide a review on biotransformations for detoxification of trichothecene in food chains (Trends in Food Science and Technology 2010, 21(2), 67-76).

He Z., et al. report demands for increased cereal production in China (Journal of Cereal Science 2014, 59(3), 235-244).

Borisjuk N., et al. describe genetic modification for increased wheat production (Biomed Research International 2019, 2019, 1-18).

Pan Y, et al. disclose transcriptome analysis and identification of differentially expressed genes such as genes encoding glutathione S transferase, membrane proteins and distinct LRR-RKs, which are associated with resistance towards *fusarium* (BMC Genomics 2018, 19(1), 1-26).

Theodoulou F., et al. report co-induction of glutathione-S-transferases and multidrug resistance associated protein by xenobiotics such as herbicides (Pest Management Science 2003, 59(2), 202-214).

Contamination with trichothecene mycotoxins is a worldwide issue necessitating disposal and destruction of huge amounts of agricultural products every year. Since preventive measures have not yet been successful to prohibit mycotoxin contamination, there is a need to find a method for providing detoxified and decontaminated material as well as for providing methods for decontaminating contaminated substances.

SUMMARY OF THE INVENTION

Thus, it is an object of the invention to provide a method for biotransformation of trichothecenes.

The object is solved by the subject matter of the present invention.

The present invention provides a method for biotransformation of a trichothecene by contacting material contaminated with trichothecenes with an exogenous non-animal glutathione-S-transferase (GST) having substrate specificity for the epoxide ring of the trichothecene, comprising the steps of:

a) contacting the material with the GST, b) adding glutathione to said material, and c) incubating the mixture in an aqueous solution at a pH range of about 6 to 9 under conditions wherein glutathione reacts with the epoxide moiety, thereby forming an epoxide adduct.

The incubation is allowed to proceed for a time period sufficient for the epoxide adduct formation to take place to reduce the amount of trichothecene toxin in a material to an acceptable level, such as a level acceptable for consumption by humans and/or animals.

According to a further embodiment the trichothecene is selected from the group of type A trichothecenes, type B trichothecenes, type C trichothecenes, and type D trichothecenes, specifically the trichothecene is selected from the group consisting of trichodermol, trichodermin, 4,15-diacetoxyscirpenol (DAS), neosolaniol, T-2 toxin, HT-2 toxin, isotrichodermol, calonectrin, 7,8-dihydroxy calonectrin, harzianum A, nivalonol (NIV), deoxynivalenol (DON), 3- and 15-acetyldeoxynivalenol, fusarenon-X, trichothecin, trichothecolone, trichothecinol A, crotocin, satratoxin H, roridin A, baccharin, verrucarin A.

More specifically, the trichothecene is selected from T-2 toxin, HT-2 toxin, neosolaniol, deoxynivalenol (DON), nivalenol (NIV), 3- and 15-acetyldeoxynivalenol, roridin A and verrucarin A.

In general, the method as described herein can be used for any material or substance which may be contaminated with trichothecene mycotoxins.

According to a specific embodiment of the invention the method as described herein is used for producing a decontaminated feed additive, feed material, food additive or food material.

According to a further embodiment the method as described herein is used for decontaminating aerosol, liquid or solid material or material surface, specifically textile material, filter material, gas masks, air conditioning systems, for purifying material surfaces, animal or human surface such as skin etc.

In a further embodiment, the GST used for the method as described herein is a recombinant GST.

According to a specific embodiment, the GST has an amino acid sequence of SEQ ID NO. 2, or SEQ ID NO. 4, or a sequence having at least 80%, 85%, 90%, 95%, specifically at least 99% sequence identity with any one of SEQ ID NO. 2, or SEQ ID NO. 4 and having substrate specificity for the epoxide ring of the trichothecene.

According to a further specific embodiment, the GST comprises 1, 2, 3, 4, 5, 6, 7, 8, 9, or 10 amino acid modifications of SEQ ID NO. 2, or SEQ ID NO. 4.

In yet a further embodiment, the GST is encoded by a polynucleotide sequence selected from the group consisting of a) SEQ ID NO. 1, or SEQ ID NO. 3, or a sequence having at least 80%, 85%, 90%, 95%, specifically at least 99% sequence identity with any one of SEQ ID NO. 1, or SEQ ID NO. 3, or b) an isolated nucleic acid molecule that is complementary to a polynucleotide sequence of a).

According to a further specific embodiment, the GST is encoded by a polynucleotide sequence selected from the group consisting of a) SEQ ID NO. 1, or SEQ ID NO. 3 having 1, 2, 3, 4, 5, 6, 7, 8, 9, 10, 11, 12, 13, 14, 15, 16, 17, 18, 19 20, and up to 50 nucleotide modifications or b) an isolated nucleic acid molecule that is complementary to a polynucleotide sequence of a).

According to an embodiment, the GST is expressed in a host cell.

The invention also provides a feed additive or feed material comprising exogenous non-animal GST having substrate specificity for the epoxide ring of a trichothecene and optionally glutathione.

According to a specific embodiment, the feed additive or feed material comprises a transgenic plant part, transgenic plant tissue, transgenic plant cell, seed or progeny thereof, specifically leaf, stem, root, cotyledon, or hypocotyl, each of the foregoing containing an exogenous GST having substrate specificity for the epoxide ring of the trichothecene.

According to a specific embodiment, the method as described herein is used for enzymatic degradation of trichothecene in animal feed or in the digestive tract of animals.

According to an alternative embodiment, the described method is used for producing feed or food additive.

The invention also provides feed or food material comprising decontaminated plant material obtained by the method described herein.

Further provided herein is a host overexpressing an endogenous GST or transformed with a vector expressing an exogenous GST, wherein said GST has substrate specificity for the epoxide ring of a trichothecene. Specifically, the host is a prokaryote or eukaryote, specifically it is a plant cell, an animal cell, a fungal cell or a bacterial cell.

According to a further embodiment, the host cell comprises a GST, wherein the GST is encoded by
   a) a polynucleotide sequence selected from the group consisting of SEQ ID NO. 1, SEQ ID NO. 3, or a sequence having at least 80%, 85%, 90%, 95%, specifically at least 99% sequence identity with any one of SEQ ID NO. 1, SEQ ID NO. 3, or
   b) an isolated nucleic acid molecule that is complementary to a).

According to a further embodiment, the host cell comprises an expression cassette. Specifically, the expression cassette comprises a polynucleotide sequence encoding an exogenous GST, operably linked to a regulatory sequence, such as but not limited to CaMV 35S, NOS, OCS, Adhl, AdhII and Ubi-1, malE functional in said host.

In a further embodiment, the expression cassette further comprises a scorable marker polynucleotide, such as, but not limited to, GUS, GFP, CAT, LUC, Sialidase, operably linked to a regulatory sequence functional in a plant. Additionally, a selection marker polynucleotide, such as, but not limited to, nptII, hptII, pat and bar is operably linked to the regulatory sequence functional in said host.

In a further embodiment, a host is provided which expresses the GST described herein that has substrate specificity for a trichothecene selected from the group of type A trichothecenes, type B trichothecenes, type C trichothecenes, type D trichothecenes.

The present invention further provides a host expressing the GST and having substrate specificity for a trichothecene selected from the group of type A trichothecenes, type B trichothecenes, type C trichothecenes, and type D trichothecenes, specifically the trichothecene is selected from the group of the group consisting of trichodermol, trichodermin, 4,15-diacetoxyscirpenol (DAS), neosolaniol, T-2 toxin, HT-2 toxin, isotrichodermol, calonectrin, 7,8-dihydroxy calonectrin, harzianum A, nivalonol (NIV), deoxynivalenol (DON), 3- and 15-acetyldeoxynivalenol, fusarenon-X, trichothecin, trichothecolone, trichothecinol A, crotocin, satratoxin H, roridin A, baccharin, and verrucarin A.

More specifically, the trichothecene is selected from T-2 toxin, HT-2 toxin, neosolaniol, deoxynivalenol (DON), nivalenol (NIV), 3- and 15-acetyldeoxynivalenol, roridin A and verrucarin A.

According to a specific embodiment, the exogenous GST of the host comprises the amino acid sequence selected from the group of SEQ ID NO. 2, SEQ ID NO. 4, or a sequence having at least 80%, 85%, 90%, 95%, specifically at least 99% sequence identity with any one of SEQ ID NO. 2, SEQ ID NO. 4, and having substrate specificity for the epoxide ring of a trichothecene.

Further provided is a transgenic plant with increased resistance towards trichothecene, comprising an exogenous GST having substrate specificity for the epoxide ring of a trichothecene.

Further, a transgenic plant part, transgenic plant tissue, transgenic plant cell, seed or progeny thereof, specifically leaf, stem, root, cotyledon, and hypocotyl, comprising an exogenous GST having substrate specificity for the epoxide ring of a trichothecene is provided.

According to an embodiment, also a transgenic animal with increased resistance towards trichothecene, comprising an exogenous GST having substrate specificity for the epoxide ring of a trichothecene is provided herein.

The invention further provides a method of producing a transgenic plant or animal, comprising transforming a plant or animal with a nucleic acid molecule encoding GST, and expressing the nucleic acid molecule in said plant wherein said nucleic acid molecule comprises a polynucleotide sequence selected from the group consisting of the polynucleotide sequence comprising SEQ ID NO. 1, or SEQ ID NO.3, or a sequence having at least 80%, 85%, 90%, 95%, specifically at least 99% sequence identity with any one of SEQ ID NO. 1, or SEQ ID NO. 3.

According to a further embodiment, the plant can be transformed by a method selected from the group consisting of Agrobacterium-mediated transformation, particle gun bombardment, vacuum-infiltration, in planta transformation and a chemical method.

The present invention also provides a method for expressing exogenous GST having substrate specificity for the epoxide ring of a trichothecene in a host, comprising:
   a) transforming a host cell with a vector containing the GST encoding gene sequence, and
   b) growing the transformed cell under conditions suitable for the expression of the gene encoding the exogenous GST.

The transgenic plant as described herein can be a monocotyledonous or a dicotyledonous plant.

Specifically, the monocotyledonous plant is a grass, specifically selected from the group consisting of rice, maize, wheat, barley, sorghum, rye, and oat.

Specifically, the dicotyledonous plant is selected from the group of tobacco, tomato, pea, soybean, Brassica, chickpea, Arabidopsis, and carrot.

FIGURES

FIG. 1: Trichothece carbon numbering system and structures of different types of trichothecenes. Structures of trichothecene and type A, B, C and D trichothecenes.

FIG. 2: A) Deoxynivalenol (DON), epoxide opening. The arrow points to the carbon atom that is attacked by the SH group of glutathione. B) DON-glutathione adduct. The structure of the resulting DON-glutathione epoxide adduct is shown (secondarily the C15-OH can also react with C8-keto to form a hemiketal). C) Structural requirement for Michael adduct formation, resulting DON-GSH adduct. Formation of the Michael adduct is only possible if a conjugated double bond and keto-group exist (type B trichothecenes).

Figure 3:
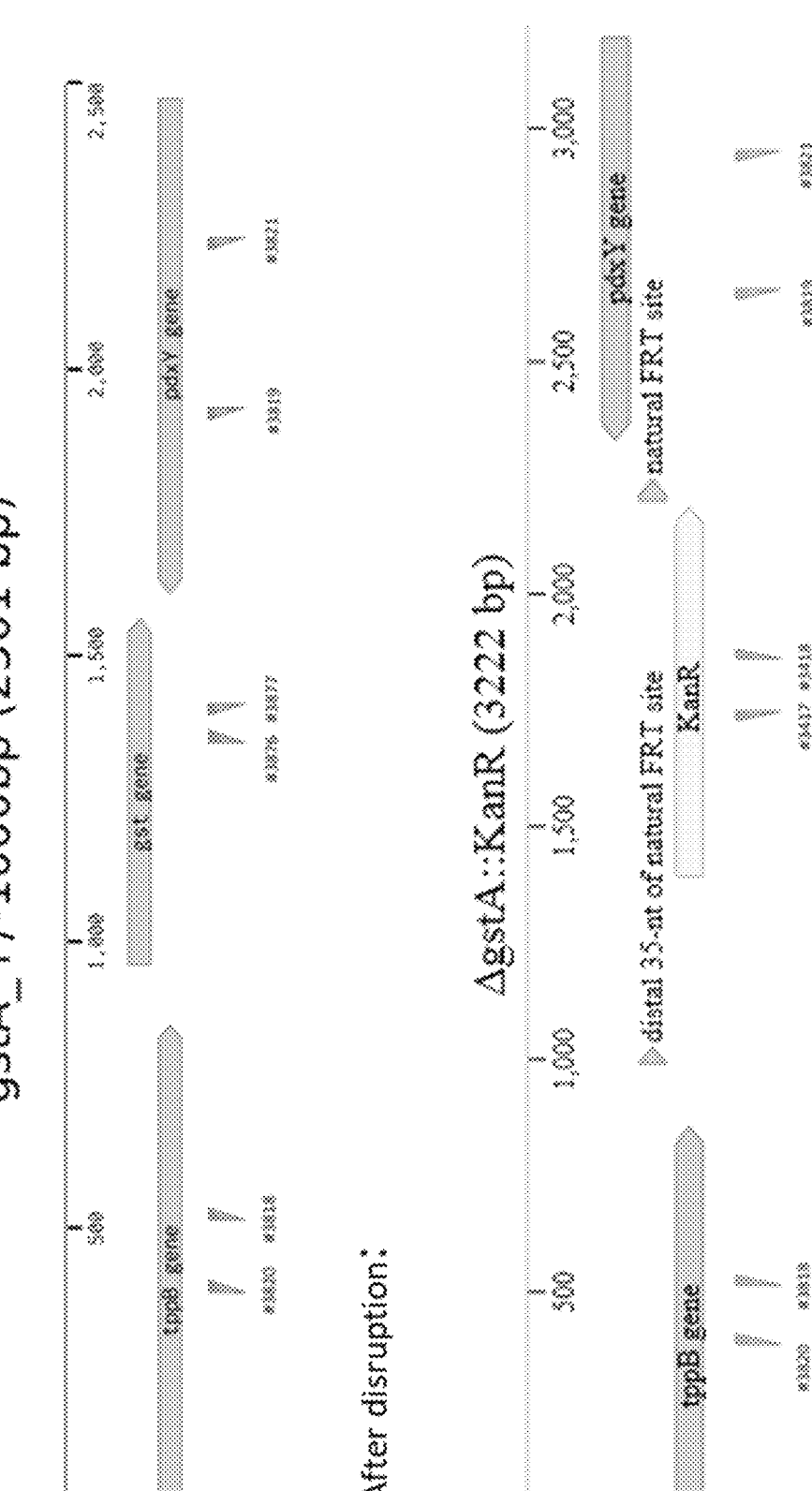

FIG. 3: Construction of the gsh T7-Express host strain. Schematic comparison of wild type (A) and disruption strain (B).

Figure 4:
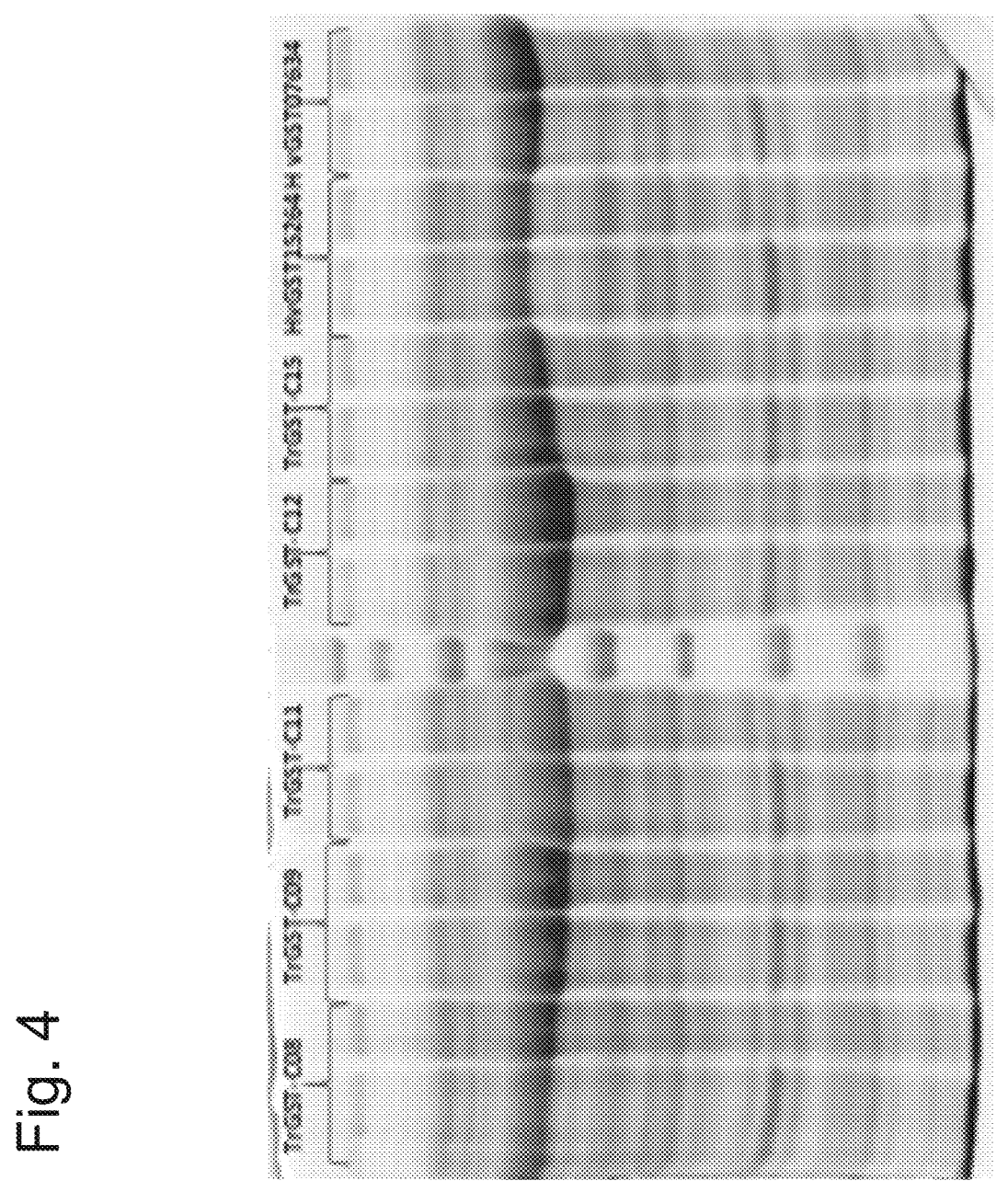

FIG. 4: SDS PAGE of 6×HIS-malE-(TEV)-GST fusion proteins. Results of an SDS PAGE 12% polyacrylamide used to assess expression of the 6×HIS-malE-(TEV)-GST fusion proteins. From each candidate, two samples were loaded on the gels: total protein on the left and cell extract (cleared lysate) on the right.

Figure 5:
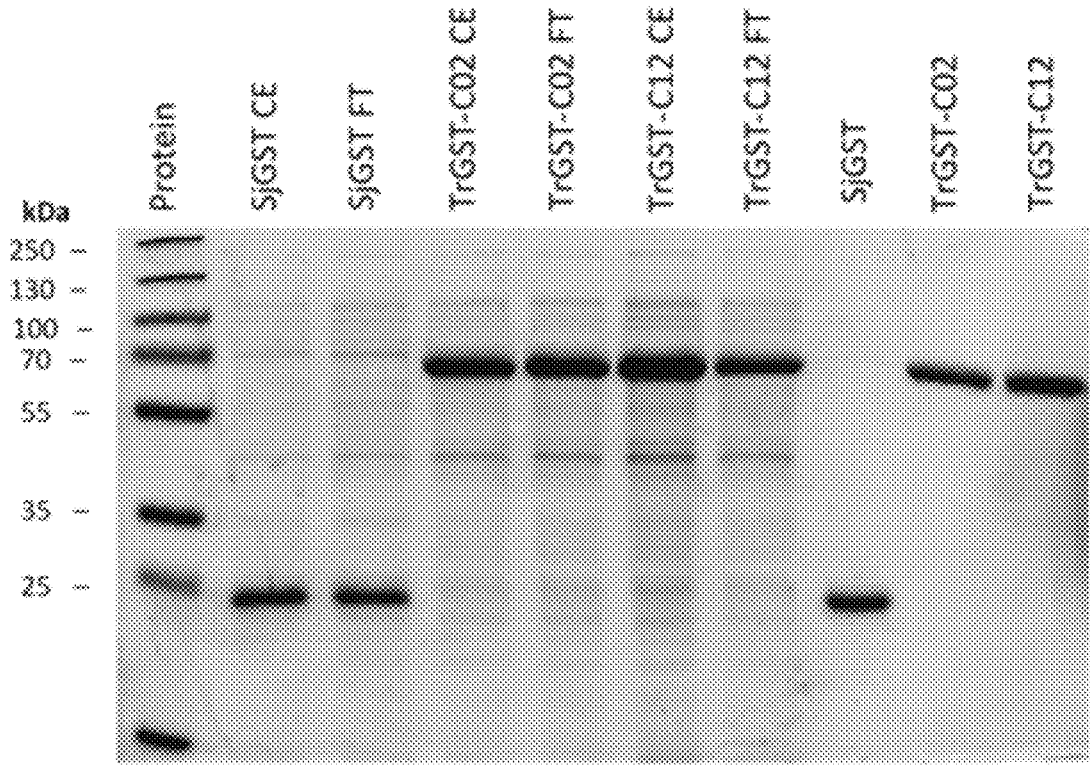

FIG. 5: SDS-PAGE protein purification. Applied concentrations: CE (cell extract) and FT (flow through: 0.75 mg/ml, Protein: 0.23 mg/mL FIG. 6: Enzymatic formation of the Michael adduct of DON (MH1), using different GSTs.

Figure 6:
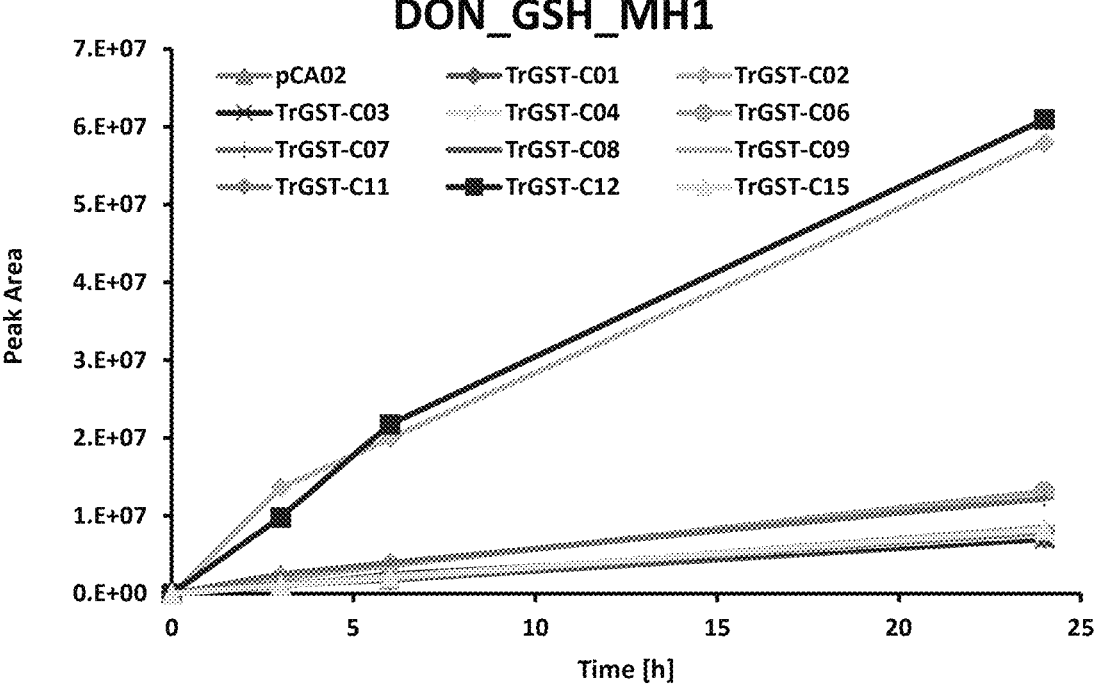
Figure 7:
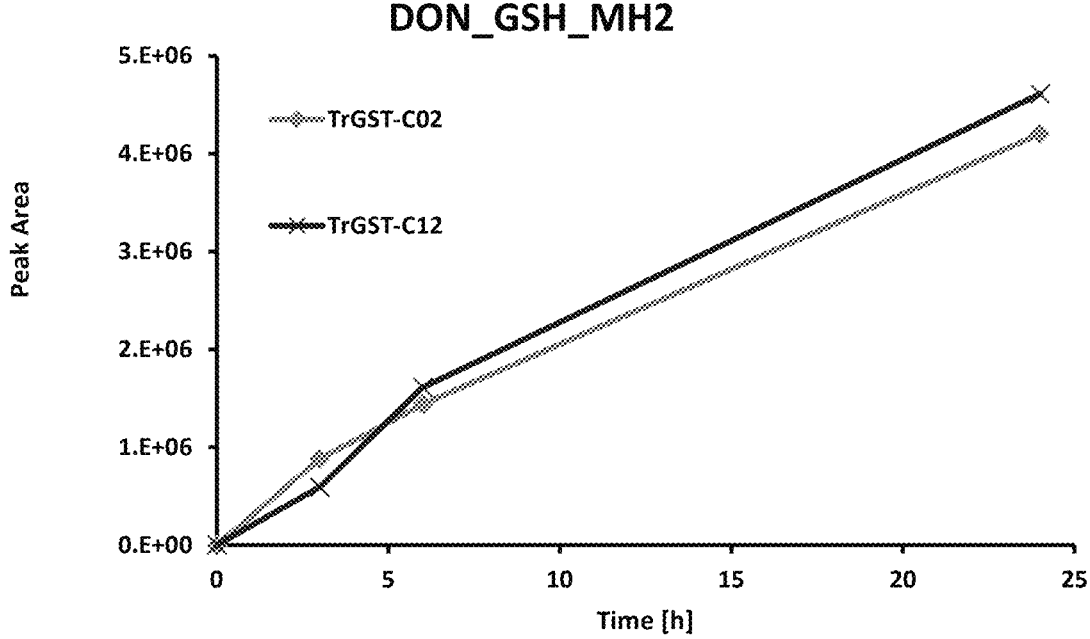

FIG. 7: Enzymtic formation of the epoxide-adduct of DON (MH2), catalyzed by GST C02 and C12. The same GSTs were used as for the DON-GSH_MH1 assay shown in FIG. 6, but GSTs other than GST C02 and C12 did not show detectable epoxide-adduct formation.

Figures 8, 9:
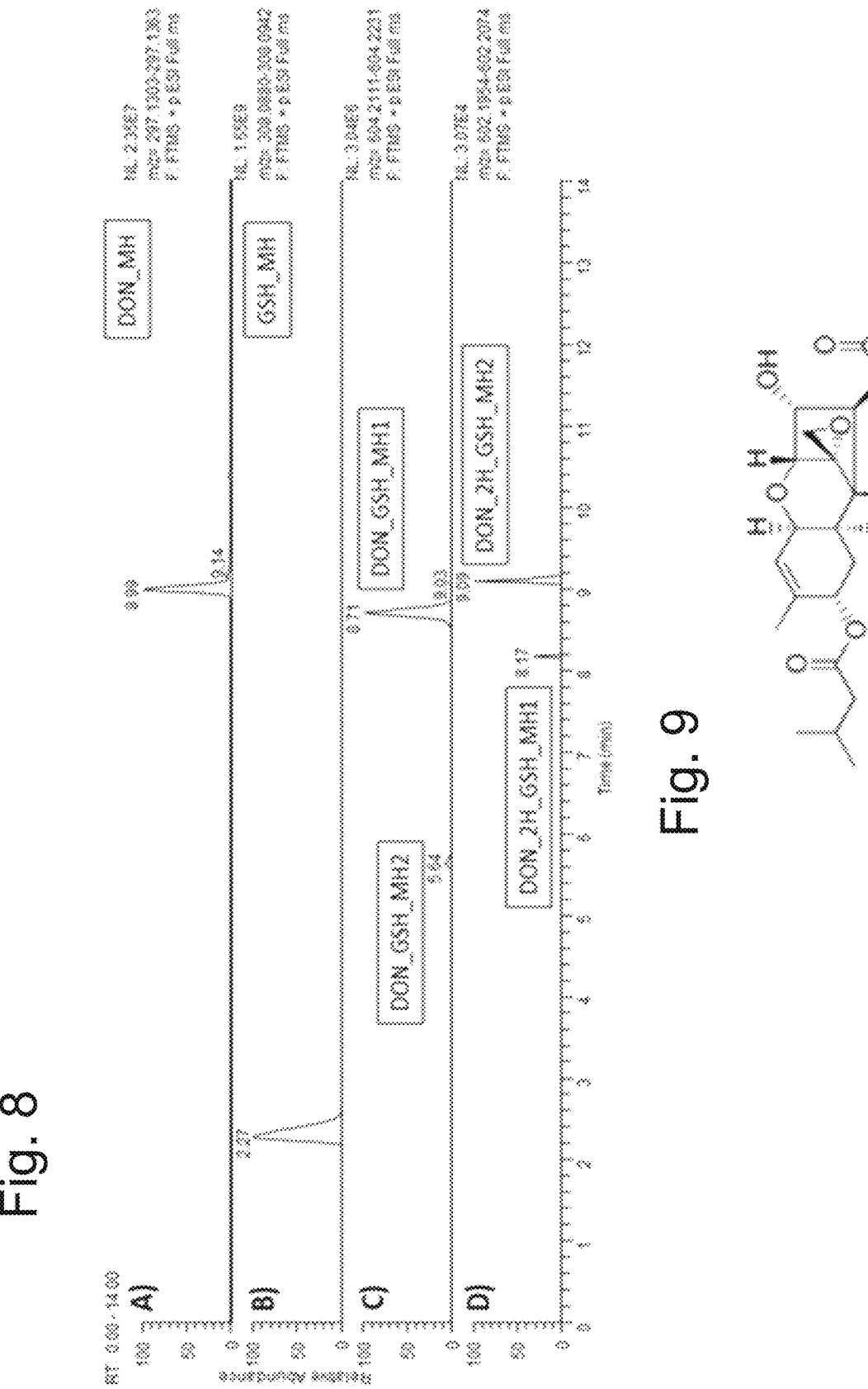

FIG. 8: Extracted ion chromatograms for DON (reaction with wheat GST C02).

FIG. 9: Structure of T-2 toxin

Figure 10:
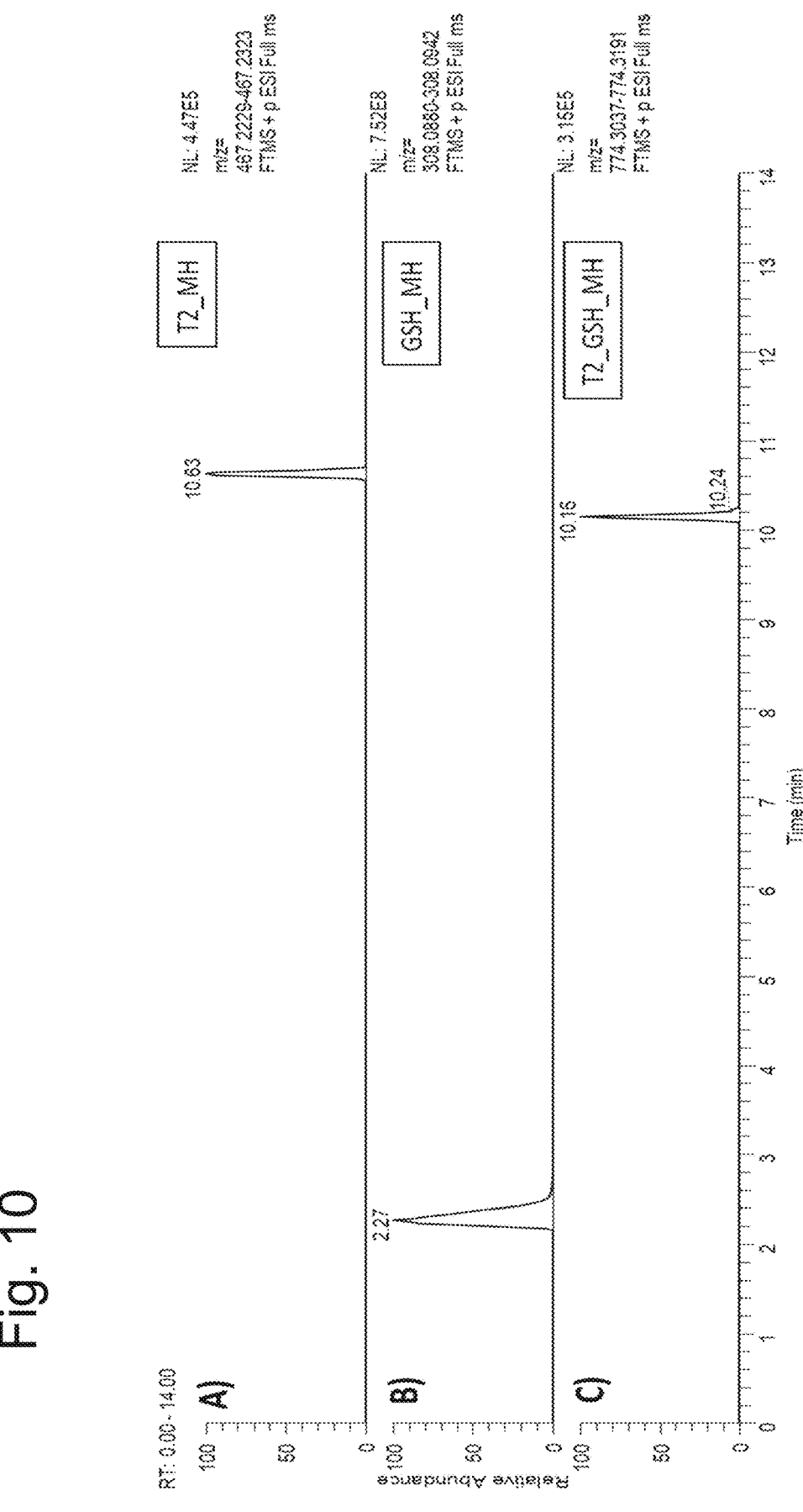

FIG. 10: Extracted ion chromatograms of the [M+H]$^+$ ions of A) T2, B) GSH, C) T2_GSH (mass window: ±5 ppm)

FIG. 11: Enzyme dependent formation of the GSH adduct with T-2 toxin. T-2-GSH_MH, pCA02 is the empty vector, NC is the negative control (no protein), TaGSTs C02/C12

FIG. 12: Structure of trichodermin

Figure 13:
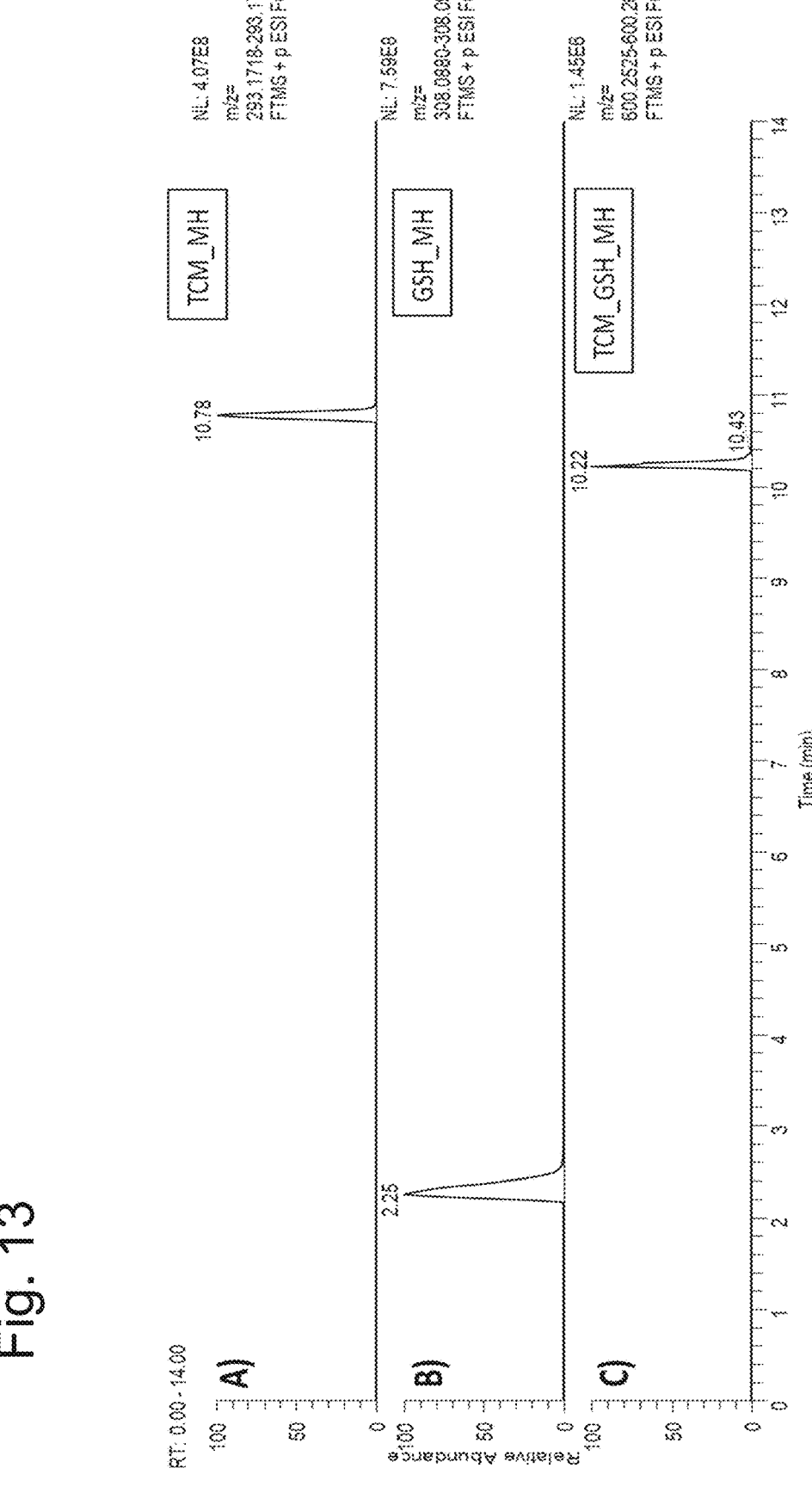

FIG. 13: Extracted ion chromatograms of the [M+H]$^+$ ions of A) TCM, B) GSH, C) TCM_GSH (mass window: ±5 ppm)

Figure 14:
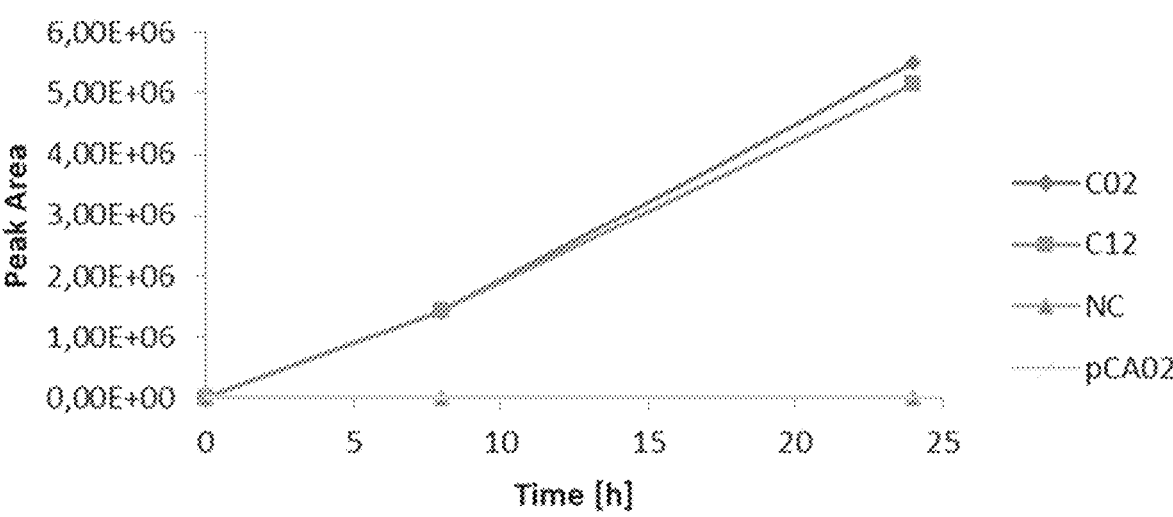

FIG. 14: Enzyme dependent formation of the GSH adduct with trichodermin. Trichodermin-GSH_MH; pCA02 is the empty vector, NC is the negative control (no protein), TaGSTs C02/C12

Figure 15:
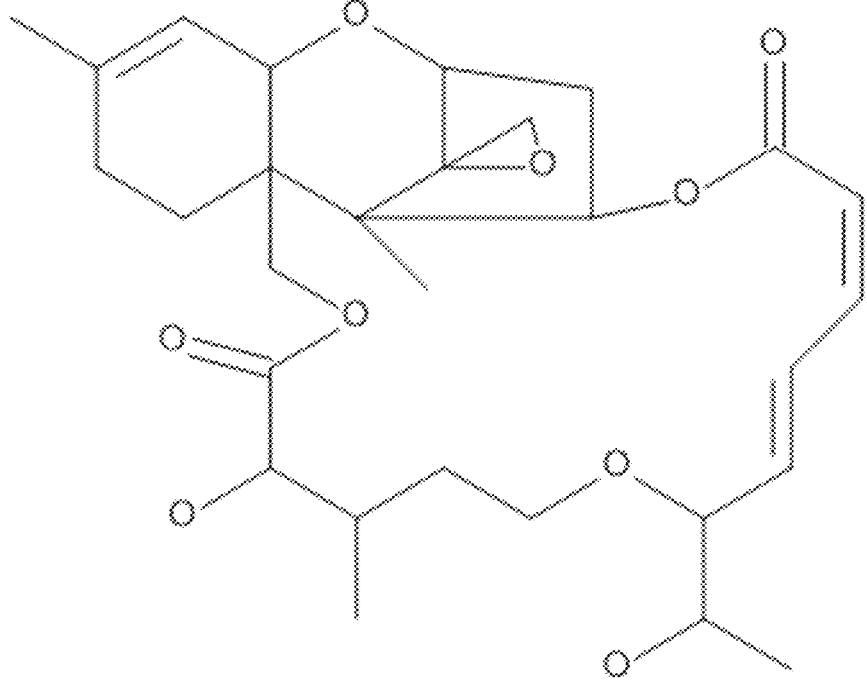

FIG. 15: Structure of roridin A (ROA)

Figure 16:
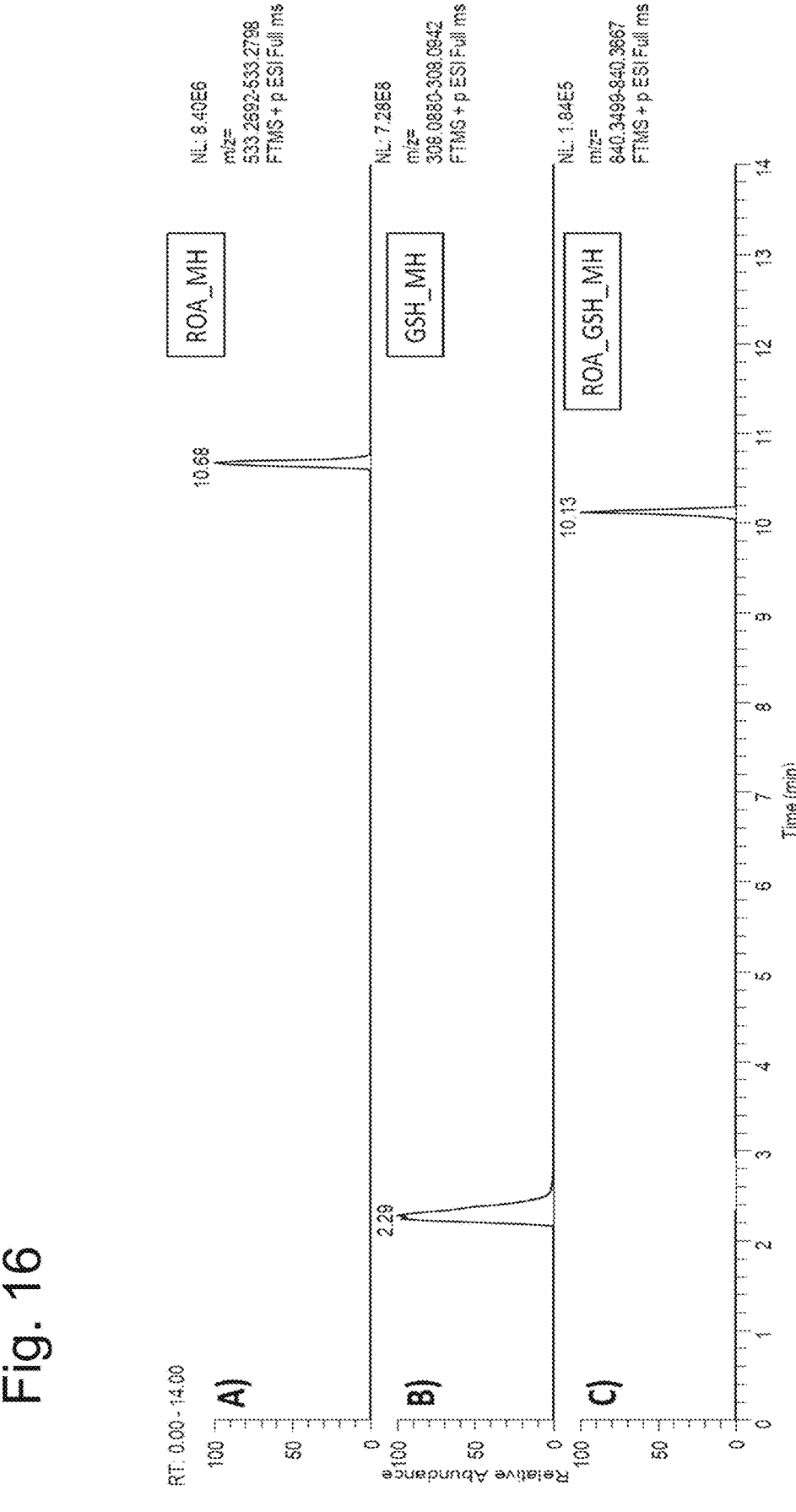

FIG. 16: Extracted ion chromatograms of the [M+H]$^+$ ions of A) ROA, B) GSH, C) ROA_GSH (mass window: ±5 ppm)

Figure 17:
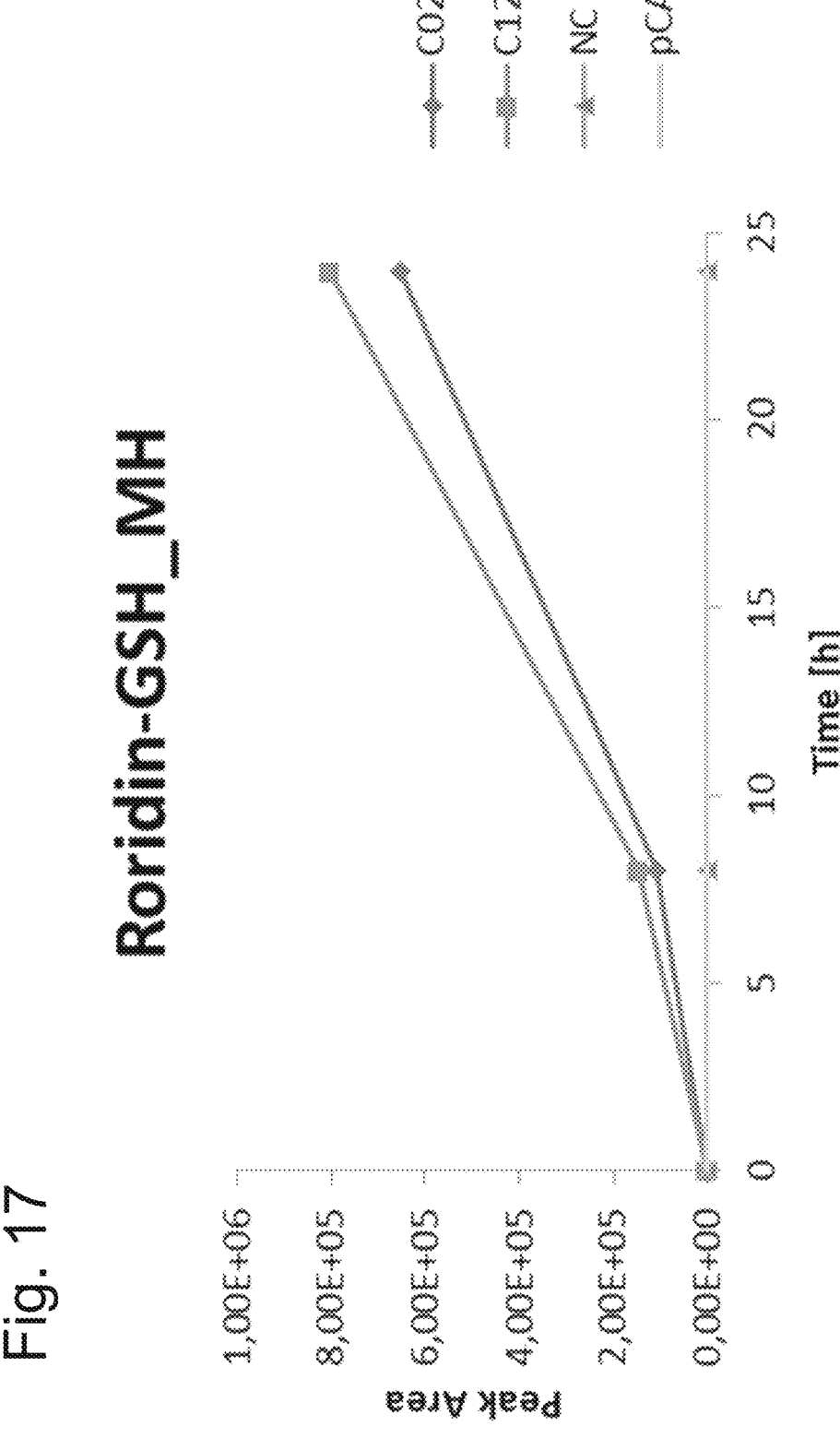

FIG. 17: Enzyme dependent formation of the GSH adduct with roridin A. Roridin-GSH_MH; pCA02 is the empty vector, NC is the negative control (no protein), TaGSTs C02/C12

DETAILED DESCRIPTION

Unless indicated or defined otherwise, all terms used herein have their usual meaning in the art, which will be clear to the skilled person. Reference is for example made to standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Janeway et al, "Immunobiology" (5th Ed., or more recent editions, Garland Science, New York, 2001).

The subject matter of the claims specifically refers to artificial products or methods employing or producing such artificial products, which may be variants of native (wild-type) products. Though there can be a certain degree of sequence identity to the native structure, it is well understood that the materials, methods and uses of the invention, e.g., specifically referring to isolated nucleic acid sequences, amino acid sequences, fusion constructs, expression constructs, transformed host cells and modified proteins including enzymes, are "man-made" or synthetic, and are therefore not considered as a result of "laws of nature".

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

As used herein and in the claims, the singular form, for example "a", "an" and "the" includes the plural, unless the context clearly dictates otherwise.

Herein provided is a novel method for biotransfomation of trichothecenes using non-animal GST having substrate specificity for the epoxide ring of trichothecenes.

Glutathione S-transferases (GSTs) comprise a family of eukaryotic and prokaryotic phase II metabolic isozymes known for their ability to catalyze the conjugation of the reduced form of glutathione (GSH) to xenobiotic substrates for the purpose of detoxification. The GST family consists of three superfamilies: the cytosolic, mitochondrial, and microsomal proteins. Members of the GST superfamily are extremely diverse in amino acid sequence, and a large fraction of the sequences deposited in public databases are of unknown function.

"Non-animal GST" refers to GST from any origin except animal origin such as rat or any other kind of animal.

Type A trichothecenes include compounds that have a hydroxyl group at C-8 (e.g., neosolaniol), an ester function at C-8 (e.g., T-2 toxin), or no oxygen substitution at C-8 (e.g., trichodermin, 4,15-diacetoxyscirpenol, and harzianum A).

Trichothecene type A: trichodermol, trichodermin, 4,15-diacetoxyscirpenol (DAS), neosolaniol, T-2 toxin, HT-2 toxin, isotrichodermol, calonectrin, 7,8-dihydroxy calonectrin, harzianum A Type B trichothecenes have a keto (carbonyl) function at C-8 (e.g., nivalenol, deoxynivalenol, and trichothecin).

In *Fusarium*, type B trichothecenes typically have a C-7 hydroxyl group, but this structural feature is not present in other genera.

Trichothecene type B: nivalonol (NIV), deoxynivalenol (DON), 3- and 15-acetyldeoxynivalenol, fusarenon-X, trichothecin, trichothecinol A Type C trichothecenes have a C-7/C-8 epoxide (e.g. crotocin).

Trichothecene type C: crotocin.

Type D trichothecenes have an additional ring linking the C-4 and C-15 position (e.g., roridin A, verrucarin A, satratoxin H).

Trichothecene type D: satratoxin H, roridin A, baccharin, verrucarin A

All *Fusarium* trichothecenes (including type A and type B) have an oxygen function (i.e., a hydroxyl or an acetyl group) at C-3. Trichothecenes produced by *Trichoderma, Trichothecium, Myrothecium* or *Stachybotrys* (including types A, B, C and D) lack an oxygen function at the C-3 position.

For the herein described method for biotransformation, contaminated material is contacted with GST and glutathione and incubated for a time period sufficient for the detoxification reaction to take place to reduce the amount of trichothecene toxin by forming epoxide adduct in a sample to an acceptable level, such as a level acceptable for consumption by humans and/or animals. Specifically, the trichothecene is fully converted to an epoxide adduct by the herein described inventive method.

For example, the biotransformation reaction may proceed for about one hour to 24 hours, specifically, the material is incubated with the GST for 1, 2, 3, 4, 5, 10, 15, 20, 24 hours. Specifically, biotransformation reaction is stopped within 24 hours.

The reaction may take place at ambient temperature, such as room temperature. Also, it may be possible to perform the reaction at elevated temperatures, such as temperatures commonly employed in food and feed production. These may e.g. be from about 30° C. to about 40° C.

The biotransformation reaction may for example be performed at a pH of about 6 to 9, such as a pH range from about 6.5. to 8.5.

The biotransformation method disclosed herein may be used for detoxification of any kind of trichothecene contaminated material. The material may contain one kind of a type A, B, C or type D trichothecene toxin, or two or more kinds of type A, B, C and/or type D toxins. Typically, the material is a product intended for use as a food or feed, feed additive or food additive, as such or after processing, such as an agricultural product. In a further example, the sample is a food product or a feed product. Exemplary material to be treated includes, but is not limited to, hay or straw, grains or seeds, flour and other milled products, livestock or fish feed. The material may be a grain-derived or grain-containing product, such as grain or seeds intended for food or feed production. Typical grains include, but are not limited to, oats, barley, maize, rye, rice, sorghum, wheat, teff, triticale, wild rice, finger millet, fonio, foxtail millet, Kodo millet, Japanese millet, Job's Tears, pearl millet, and proso millet. Other examples of material which may be contaminated with trichothecenes include flax, peas, soy, rapeseed and other oilseeds such as sunflower, hemp and poppy. Trichothecene toxins may also occur in other types of food, e.g. in beets. Grain-derived products include, but are not limited to, raw grain, flour and cereals. Also, grass and animal feed products are suitable for detoxification in accordance with the present document. The method can also be used for decontaminating non-food materials or surfaced thereof such as textile material, e.g. clothes, filter material, gas masks, air conditioning systems etc.

The method described herein can also be used for purifying materials and material surfaces from trichothecenes, and also for purifying or decontaminating animal and human surfaces like skin, hair, fur etc.

Specifically, the GST is a recombinant GST.

As used herein, the term "recombinant" refers to a molecule or construct that does not naturally occur in a host cell. In some embodiments, recombinant nucleic acid molecules contain two or more naturally-occurring sequences that are linked together in a way that does not occur naturally. A recombinant protein refers to a protein that is encoded and/or expressed by a recombinant nucleic acid. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. "Recombination", "recombining", and generating a "recombined" nucleic acid generally encompass the assembly of at least two nucleic acid fragments. In certain embodiments, recombinant proteins and recombinant nucleic acids remain functional, i.e., retain their activity or exhibit an enhanced activity in the host cell.

Specifically, the recombinant GST comprises one of the following nucleotide or amino acid sequences:

```
                        (TrGST-CO2, SEQ ID NO. 1)
AATGGCCGGAGGAGATGACTTGAAGCTGCTGGGCG

CTTGGGCAAGTCCATTTGTCACCAGGGTGAAGCTT

GCGCTGAACTTCAAGGGCCTGAGCTTCGAGGATGT

CGAAGAGGACCTTAGCAACAAGAGCGAGCTCCTCC

TCAGCTCGAACCCGGTGCACAAGAAGGTGCCCGTG

CTCGTCCACAACGGAAAACCCATTTGCGAGTCAGT
```

-continued
```
GATCATCGTTCAGTACATCGATGAGGCGTTCGCCG

GCATCGGCCCCGCTCTCCTTCCCTCTGACCCCTAC

GAACGCGCCATTGCCCGTTTCTGGGCCGCCTACGT

TGACGATAAGCTCGTCGCCCCATGGGTACAGTCGT

TGAGGGCCAAGACAGAGGAGGAGAAGTCCGAGGGG

CTTAAGCAGACATTTGCCGCGGTGGAGACACTGGA

AGGAGCCCTGCGGGAGTGCTCCAAGGGAGAGGGCT

ACTTTGGTGGTGAGACCGTCGGGCTTGTGGACATT

TCACTTGGGAGCCTGCTCTCCTGGTTGAACGCGAC

AGAAGTGATGTCCGGAACCAAGATATTTGATCCTG

TTAAGACTCCGCTCCTGGCAGCGTGGATGGAGCGC

TTTAGCAAGCTCGATGCTGCCAAGGCGGCGTTGCC

AGAAGTTGATAGGGTGGTCGAATTTGCCAAGAAGA

GACAAGCACAGGCTGCTGCCGCCGCCGCTGCTTCA

GAGACCAAGTAA
```

```
                        (TrGST-CO2, SEQ ID NO. 2)
MAGGDDLKLLGAWASPFVTRVKLALNFKGLSFEDV

EEDLSNKSELLLSSNPVHKKVPVLVHNGKPICESV

IIVQYIDEAFAGIGPALLPSDPYERAIARFWAAYV

DDKLVAPWVQSLRAKTEEEKSEGLKQTFAAVETLE

GALRECSKGEGYFGGETVGLVDISLGSLLSWLNAT

EVMSGTKIFDPVKTPLLAAWMERFSKLDAAKAALP

EVDRVVEFAKKRQAQAAAAAASETK
```

```
                        (TrGST-C12, SEQ ID NO. 3)
ATGGCCGGAGGAGATGACTTGAAGCTGCTCGGCGC

TTGGGCGAGTCCATTTGTCGCCAGGGTGAAGCTTG

CGCTGAGCTTCAAGGGCCTGAGCTTCGAGGATGTC

GAGGAGGACCTCAGCAACAAGAGCGAGCTCCTCCT

CAGCTCGAACCCGGTGCACAAGAAGGTGCCCGTGC

TCGTCCACAACGGGAAACCCATTTGCGAGTCAATG

ATCATCGTTCAGTACATCGATGAGGCGTTCCTTGT

CGGCCCCTCTCTTCTTCCCTCTGACCCCTACAAAC

GTGCAATTGCCCGTTTTTGGGCCGCCTACATTGAC

GATAAGCTCGTCACCCCATGGGTACAGTCGTTGAG

GGCCAAGACAGAGGAGGAGAAGTCTGAGGGGGTTA

AGCAGACATTTGCCGCTGTGGAAACACTGGAAGGA

GCCCTGAGGGAGTGCTCCAAGGGAGAGGGCTACTT

TGGTGGTGAGACCGTCGGGCTTGTGGACATTTCAC

TTGGGAGCCTGCTCTCCTGGTTGATTGCGACAGAA

GTGATGTCTGGAACCAAGATCTTTGATCCTGTTAA

GACTCCGCTCCTGGCAGCGTGGATGGGCGCTTTA

GCGAGCTCGACGCTGCCAAGGCGGCGTTGCCAGAA
```

11

-continued

```
GTTGATAGGGTGGTCGAATTTGCCAAGAAGAGACA

GGCACAGGCTGATGCCGCCGCCGCTGCTTCGGAGA

CCAAGTAA (TrGST-C12, SEQ ID NO. 4)
MAGGDDLKLLGAWASPFVARVKLALSFKGLSFEDV

EEDLSNKSELLLSSNPVHKKVPVLVHNGKPICESM

IIVQYIDEAFLVGPSLLPSDPYKRAIARFWAAYID

DKLVTPWVQSLRAKTEEEKSEGVKQTFAAVETLEG

ALRECSKGEGYFGGETVGLVDISLGSLLSWLIATE

VMSGTKIFDPVKTPLLAAWMGRFSELDAAKAALPE

VDRVVEFAKKRQAQADAAAAASETK
```

The GST can have amino acid sequence SEQ ID NO. 2 or SEQ ID NO. 4, or a sequence having at least 80%, 85%, 90%, 95%, specifically at least 99% sequence identity with SEQ ID NO. 2, or SEQ ID NO. 4 and having substrate specificity for the epoxide ring of the trichothecene. As an alternative, amino acid sequences SEQ ID NO. 2 or SEQ ID NO. 4 may comprise 1, 2, 3, 4, 5, 6, 7, 8, 9 or 10 modifications, with the proviso, that the GST comprising SEQ ID NO 2 or SEQ ID NO 4 preserves its substrate specificity for the epoxide ring of the trichothecene.

The GST may be encoded by nucleic acid sequence SEQ ID NO. 1 or SEQ ID NO. 3, or a sequence having at least 80%, 85%, 90%, 95%, specifically at least 99% sequence identity with SEQ ID NO. 1, or SEQ ID NO. 3 and having substrate specificity for the epoxide ring of the trichothecene. As an alternative, nucleic acid sequences SEQ ID NO. 1 or SEQ ID NO. 3 may comprise 1, 2, 3, 4, 5, 6, 7, 8, 9, 10, 15, 20, or more modifications, with the proviso, that the GST encoded by SEQ ID NO. 1 or SEQ ID NO. 3 preserves its substrate specificity for the epoxide ring of the trichothecene.

Amino acid or nucleotide modifications herein refer to any modifications known in the art such as point mutations, deletions or insertions of amino acid residues or nucleotides.

"Percent (%) identity" with respect to an amino acid sequence, homologs and orthologues described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

For purposes described herein, the sequence identity between two amino acid sequences is determined using the NCBI BLAST program version 2.2.29 (Jan. 6, 2014) with blastp set at the following exemplary parameters: Program: blastp, Word size: 6, Expect value: 10, Hitlist size: 100, Gapcosts: 11.1, Matrix: BLOSUM62, Filter string: F, Genetic Code: 1, Window Size: 40, Threshold: 21, Composition-based stats: 2.

"Percent (%) identity" with respect to a nucleotide sequence e.g., of a nucleic acid molecule or a part thereof, in particular a coding DNA sequence, is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at novocraft.com), ELAND (Illumina, San Diego, CA), SOAP (available at soap.genomie-s.org.cn), and Maq (available at maq.sourceforge.net).

For expressing the GST described herein, any host cell can be used appropriate for expressing recombinant exogenous functional GST having substrate specificity for the epoxide ring of the trichothecene. Host cells can be prokaryotic or eukaryotic cells or cell cultures. Such host cells may be, but are not limited to fungal cells such as *Saccharomyces* sp., bacterial cells, such as *E. coli*, plant cells, or animal cells. Due to recombinant expression of the GST described herein, the so transformed host cells may have substrate specificity for trichothecenes, specifically type A trichothecenes, type B trichothecenes, type C trichothecenes, and type D trichothecenes, specifically for deoxynivalenol (DON), 3- and 15-acetyldeoxynivalenol, nivalenol (NIV), T2 toxin HT-2 toxin, neosolaniol, diacetoxyscirpenol, trichothecin, roridin A and verrucarin A. Due to substrate specificity, host cells may better tolerate contamination by trichothecenes.

Specifically, transgenic plants or parts therefrom such as tissues, seed, leafs, stems, roots, cotyledons or hypocotyls are provided, expressing exogenous GST having substrate specificity for the epoxide ring of a trichothecene. Such plants can be monocotyledonous or dicotyledonous plants, such as but not limited to rice, maize, wheat, barley and sorghum, rye, oat or tobacco, tomato, pea, soybean, Brassica, chickpea, Arabidopsis, and carrot.

Specifically, also transgenic, non-human animals are provided herein having increased resistance towards trichothecene, comprising an exogenous GST having substrate specificity for the epoxide ring of a trichothecene. Specifically, transgenic species such as pigs, fish or insects may thereby be able to better tolerate toxin contaminated feed.

The term "exogenous non animal glutathione-S-transferase" as used herein refers to a non-animal GST not naturally present in a material contaminated with trichothecene or not being originally expressed in the material. The term "exogenous" may be used interchangeably with the term "foreign". The non-animal GST is present in the material as a result of the addition of said GST protein or by expression of a GST coding sequence in a transgene DNA sequence of a host cell or organism, thereby encoding an exogenous GST. The exogenous GST is any non-animal GST that is added to the material and/or is expressed in an organism or (host) cell that originated outside that material or organism, as opposed to an endogenous factor.

The term "expression" is understood in the following way. Nucleic acid molecules containing a desired coding sequence of an expression product such as the GST described herein, as described herein may be used for expression purposes. Such nucleic acid molecules are specifically referred to as "isolated nucleic acid molecule" or "isolated nucleotide sequence". Hosts transformed or transfected with these sequences are capable of producing the encoded proteins. In order to effect transformation, the expression system may be included in a vector; however, the relevant DNA may also be integrated into the host chromosome. Specifically, the term refers to a host cell and compatible vector under suitable conditions, e.g., for the expression of a protein coded by foreign DNA carried by the vector and introduced to the host cell.

Coding DNA is a DNA sequence that encodes a particular amino acid sequence for a particular polypeptide or protein. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors often include one or more replication systems for cloning or expression, one or more markers for selection in the host, e.g., antibiotic resistance, one or more nuclear localization signals (NLS) and one or more expression cassettes.

"Expression vectors" or "vectors" as used herein are defined as DNA sequences that are required for the transcription of cloned recombinant nucleotide sequences, i.e. of recombinant genes and the translation of their mRNA in a suitable host organism. To obtain expression, a sequence encoding a desired expression product, such as the GST described herein, is typically cloned into an expression vector that contains a promoter to direct transcription. Suitable bacterial and eukaryotic promoters are well known in the art. The promoter used to direct expression of a nucleic acid depends on the particular application. For example, a strong constitutive promoter is typically used for expression and purification of recombinant proteins. In contrast, when the expression product is to be administered in vivo for gene regulation, either a constitutive or an inducible promoter can be used, depending on the particular use of the expression product. In addition, a preferred promoter for administration can be a weak promoter. Expression vectors comprise the expression cassette and additionally usually comprise an origin for autonomous replication in the host cells or a genome integration site, one or more selectable markers (e.g., an amino acid synthesis gene or a gene conferring resistance to antibiotics such as zeocin, kanamycin, G418 or hygromycin; or nptII, hptII, pat and bar), a number of restriction enzyme cleavage sites, a suitable promoter sequence and a transcription terminator, which components are operably linked together. Vectors can also contain regulatory elements such as, but not limited to CaMV, 35S, NOS, AdhI, AdhII, Ubi-1, and mal E.

An "expression cassette" refers to a DNA coding sequence or segment of DNA coding for an expression product that can be inserted into a vector at defined restriction sites. The cassette restriction sites are designed to ensure insertion of the cassette in the proper reading frame. Generally, foreign DNA is inserted at one or more restriction sites of the vector DNA, and is then carried by the vector into a host cell along with the transmissible vector DNA. A segment or sequence of DNA having inserted or added DNA, such as an expression vector, can also be called a "DNA construct".

The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g., a foreign gene) can be introduced into a host cell, so as to transform the host and promote expression (e.g., transcription and translation) of the introduced sequence.

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al.). Plants can be transformed by *Agrobacterium*-mediated transformation, particle gun bombardment, vacuum-infiltration, in planta transformation and chemical methods known by the skilled person in the art.

The following items are particular embodiments of the invention provided herein.

1. A method for biotransformation of a trichothecene by contacting material contaminated with trichothecenes with an exogenous non-animal glutathione-S-transferase (GST) having substrate specificity for the epoxide ring of the trichothecene, comprising the steps of:
   a) contacting the material with the GST,
   b) optionally adding glutathione to said material, and
   c) incubating the mixture in an aqueous solution at a pH range of 6 to 9 under conditions wherein glutathione reacts with the epoxide moiety, thereby forming an epoxide adduct.

2. The method according to item 1, wherein the trichothecene is selected from the group of type A trichothecenes, type B trichothecenes, type C trichothecenes, and type D trichothecenes.

3. The method according to item 1 or 2, wherein the trichothecene is selected from the group of T-2 toxin, HT-2 toxin, neosolaniol, deoxynivalenol (DON), nivalenol (NIV), trichothecin, 3- and 15-acetyldeoxynivalenol, roridin A and verrucarin A.

4. The method according to any one of items 1 to 3, for producing a decontaminated feed additive, feed material, food additive or food material.

5. The method according to any one of items 1 to 3, for decontaminating liquid or solid material or material surface, specifically textile material, filter material, gas masks, air conditioning systems.

6. The method according to any one of items 1 to 3, for purifying material surfaces, animal or human surface.

7. The method according to any one of items 1 to 6, wherein the GST is a recombinant GST.

8. The method according to any one of items 1 to 7, wherein the GST has an amino acid sequence of SEQ ID NO. 2, or SEQ ID NO. 4, or a sequence having at least 80%, 85%, 90%, 95%, specifically at least 99% sequence identity with any one of SEQ ID NO. 2, or SEQ ID NO. 4 and having substrate specificity for the epoxide ring of the trichothecene.

9. The method according to any one of items 1 to 8, wherein the GST is encoded by a) a polynucleotide sequence selected from the group consisting of SEQ ID NO. 1, or SEQ ID NO. 3, or a sequence having at least 80%, 85%, 90%, 95%, specifically at least 99% sequence identity with any one of SEQ ID NO. 1, or SEQ ID NO. 3, or b) an isolated nucleic acid molecule that is complementary to a polynucleotide sequence of a).

10. The method according to any one of items 1 to 9, wherein GST is expressed in a host cell.

11. Feed additive or feed material comprising exogenous non-animal GST having substrate specificity for the epoxide ring of a trichothecene.

12. Feed additive or feed material according to item 11, comprising a transgenic plant part, transgenic plant tissue, transgenic plant cell, seed or progeny thereof, specifically leaf, stem, root, cotyledon, or hypocotyl, each of the foregoing containing an exogenous GST having substrate specificity for the epoxide ring of the trichothecene.

13. Use of a method according to any one of items 1 to 10, for enzymatic degradation of trichothecene in animal feed or in the digestive tract of animals.

14. Use of a method according to any one of items 1 to 10, for producing feed or food additive.

15. Feed or food material comprising decontaminated plant material obtained by the method according to any one of items 1 to 10.

16. Fee additive according to item 15, wherein the non-animal GST has an amino acid sequence of SEQ ID NO. 2, or SEQ ID NO. 4, or a sequence having at least 80%, 85%, 90%, 95%, specifically at least 99% sequence identity with any one of SEQ ID NO. 2, or SEQ ID NO. 4 and having substrate specificity for the epoxide ring of the trichothecene.

17. A host overexpressing an endogenous GST or transformed with a vector expressing an exogenous GST, wherein said GST has substrate specificity for the epoxide ring of a trichothecene.

18. The host cell according to item 17, wherein the exogenous GST comprises the amino acid sequence selected from the group of SEQ ID NO. 2, SEQ ID NO. 4, or a sequence having at least 80%, 85%, 90%, 95%, specifically at least 99% sequence identity with any one of SEQ ID NO. 2, SEQ ID NO. 4, and having substrate specificity for the epoxide ring of a trichothecene.

19. The host according to item 17 or 18, which is a prokaryote or eukaryote, specifically it is a plant cell, an animal cell, a fungal cell or a bacterial cell.

20. The host according to items 17 to 19, wherein the GST is encoded by a) a polynucleotide sequence selected from the group consisting of SEQ ID NO. 1, SEQ ID NO. 3, or a sequence having at least 80%, 85%, 90%, 95%, specifically at least 99% sequence identity with any one of SEQ ID NO. 1, SEQ ID NO. 3, or b) an isolated nucleic acid molecule that is complementary to a).

21. The host according to any one of items 17 to 20, wherein the vector comprises an expression cassette, specifically comprising a polynucleotide sequence encoding an exogenous GST, operably linked to a regulatory sequence functional in said host.

22. The host according to item 21, wherein said cassette further comprises a scorable marker polynucleotide operably linked to a regulatory sequence functional in a plant.

23. The host according to item 21 or 22, wherein said cassette further comprises a selection marker polynucleotide operably linked to the regulatory sequence functional in said host.

24. The host according to any one of items 21 to 23, having substrate specificity for a trichothecene selected from the group consisting of type A trichothecenes, type B trichothecenes, type C trichothecene and type D trichothecenes.

25. The host according to any one of items 21 to 24, wherein the trichothecene is selected from the group of deoxynivalenol (DON), 3- and 15-acetyldeoxynivalenol, nivalenol (NIV), T2 toxin HT-2 toxin, neosolaniol, diacetoxyscirpenol, trichothecin, roridin A and verrucarin A.

26. The host according to any one of items 21 to 25, wherein the exogenous GST comprises the amino acid sequence selected from the group of SEQ ID NO. 2, and SEQ ID NO. 4, or a sequence having at least 80%, 85%, 90%, 95%, specifically at least 99% sequence identity with any one of SEQ ID NO. 2, and SEQ ID NO. 4 and having substrate specificity for the epoxide ring of a trichothecene.

27. A transgenic plant with increased resistance towards trichothecene, comprising an exogenous GST having substrate specificity for the epoxide ring of a trichothecene.

28. A transgenic plant part, transgenic plant tissue, transgenic plant cell, seed or progeny thereof, specifically leaf, stem, root, cotyledon, and hypocotyl, comprising an exogenous GST having substrate specificity for the epoxide ring of a trichothecene.

29. A transgenic animal with increased resistance towards trichothecene, comprising an exogenous GST having substrate specificity for the epoxide ring of a trichothecene.

30. A method of producing a transgenic plant or animal of item 27 to 29, comprising transforming a plant or animal with a nucleic acid molecule encoding GST, and expressing the nucleic acid molecule in said plant wherein said nucleic acid molecule comprises a polynucleotide sequence selected from the group consisting of the polynucleotide sequence comprising SEQ ID NO: 1, or SEQ ID NO. 3, or a sequence having at least 80%, 85%, 90%, 95%, specifically at least 99% sequence identity with any one of SEQ ID NO. 1, or SEQ ID NO. 3.

31. The method of item 30, wherein the plant is transformed by a method selected from the group consisting of *Agrobacterium*-mediated transformation, particle gun bombardment, vacuum-infiltration, in planta transformation and a chemical method.

32. A method for expressing exogenous GST having substrate specificity for the epoxide ring of a trichothecene in a host, comprising:

a) transforming a host cell with a vector containing the GST encoding gene sequence, b) growing the transformed cell under conditions suitable for the expression of the gene encoding the exogenous GST.

33. The method of producing the transgenic plant according to any one of items 28 to 30, wherein said plant is a monocotyledonous or a dicotyledonous plant.

34. The method according to item 31, wherein the mono-cotyledonous plant is a grass, specifically selected from the group consisting of rice, maize, wheat, barley and sorghum, rye, oat.

35. The method according to item 34, wherein the dicoty-ledonous plant is selected from the group consisting of tobacco, tomato, pea, soybean, Brassica, chickpea, Arabidopsis, and carrot.

The examples which follow are set forth to aid in the understanding of the invention but are not intended to, and should not be construed to limit the scope of the invention in any way. The examples do not include detailed descriptions of conventional methods. Such methods are well known to those of ordinary skill in the art.

EXAMPLES

Example 1

Construction of the Expression Host:

To be able to detect activity of a plant GST in a standard colorimetric assay a suitable *E. coli* host strain was constructed in which the endogenous GST gene (gstA) showing activity with the standard substrate (chloro-2,4-dinitrobenzene (CDNB)) of a colorimetric assay was inactivated. The gstA gene in the T7 polymerase based *E. coli* expression host "T7 Express" was disrupted as follows: First the plasmid pDK46 (with a temperature sensitive replication origin, and an arabinose inducible phage lambda recombination system (γ β exo) obtained from strain BW25113/pKD46 (http://cgsc2.biology.yale.edu/Strain.php?ID=68099) was introduced into the expression strain T7 express. Arabinose induced competent cells were then transformed with a PCR product obtained from the gstA mutant strain JW1627-1 from the systematic knockout collection of *E. coli* (http://cgsc2.biology.yale.edu/Strain.php?ID=107667). The PCR product obtained with flanking primers (Del_gstA_fw #3818 and Del_gstA_rv #3819) contains a kanamycin resistance gene. Knock out mutants were selected on LB-KAN medium at 37° C., which also leads to loss of pKD46. The gene replacement was confirmed by PCR. A comparison of wild type and disrupted strain is shown in FIG. 3 (A: Wild type, B: after disruption of endogenous gstA gene)

TABLE 1

| | | Primer sequences for generating gstA gene disruption mutants. | | |
|---|---|---|---|---|
| ID | name | Primer sequence | length bp | Purpose |
| 3417 | Kan screen fwd | GCATCAGCC ATGATGGAT AC (SEQ ID NO. 8) | 20 | Verification of gstA knockout in *E. Coli* T7 Express |
| 3418 | Kan screen rv | ATCTGGACG AAGAGCATC AG (SEQ ID NO. 7) | 20 | Verification of gstA knockout in *E. Coli* T7 Express |
| 3818 | Del_gstA_ fw | GCTATGGCC TGCAGAGCA TCGG (SEQ ID NO. 9) | 22 | Amplification of gstA knockout cassette from JW1627-1 (#2200) |

TABLE 1-continued

| | | Primer sequences for generating gstA gene disruption mutants. | | |
|---|---|---|---|---|
| ID | name | Primer sequence | length bp | Purpose |
| 3819 | Del_gstA_ rv | GGTTAAACA CCTGGCGCG AGCT (SEQ ID NO. 10) | 22 | Amplification of gstA knockout cassette from JW1627-1 (#2200) |
| 3820 | Del_gstA_ ver_fw | CCCTGCCGA TGCCAACCA AGTT (SEQ ID NO. 11) | 22 | Verification of gstA knockout in *E. Coli* T7 Express |
| 3821 | Del_gstA_ ver_rv | TGGCTATCT GGGATCGGC GGAG (SEQ ID NO. 12) | 22 | Verification of gstA knockout in *E. Coli* T7 Express |
| 3876 | gstA_ver_ fw | AGAAGAAGC TGCAATATG TGAA (SEQ ID NO. 5) | 22 | Verification of gstA knockout in *E. Coli* T7 Express |
| 3877 | gstA_ver_ rv | TTGTAAATC TTTGCCCGC AG (SEQ ID NO. 6) | 22 | Verification of gstA knockout in *E. Coli* T7 Express |

After disruption, the resulting strain "T7 Express ΔgstA:: Kan$^R$" has the following genotype:

ΔgstA785::kan fhuA2 lacZ::T7 gene1 [lon] ompT gal sulA11 R(mcr-73::miniTn10-Tet$^S$)2 [dcm] R(zgb-210:: Tn10-Tet$^S$) endA1 Δ(mcrC-mrr)114::IS10; T7 Polymerase (lacZ::T7 gene1) in chromosomal lac operon (no phage λDE3).

This host has no significant background in the CDNB assay and was used to test numerous (constitutively and DON induced candidate GST genes (from barley, rice, Brachypodium and wheat), most of which showed clear activity with CDNB but no activity above background with DON.

Example 2

Cloning and -Expression of GST Candidates:

Candidates were cloned into *E. coli* expression vector pCA02 that encodes for an N-terminal 6× His tag and maltose binding domain. The vector carries a ColE1 origin, an ampicillin marker, a copy of the lac repressor and a T7 promoter and lac operator sequence.

The empty vector pCA02 was used as negative control. Cloning of TrGST-C02:

Wheat Glutathione S-Transferase TRIAE_CS42_1DL_TGACv1_062916_AA0221650 was amplified from genomic DNA of Chinese Spring Wheat with primers TrGST-C02_upstr_fw and TrGST-C02_3'UTR_rv and cloned into pMiniT (NEB® PCR Cloning Kit). Exon 1 was amplified with primers TrGST-C02_GA-E1-fw and TrGST-C02_GA-E1-rv, exon 2 was amplified with primers TrGST-C02_GA-E2-fw and TrGST-C02_GA-E2-rv from the pMiniT clone. A fusion PCR was done with primers TrGST-C02_GA-E1-fw and TrGST-C02_GA-E2-rv. The PCR product was digest with NdeI/EcoRI and ligated into pCA02 digested with the same enzymes.

Cloning of TrGST-C12:

Wheat Glutathione S-Transferase TRIAE_CS42_1AL_TGACv1_001900_AA0036420 was amplified from genomic DNA of Chinese Spring Wheat with primers TrGST-C12_5'UTR_fw and TrGST-C12_3'UTR_rv and cloned into pMiniT. Exon 1 was amplified with primers TrGST-C12_GA-E1_fw and TrGST-C12_GA-E1_rv, exon 2 was amplified with primers TrGST-C12_GA-E2_fw and TrGST-C12_GA-E2_rv from the pMiniT clone. Gibson assembly was done with NdeI/EcoRI digested pCA02) and both PCR products.

TABLE 2

Primer sequences for cloning of TrGST-C02 % TrGST-C12

| Primer name | Primer sequence | Purpose |
|---|---|---|
| *Primer for cloning of Triticum aestivum GST candidate gene 2* | | |
| TrGST-C02_upstr_fw | CCGGACAAAATGGGGTCG (SEQ ID NO. 41) | Nested PCR with TRIAE_CS42_1DL_TGACv1_062916_AA0221650 |
| TrGST-C02_3'UTR_rv | TTATTCAATGGAAGTCACGTC (SEQ ID NO. 42) | |
| TrGST-C02_GA-E1-fw | aatctctacttccaaggccatATGGCCGGAGGAGATGAC (SEQ ID NO. 43) | Gibson Assembly of TRIAE_CS42_1DL_TGACv1_062916_AA0221650 (exon 1) |
| TrGST-C02_GA-E1-rv | gggcgacgagCTTATCGTCAACGTAGGCG (SEQ ID NO. 44) | |
| TrGST-C02_GA-E2-fw | tgacgataagCTCGTCGCCCCATGGGTA (SEQ ID NO. 45) | Gibson Assembly of TRIAE_CS42_1DL_TGACv1_062916_AA0221650 (exon 2) |

TABLE 2-continued

Primer sequences for cloning of TrGST-C02 % TrGST-C12

| Primer name | Primer sequence | Purpose |
|---|---|---|
| TrGST-C02_GA-E2-rv | aagcttgtcgacggagctcgaattcTTACTTGGTCTCTGAAGCAGCG (SEQ ID NO. 46) | |
| *Primer for cloning of Triticum aestivum GST candidate gene 12* | | |
| TrGST-C12_5'UTR_fw | CCTTACACACACAGATCTAGATG (SEQ ID NO. 47) | Nested PCR with TRIAE_CS42_1AL_TGACv1_001900_AA0036420 |
| TrGST-C12_3'UTR_rv | CAAGAACAGAAATACGGATTTCC (SEQ ID NO. 48) | |
| TrGST-C12_GA-E1_fw | same as TrGST-C02_GA-E1-fw (SEQ ID NO. 44) | Gibson Assembly of TRIAE_CS42_1AL_TGACv1_001900_AA0036420 (exon 1) |
| TrGST-C12_GA-E1_rv | GGGTGACGAGCTTATCGTCAATGTAGGCGG (SEQ ID NO. 49) | |
| TrGST-C12_GA-E2_fw | TGACGATAAGCTCGTCACCCCATGGGTA (SEQ ID NO. 50) | Gibson Assembly of TRIAE_CS42_1AL_TGACv1_001900_AA0036420 (exon 2) |
| TrGST-C12_GA-E2_rv | aagcttgtcgacggagctcgaattcTACTTGGTCTCCGAAGCAGC (SEQ ID NO. 51) | |

TABLE 3

| ID | Source | Accession (http://plants.ensembl.org/Triticum_aestivum/Info/Index)/ Reference | GST class | DON-epoxide conjugation activity |
|---|---|---|---|---|
| TrGST-C01 | Wheat | TRIAE_CS42_1AL_TGACv1_000725_AA0017970 | Tau | – |
| TrGST-C02 | Wheat | TRIAE_CS42_1DL_TGACv1_062916_AA0221650 | Tau | + |
| TrGST-C03 | Wheat | TRIAE_CS42_2DS_TGACv1_179797_AA060924 | Phi | – |
| TrGST-C04 | Wheat | TRIAE_CS42_6AL_TGACv1_473438_AA1531100 | Phi | – |
| TrGST-C06 | Wheat | TRIAE_CS42_5BL_TGACv1_405971_AA1338410 | Tau | – |
| TrGST-C07 | Wheat | TRIAE_CS42_7DL_TGACv1_603073_AA1975180 | Phi | – |
| TrGST-C08 | Wheat | Traes_1AL_1A9EB2CBB | Tau | – |
| TrGST-C09 | Wheat | TRIAE_CS42_1AL_TGACv1_003203_AA0048670 | Tau | – |
| TrGST-C11 | Wheat | TRIAE_CS42_1AL_TGACv1_003384_AA0049460 | Tau | – |
| TrGST-C12 | Wheat | TRIAE_CS42_1AL_TGACv1_001900_AA0036420 | Tau | + |
| TrGST-C15 | Wheat | TRIAE_CS42_1AL_TGACv1_000725_AA0017980 | Tau | – |
| HvGST15264 | Barley | Gardiner SA. et al., Molecular Plant-Microbe Interactions 23 (7): 962-976 | Tau | – |
| HvGST07634 | Barley | Gardiner SA. et al., Molecular Plant-Microbe Interactions 23 (7): 962-976 | Tau | – |
| HvGST07171 | Barley | Gardiner SA. et al., Molecular Plant-Microbe Interactions 23 (7): 962-976 | Tau | – |
| HvGST21968 | Barley | Gardiner SA. et al., Molecular Plant-Microbe Interactions 23 (7): 962-976 | Tau | – |
| HvGST12776 | Barley | Gardiner SA. et al., Molecular Plant-Microbe Interactions 23 (7): 962-976 | Tau | – |

The nucleotide and amino acid sequences of the expressed GSTs used herein are as follows:

TrGST-C01

(SEQ ID NO. 13)

ATTCTCCGCTTATGTCGGTGTTAATAAAGCAGTGA

CGGAGGTGGAGAGGATGGAGAAGGTTAGCGAGACG

CTTGCGGTGCTAGAGCAACTTGAGGAGGCATTTGC

CAAGCATTCCAACGGAAAGGGCTTCTTCGCCGGGG

ACTCCATCGGGTACCTTGACCTCGCAGTAGGATGC

CACTTGCACTGGCTCAAGGCGCAGTGTAAGATGTT

CGGCGTGGTGTTCCTCGACGCCGGCAAGACTCCGC

TCTTAGCGACCTGGGCGAAACGGTTCACTGAGACC

GATGCGGCGAAGGAGGTGGTACCTGACACAGACGT

GGTGATGGAGTATGCTAAGAAGCGCCAGGCTTATC

GTGTTGCTGTTGCTGCGGCGGCAGCGAGTGCCAAG

TGA (SEQ ID NO. 14)

MAAQGDLKLLGLSVSPFVVRVRMALHMKGLSYEYI

KRDLFNKSELLLKSNPVEKKVPILIHDGKTVLDSS

VIVQYIDEVWAAMGPSILPVDPYERATAPFWAAYV

DDKLFSAYVGVNKAVTEVERMEKVSETLAVLEQLE

EAFAKHSNGKGFFAGDSIGYLDLAVGCHLHWLKAQ

CKMFGVVFLDAGKTPLLATWAKRFTETDAAKEVVP

DTDVVMEYAKKRQAYRVAVAAAAASAK

TrGST-C02:

SEQ ID NO. 1, SEQ ID NO. 2

TrGST-C03

(SEQ ID NO. 15)

ATGGCGCCGGTGAAGGTGTTCGGGCAGGCCATGTC

GCCGAACGTGGCGCGGGTGCTGGTGTTCCTGGAGG

AGGCCGGCGCCGACTACGAGCTCGTCGACGTCGAC

TTCCAGGCCAAGGAGCACAAGAGCCCCGACCACCT

TGCCAGAAACCCGTTCGGGCAAATCCCCGCGTTCC

AGGACGGTGACCTCGTTCTCTTCGAGTCACGAGCG

GTCGCAAAGTACGTGGCGCGCAAGTACAAGACGGA

CGAGGCCGACCTGCTGAGGGACGGCGACCATTCAG

AAGCCGCCATGGTGGACGTGTGGACGGAGGTGGAG

GCGCACACGTACAGCGCGGCCCTCTCGCCGATCGT

CTACGAGTGTCTCATCTTCCCTCTCATGCACGGCA

AGCCCACCGACGAGAAGGTCGTCGACGAGAGCCTC

GGGAAGCTGAGGAAAGTGCTCGAGGTCTATGAGGA

GCGGCTGTCCAAGCACAGGTACCTGGCCGGGGATT

TCCTCAGCTTCGCCGACCTCAACCATTTCCCCTAC

ACCTTCTACTTCATGGCGACGCCGCATGGGGCCCT

GTTTGAGTCGTACCCGCGCGTGAAGGCGTGGTGGG

AGAGCATCATGTCCAGGCCGGCGATTCAGAAGCTC

AGTGCAACCATGACACCATGA (SEQ ID NO. 16)

MAPVKVFGQAMSPNVARVLVFLEEAGADYELVDVD

FQAKEHKSPDHLARNPFGQIPAFQDGDLVLFESRA

VAKYVARKYKTDEADLLRDGDHSEAAMVDVWTEVE

AHTYSAALSPIVYECLIFPLMHGKPTDEKVVDESL

GKLRKVLEVYEERLSKHRYLAGDFLSFADLNHFPY

TFYFMATPHGALFESYPRVKAWWESIMSRPAIQKL

SATMTP

TrGST-C04

(SEQ ID NO. 17)

ATGTCTCCGGTGAAGGTGTTCGGGCACCCGATGTT

GACAAACGTCGCACGGGTGCTGCTCTTCCTGGAGG

AGGTCGGCGCTGAGTACGAGCTCGTGCCCCTCGAC

TTCGTAGCCGGCGAGCACAAGAGGCCCCAACACGT

CCAGTTAAACCCGTTTGCGAAGATGCCTGGGTTCC

AAGATGGGGATCTCGTCCTGTTCGAGTCGCGCGCC

ATCGCCAAGTACATCCTCCGCAAGTACGGGGGGAC

AGCCGGCCTGGACCTCCTCGGAGAAAACAGTGGAA

TCGAAGAATTAGCAATGGTGGACATGTGGACGGAG

GTGGAGGCCCAGCAGTACTACCCAGCCATCTCGCC

GGTGGTGTTCGAGTGCATCATCATTCCCTTCATCA

TCCCTGGCGGTGGCGCGGCGCCGAACCGGAGCGTC

GTGGACGAGAGCCTGGAGCGGCTGAGGGGTGTACT

GGGGATCTACGAGGCCCGGCTGGAGAAGAGCAGCT

ACTTGGCCGGGGACTCCATCAGCTTCGCCGATCTG

AACCACATCCCGTTCACCTTCTACTTCATGACCAC

CCCGTACGCCAAGGTGTTTGATGAGTACCCCAAGG

TGAAGGCCTGGTGGGAGATGCTCATGGCCAGGCCG

GCGGTGCAGAGGGTCTGCAAGCATATGCCTACCAA

GTTTAAGCTAGGTGCGCAGTACTAG (SEQ ID NO. 18)

MSPVKVFGHPMLTNVARVLLFLEEVGAEYELVPLD

FVAGEHKRPQHVQLNPFAKMPGFQDGDLVLFESRA

IAKYILRKYGGTAGLDLLGENSGIEELAMVDMVVT

EVEAQQYYPAISPVVFECIIIPFIIPGGGAAPNRS

VVDESLERLRGVLGIYEARLEKSSYLAGDSISFAD

LNHIPFTFYFMTTPYAKVFDEYPKVKAWWEMLMA

RPAVQRVCKHMPTKFKLGAQY

TrGST-C06

-continued (SEQ ID NO. 19)
ATGGCGGGCGAGAAGGGTCTGGTGCTGCTGAACTT

CTGGGTGAGCCCGTTCGGGCAGCGCTGCCTCATCG

CTCTTGCAGAAAAAGGCCTCCCCTACGAGTACGTC

GAAGAGAACCTCATGGCCGGCAAGAGCGACCGCCT

CCTCCGCTCCAACCCCATCCACAAGAAGATCCCAG

TGCTCCTCCACGACGGCCGCCCCGTCAACGAGTCT

CTCATCATCCTCAACTACCTCGACGACGCCTTCCC

GGACACCCCGTCCCTCCTCCCCCTCCGACCCCTACG

AGCGCTCGCAGGCTCGCTTCTGGGCCGACTACGTC

GACAAGAAGGTCTACGACTGCGGCACCCGGCTCTG

GAAGCTCAAGGGCGAGCCGCACGCGCAGGCGCGGG

CCGAGATGGTGGAAATCCTCAAGAATCTGGACGGG

GCGCTCGGGGATAAGTCCTTCTTCGGCGGCGATGC

CTTCGGGGTTCGTCGACGCCGCGTTCGCGCCCTTCA

CGTCGTGGTTCCACAGCTACGAGAAGTACGGCGAG

TTCAGCGTGGCGGAGGTGGCGCCGAAGATCGCGGC

GTGGGCAAAGCGGTGCGGCGAGCGGGAGAGCGTCG

CCAAGAGCCTCTACTCGCCTGACAAGATTTACGAG

TTCATCGGCGTGCTCAAGAAGATGCACGGCGTCGA

GTAA (SEQ ID NO. 20)
MAGEKGLVLLNFWVSPFGQRCLIALAEKGLPYEYV

EENLMAGKSDRLLRSNPIHKKIPVLLHDGRPVNES

LIILNYLDDAFPDTPSLLPSDPYERSQARFWADYV

DKKVYDCGTRLWKLKGEPHAQARAEMVEILKNLDG

ALGDKSFFGGDAFGFVDAAFAPFTSWFHSYEKYGE

FSVAEVAPKIAAWAKRCGERESVAKSLYSPDKIYE

FIGVLKKMHGVE

TrGST-C07
(SEQ ID NO. 21)
ATGGGGACGGAGGCGAAAGTGAAGGTGTTCGGGCC

GGCGAGATCCACCTGCGTGGCGCGGGTGCTGGTGT

GCCTGGAAGAGGTCGGCGCCGAGTACGAGCTGGTG

CACGTCCACCTCCCCGCCGGCGAGCACAAGGGCCC

CGCGCATCTCGCCCGCACCCTCTTTGGCCAGGTCC

CGGCTTTCCAGGACGGTGATCTCATCCTTTTCGAG

TCGCGCGCGATTTCGAGGTACGTGCTCCGCAAAGG

CGCATCCGATCTACTCCGAGAAAACAGCCTCGCCG

AGTCGGCGACGGTGGACGCGTGGCTCGAAGCTGAG

TCCCACAACTTCGACAGGGCCATGTCGGCGATCAC

CTTCCAGTGCTTCGTCGTGCCCATGTTCATGGGCG

GGACGACTGACCACAAAATCGTCGAGGAGAACCTG

-continued

GAGAAGCTTAAGGCGGCCCTCGGAGTCTACGAGGA

GCGTCTGACCAGGTTCAAATACTTGGCCGGAGATT

TCATCAGCCTGGCGGACCTGAGCCATTGCCCCATG

GCTCACTACCTGCTGGCCAGCCCCTGCGCGTCGGT

GCTCGATGCGTATCCGCGTGTGAAGGACTGGGTTG

ATGGGATGATGGATCGACCGAGCGTGAAAAAGGTC

ATGGAGCTTATGGATGCGTCATGA (SEQ ID NO. 22)
MSPVKVFGHPMLTNVARVLLFLEEVGAEYELVPLD

FVAGEHKRPQHVQLNPFAKMPGFQDGDLVLFESRA

IAKYILRKYGGTAGLDLLGENSGIEELAMVDMVVT

EVEAQQYYPAISPVVFECIIIPFIIPGGGAAPNRS

VVDESLERLRGVLGIYEARLEKSSYLAGDSISFAD

LNHIPFTFYFMTTPYAKVFDEYPKVKAVVWEMLMA

RPAVQRVCKHMPTKFKLGAQY

TrGST-C08
(SEQ ID NO. 23)
ATGACGCATCGATCTTTTATATATTCCGCACTCCA

CACTAACCACAGAATCCCACGGAACCTTCAGGCAC

ACCCACGGCAGAAAATGGCCAACGGAGGAGACGAG

CTGAAGCTGCTGGGCATGTGGGCGAGCCCATACGT

GGTCAGGGTGCAGCTCGCGCTCCACCTCAAGGGCG

TGAGCTACGAGTACGTCGAGGAGGACCTCGCCAGC

AAGAGCGAGCTCTTCCTCCGCTCCAACCCGGTGCA

CAAGACAGTCCCGATCCTCATCCACAACGGCAAGC

CCGTCTGCGAGTCCCAGGTCATCCTCCAGTACATC

GACGAGGCCTTCGCCGGCGTCGGCCCGCCCCTCCT

CCCCGCTGACCCCTACGAGCGCGCCGTCGCGCGAT

TCTGGGCCGCCTACGTCGAGGACAAGCTGCTGGCG

CCGTGGGGGAAGGTGTTCAGGGTGAAGACCGACGA

GGAGAGGGCCGAGTGGACGAGGCAGACGGCGGCGG

CGCTGGGTCCTCTGGAGGATGGCCTCAGGGAGTGC

TCCAAGGGGAAGGGCTTCTTCGGCGGCGACTGCGT

CGGGTACGTTGACGTCCTGCTCGGCAGCATGGTGC

CGTGGGTGCGCGCCACCGAGAGGCTCTCCGGCGAC

AAGTTAATAGACGCCGGCAAGGCCCCGCTGCTGGC

GGCATGGATGGAGCGCATTAGCGAGCTCGACGCCG

CCAAGGCGGTCTTCCAGGACGTCGACAGGGTGGTT

GAGTACGCCGGGGCAATACAGGCCCGGCTTTCCGC

CGCGGCTGCTGCAAGCACCCAATAA

-continued (SEQ ID NO. 24)
MTHRSFIYSALHTNHRIPRNLQAHPRQKMANGGDE

LKLLGMWASPYVVRVQLALHLKGVSYEYVEEDLAS

KSELFLRSNPVHKTVPILIHNGKPVCESQVILQYI

DEAFAGVGPPLLPADPYERAVARFWAAYVEDKLLA

PWGKVFRVKTDEERAEVVTRQTAAALGPLEDGLRE

CSKGKGFFGGDCVGYVDVLLGSMVPWVRATERLSG

DKLIDAGKAPLLAAWMERISELDAAKAVFQDVDRV

VEYAGAIQARLSAAAAASTQ

TrGST-C09
(SEQ ID NO. 25)
ATGTCGTCGGGGAAGCAGGAGACGGCGGCGGTGCG

CGTGCTGGGCAGGTGGCCGAGCCCGTTCGTGATCC

GGGTGCTGATAGCTCTTGGGCTCAAGGGCGTGGAC

CACGAGCTCGTGGAGGAGGCGGCGGGCAACAAGAG

CGAGCTGCTGCTCGCCTCCAACCCCGTGCACAAGA

AGATCCCCGTGCTCCTGCACCACGGCAGGCCCGTC

TCCGAGTCCCTCATCATCGTCCAGTACGTCGACGA

GGCCTGGGCCTCCCAAGCCCCGGCGCTCATCCCGT

CCGACCCCTACGCCCGCGCGGCCGAGCGGTTCTGG

GCCCAGTACGTCGACGACAAGTTTCCTACGGCGAT

CCGGGTCCTGAGGGGAAGGCTGGACGGAGACAAGG

AAGAAGCGGCGGCTCAGGTGTGCGCCGCTCTGCAG

CACCTGGAGGTGGCCTTCGTCGAGTGCGGCCAAGG

GAAGGATTACTTCGGCGGCGACGGCGTCGGTTACC

TGGACATTGCTCTCGGGTCGCACCTCGGATGGGTC

AGGGCGGTAGAGAGGATCGCTGAAATCAGGCTGCT

CGACGCGGCCAAGGTTCCTAAGCTGGCGGCGTGGG

CGGATCGGTTCTGCGCCCACCCGGCGGTGGCGAAC

GCCATGCCTAACGTGGACAGGTTCGTGGAGTTCAG

CGTCAAGAATGACGGCGTTCTGAAGGCGGCTAGTG

CTAATTCCAAGTGA (SEQ ID NO. 26)
MSSGKQETAAVRVLGRWPSPFVIRVLIALGLKGVD

HELVEEAAGNKSELLLASNPVHKKIPVLLHHGRPV

SESLIIVQYVDEAWASQAPALIPSDPYARAAERFW

AQYVDDKFPTAIRVLRGRLDGDKEEAAAQVCAALQ

HLEVAFVECGQGKDYFGGDVGYLDIALGSHLGVV

-continued
VRAVERIAEIRLLDAAKVPKLAAWADRFCAHPAVA

NAMPNVDRFVEFSVKNDGVLKAASANSK

TrGST-C11
(SEQ ID NO. 27)
ATGGCCGGAGCAGCAAACGATCTGAAGCTACTGGG

CATGTGGGCGAGCCCGTACGTCCTGCGGGTGCGCC

TTGCTCTCAGCATCAAGAGCATCAGCTACGAGTAC

GCAGAGGAGGACCTCCGGCACAAGAGCGAGCTGCT

CCTGCGGTCAAACCCCGTCCACAACAAGGTCCCCG

TGCTGATCCACGCCGGCAAGCCCGTCTGCGAGTCG

CTGGTCATCCTACAGTACATCGACGACGCTTTCGG

CGGTGCCGGCCCCGCCCTCCTCCCGGCCGATCCCC

ACGAGCGCGCCGTCGCCCGGTTCTGGGCCGCCTTC

ATCGAGGACACGCTCGTGAAGGCGATGAACCAGGC

GTCATGGAGCAAGACGGAGGCGGAGAAGGTGGAGG

GGAACAAACGGGCGACTGCTGCGTTGAACACCCTG

GAGGCGGCCCTGAGGGATGTCTCCAAGGGGAAGCC

CTTCTTCGGGGGCGACAGCACCGGGTATGTGGACA

TCGTGCTCGGCGGCCTCCTCGCGGGGGTGCGCGCC

ATGGAGGCGATGCCGGGCGTCAAGGCCTTCGACCC

CGTCACGATGCCGCTCCTGGCCGCGTGGGCGGACC

ACTTCGGCGCGCTGGACGCGGTGGCGGCCGTGATG

CCGGACGTGAGCAAGCTCGTGGAGCTCTTCATCAC

GATGCACGCTGCTGTTGCGGCAAACTAA (SEQ ID NO. 28)
MAGAANDLKLLGMWASPYVLRVRLALSIKSISYEY

AEEDLRHKSELLLRSNPVHNKVPVLIHAGKPVCES

LVILQYIDDAFGGAGPALLPADPHERAVARFWAAF

IEDTLVKAMNQASWSKTEAEKVEGNKRATAALNTL

EAALRDVSKGKPFFGGDSTGYVDIVLGGLLAGVRA

MEAMPGVKAFDPVTMPLLAAWADHFGALDAVAAVM

PDVSKLVELFITMHAAVAAN

TrGST-C12:
SEQ ID NO. 3, SEQ ID NO. 4

TrGST-C15
(SEQ ID NO. 29)
ATGACGCACGGAGGTATACAAACAAATGTGAAGAA

TACGGTGTCTATCAGTGTTGCACTGATAGAGCAGG

GGAGAAAAAAAAGACGGCGAACGAAACAATGGCA

GCCGAAGGAGGTCTGAAGCTGCTCGGCTTGACGGT

GAGCCCGTTCGTGATCCGTGTACGCATGGCGCTGC

AGATGAAAGGCGTCGGCTACGAGTACGTGGAGCAG

GACCTGTTCACCAAGGGCGAGCTCCTCCGCAAGTC

CAACCCGGTGCACATGAAGGTCCCGGTGCTCATCC

-continued

ACGACGGCAGACCCGTCTGCGAGTCGCTGGCCATC

GTGCAGTACGTCGACGAGGCCTGGGCGGCCGCGGG

CCCCTCGATCCTCCCCGCCGACCCCTACGACCGCG

CCGCCGCTCGCTTCTGGGCCGCCTACGCCGACAGC

AAGCTCTTGCCGGCGTGGGTAGGCATCATGTGGGC

GGAGACGGAGGAGGAGAGGGCGGAGAAGGTCGGCG

ACACGCTCGCGGCTATCGGCCAGTTGGAGGAGGCG

TTCGGGACGTGCTCGAACGGTAAGGCCTTCTTCGC

CGGCGACTCCGTCGGGTACCTAGATCTCGTCGTCG

GCTCGCAGTTGCTCTGGTTCGAGGTGCTGCGGAAG

ATGTTCGGCGTCGTGGTCGTTGAGGTCGGCAGGGC

TCTGCTCTTGGCCGCGTGGGTGGAGCGGTTTGGGG

AGACTGATACGGCCAAGGAGGTGGTGCCGGACGTT

GACACGGCGGTGGAGTACCTCAAGAAGCTTCAGTC

TCGCCGGGCTGGTTCCACGGTTGCCCAGCTGCTGT

CGTGA (SEQ ID NO. 30)
MTHGGIQTNVKNTVSISVALIEQGRKKKTANETMA

AEGGLKLLGLTVSPFVIRVRMALQMKGVGYEYVEQ

DLFTKGELLRKSNPVHMKVPVLIHDGRPVCESLAI

VQYVDEAWAAAGPSILPADPYDRAAARFWAAYADS

KLLPAWVGIMWAETEEERAEKVGDTLAAIGQLEEA

FGTCSNGKAFFAGDSVGYLDLVVGSQLLWFEVLRK

MFGVVVVEVGRALLLAAWVERFGETDTAKEVVPDV

DTAVEYLKKLQSRRAGSTVAQLLS

HvGST15264

(SEQ ID NO. 31)
ATGTCGCAGCAGCCAGAACAGGCGCCGGTGAGGCT

CATCACGGCGTTCGGCAGCCCGTTCGCGCACCGGG

TGGAGGTGGCGCTCACGCTCAAGGGGGTGCCGTAC

GAGCTGCTCGTGGAGGACCTGGCCAGCAAGAGCGA

CCTGCTGCTCGCCCACAACCCCGTCTACCAGTCGG

TCCCCGTCCTCCTCCACGGCGACCGCGCCGTCTGC

GACTCCCTCGTCATCGTCGAGTACGTCGACGAGGC

CTTCCACGACGACGACGGGACGGCGCCCCGGCGCC

TCCTCCCGGCGGACCCCTACGACCGCGCCACCGCC

CGCTTCTGGGCCGACTTCGTCGCCAACAAGTGCTT

GAAGCCGCTGTGGCAGTCGACGTGGACCGACGGCG

AGGAGCAGGCGCGGCTGGCGAGGGAGACCAAGGAG

GGACTGGGGGTACTGGAGGCACAGCTCGACGGGAA

GCGGTTCTTTGGGGGCGAGGCCCTCGGCTTCGTCG

ACCTCGCCGCCTGCACGCTGGCTCACTGGCTCGGC

-continued

GTGCTGGGGGAAGTCGGCGGGGTGCGGCTGATGGA

GGACGGCGAGTACCCTGCTCTCCGCCGGTGGGCCA

AGGAGTACACTTCCCATGAGGTCGTCAGGCGGTCC

CTGCCGGACAGGGACGAGCTCGTCGCCTACTTCAC

CAAAAACAAGGAGAAGTACCGGTCGTCGATGCTCA

AGCCAGCGGTGAAGTGA (SEQ ID NO. 32)
MSQQPEQAPVRLITAFGSPFAHRVEVALTLKGVPY

ELLVEDLASKSDLLLAHNPVYQSVPVLLHGDRAVC

DSLVIVEYVDEAFHDDDGTAPRRLLPADPYDRATA

RFWADFVANKCLKPLWQSTVVTDGEEQARLARETK

EGLGVLEAQLDGKRFFGGEALGFVDLAACTLAHWL

GVLGEVGGVRLMEDGEYPALRRWAKEYTSHEVVRR

SLPDRDELVAYFTKNKEKYRSSMLKPAVK

HvGST07634

(SEQ ID NO. 33)
ATGGATCATCAAGAGGAGAAGGTGAAGCTTTTTGG

CATGTGGGCGAGCCCCTACGTCCTCAAGGTGAAAT

GGGCGCTGAGCATCAAGGGCGTGGAGTACGAGTAC

CTGGAGGAGGACCTGAGGAACAAGAGCGACGATCT

CCTGGAACACAACCCCGTGCACAAGAAGGTCCCCG

TGCTGCTCTACCACGGCAAGCCGGTGGCAGAGTCC

GACGTCATCGTCGAGTTCGTCGACGAGGCGTGGAG

CCACCGAGGCGGCCGCATCCTCCCCGGCGACCCCT

ACGAGCGCGCCATGGCTCGTTTCTGGGTGAGGTTT

GTGCACGACAAGCTCTCGCCGCCGATTTGGAAGTG

GTTCACGACGGCGCCAGGCGAGGACCAGGAGGCCG

CGCGGGGGGCCTCCGTTGAGCAGCTGCAGGTCCTG

GAGGAGTTGCTCGCCGTCGGCGGGAAGGAGTTCTT

CGCCGGGGAGAGCGTTGGGCTCGTGGACCTGTCGC

TCGGCGCGATGGCGTACGTGGTCCCGATGTACGAG

GAGATCGTCGGCGTGAGGCTGGTCACCGAGGAGAG

GTTTCCGTCTCTGTCGGCGTGGATGGGGCGGTTCT

TGGGCTCGCCGCCGGTGAAGGATCACCCGCCGCCA

GTGGAGAGGCTGATACCCAGGTACCGAGCCATGCG

CGAAGCCTTTCTGAAGATGGGCTAG (SEQ ID NO. 34)
MDHQEEKVKLFGMWASPYVLKVKWALSIKGVEYEY

LEEDLRNKSDDLLEHNPVHKKVPVLLYNGKPVAES

DVIVEFVDEAWSHRGGRILPGDPYERAMARFWVR

FVHDKLSPPIWKWFTTAPGEDQEAARGASVEQLQV

LEELLAVGGKEFFAGESVGLVDLSLGAMAYVVPMY

-continued

EEIVGVRLVTEERFPSLSAWMGRFLGSPPVKDHPP

PVERLIPRYRAMREAFLKMG

HvGST07171

(SEQ ID NO. 35)

ATGGCACTGCAGATGAAACGCGTGGGCTACGAGTA

CATGGAGCAGGACCTGTTCACCAAGGGCGAGCTCC

TCCTCAAGTCCAACCCGGTGCACATGAAGGTCCCG

GTGCTCATCCACGACGGCAAATCCATCTGCGAGTC

GCTGGCCATCGTGCAGTACGTCGACGAGGTCTGGG

CCGCCACGGGCACCTCCATCCTCCCCGCCGACCCC

TACGACCGCGCCGCCGCTCGCTTCTGGGCCGCCTA

CGCCGACAGCAAGCTCTTGCCTGCGTGGGTGGGCA

TCATGTGGGCGGCGACGGAGGAGGAGAGAGCGGAG

AAGGTCGGCGACACGCTCGCGGCTATCGGCCAACT

GGAGGAGGCGTTCGGAAAGTGCTCCAACGGAAAGC

CCTTCTTCGCCGGCGATTCCGTCGGCTACCTCGAT

CTCGTCGTCGGTTCGCAGTTGCTCTGGTTCGAGGT

GCTGCGGAAGATGTTCGGCGTCGTGGTCATTGAGG

CCTGCAGGGCTCCCTTCTTGGCCGCGTGGGTGAAG

CGGTTTTGGGAGACTGATACGGCGAAGGCGGTGGT

GCCGGACGTTGGCACGGCGGCGGAGTACCTGAAGA

AGCTTCAGTCTCATCGGGCTGGTGCCACGGTTGCC

CAGTTGCTGTCGTGA (SEQ ID NO. 36)

MALQMKRVGYEYMEQDLFTKGELLLKSNPVHMKVP

VLIHDGKSICESLAIVQYVDEVWAATGTSILPADP

YDRAAARFWAAYADSKLLPAWVGIMWAATEEERAE

KVGDTLAAIGQLEEAFGKCSNGKPFFAGDSVGYLD

LVVGSQLLWFEVLRKMFGVVVIEACRAPPFLAAVVV

KRFWETDTAKAVVPDVGTAAEYLKKLQSHRAGATV

AQLLS

HvGST21968

(SEQ ID NO. 37)

GAGGCTGCAAAGAAGGCGGCGCCACCCATGGAAAG

CATGTTGGAGGAGGCCGAGAAGCTGCGGGCTATGT

GGGCTGCGGCGGCTGCCAAGTAA (SEQ ID NO. 38)

MASEGDDVKVLGTAASMFAIRVRMALHAKGVSYEY

LEQDLFHKGELLLASNPVRKAVPVLIHAGRPVCES

LAIVEYIDEVWAGAASLLPADPYDRAVARFWAAYV

DDKAVPTWIGIMRAATEEDRAERLAAALAAVAPLE

DAFAQCSGGKAFFAGDSIGYVDLALGCNLFWIEAL

RHMFGITVIDAGRTPRLAAWAERFVETEAAKKAAP

PMESMLEEAEKLRAMWAAAAAK

-continued

HvGST12776

(SEQ ID NO. 39)

ATGGCAGGAGGCGGCGAGGGCGAGCTGAAGCTGCT

GGGCGTGTGGACGAGCCCGTTCGTCATCCGGGTGC

GCGTGGTGCTCAACCTCAAGTCGCTGCCGTACGAG

TACGTGGAGGAGAACCTGGGCAGCAAGAGCGCGCT

CCTCCTGGGCTCCAACCCGGTGCACCAGAGCGTGC

CGGTCCTCCTCCACGGCGGCCGCCCCGTGAACGAG

TCCCAGGTCATCGTGCAGTACATCGACGAGGTCTG

GGCGGGGGTCGGCCCGTCGGTGCTCCCGGCCGACC

CCTACGAGCGCGCCGTGGCGCGCTTCTGGGCGGCG

TACGTCGACGACAAGGTCGGGTCGGCGTGGACGGG

GATGCTCTTCTCGTGCAAGACGGAGGAGGAGAGGG

CGGAGGCCGTGTCCCGCGCCGTGGCGGCGCTGGAG

ACCCTGGAGGGCGCGCTCGCGGAGTGCTCCGGGGG

GAAGCCGTTCTTCGGCGGCGACGCCATCGGGTTCG

TCGACGTCGTGCTCGGCGGCTACCTCGGGTGGTTC

GGGGCGATCGACAAGATCATCGGGCGCCGGCTGAT

CGACCCGGCGAGGACGCCGCTGCTGGCCAGGTGGG

AGGAGTGGTTCCGCGCGGCGGACGCGGCCAAGGGC

GTCGTGCCGGACGACGCCGACAAGATGCTCGACTT

CTTGCCCACCCTGCTCGCTTGGATCGCCTCCAAGG

CCAAGTGA (SEQ ID NO. 40)

MAGGGEGELKLLGVVVTSPFVIRVRVVLNLKSLPY

EYVEENLGSKSALLLGSNPVHQSVPVLLHGGRPVN

ESQVIVQYIDEVWAGVGPSVLPADPYERAVARFWA

AYVDDKVGSAVVTGMLFSCKTEEERAEAVSRAVAA

LETLEGALAECSGGKPFFGGDAIGFVDVVLGGYLG

WFGAIDKIIGRRLIDPARTPLLARWEEWFRAADAA

KGVVPDDADKMLDFLPTLLAWIASKAK

Expression was performed in 50 ml Terrific Broth with ampicillin (TB+100 ppm Amp), induced with 1 mM Isopropyl β-d-1-thiogalactopyranoside (IPTG), 20° C. over night. Pellets were washed in 1× Phosphate-buffered saline (PBS: 50 mM sodium phosphate, 150 mM M sodium chloride, pH7) and resuspended in 2.5 ml 100 mM sodium phosphate buffer pH 6, containing 10% glycerine. Cells were disrupted by sonication (Ultrasonic lysis with Brason sonifier W250D: big tip, 40% amplitude, 20 sec total pulse time)

TABLE 4

| Expression of GST candidates and control constructs (OD600 = optical density at 600 nm) | | |
| --- | --- | --- |
| Expressed protein | OD600 | m(Pellet) |
| (T7 Express ΔgstA): TrGST-C08, TB + Amp, 1 mM IPTG | 17.66 | 1.09 g |
| (T7 Express ΔgstA): TrGST-C09, TB + Amp, 1 mM IPTG | 15.9 | 1.06 g |
| (T7 Express ΔgstA): TrGST-C11, TB + Amp, 1 mM IPTG | 18.18 | 1.11 g |
| (T7 Express ΔgstA): TrGST-C12, TB + Amp, 1 mM IPTG | 17.28 | 1.09 g |
| (T7 Express ΔgstA): TrGST-C15, TB + Amp, 1 mM IPTG | 16.38 | 0.97 g |
| (T7 Express ΔgstA): HvGST15264, TB + Amp, 1 mM IPTG | 18.48 | 1.17 g |
| (T7 Express ΔgstA): HvGST07634, TB + Amp, 1 mM IPTG | 18.52 | 1.19 g |
| (T7 Express ΔgstA): HvGST07171, TB + Amp, 1 mM IPTG | 19.24 | 1.17 g |
| (T7 Express ΔgstA): HvGST21968, TB + Amp, 1 mM IPTG | 17.72 | 1.17 g |
| (T7 Express ΔgstA): HvGST12776, TB + Amp, 1 mM IPTG | 20.38 | 1.21 g |
| (T7 Express ΔgstA): pCA02, TB + Amp, 1 mM IPTG | 15.26 | 1.02 g |

Sodium dodecyl sulfate-polyacrylamide gel electrophoresis (SDS PAGE) with 12% polyacrylamide gels was used to assess expression of the 6×HIS-malE-(TEV)-GST fusion proteins. Results are shown in FIG. 4.

2 μl of the samples were diluted with water to 15 μl+5 μl 4×SDS loading dye, incubated for 5 min at 95° C., and centrifuged. 12 μl were loaded (except: 5 μl PageRuler™ Prestained Protein Ladder, ThermoFisher Scientific)

The 6×HIS-tagged proteins were affinity purified by immobilized metal ion affinity chromatography (IMAC) and used for enzymatic assays. For comparison the *Schistosoma japonicum*, which does not produce DON-13-GSH, GST was also purified (It showed about 10× higher specific activity with CDNB, but no activity with the epoxide of DON). This enzyme was expressed from the vector pGEX-4T3 lacking a His Tag sequence and was therefore purified by Glutathione Sepharose 4B affinity chromatography.

SDS-PAGE: (Expected size: TrGST-C02: 69.2 kDa; TrGST-C12: 69.2 kDa; SjGST: 26 kDa). As described above, candidate GSTs were cloned into vector pCA02 and expressed with N-terminal 6× His tag and maltose binding domain FIG. 5 shows an SDS-PAGE, applied concentrations: CE (cell extract) and FT (flow through): 0.75 mg/ml, Protein: 0.23 mg/mL Enzymatic DON-GSH Conjugation Assays and Analytical Measurements:

Final concentrations in Assay: Toxin concentration in assay: 100 ppm DON (1000 ppm DON stock in $H_2O$), 5 mM GSH, 0.1 M sodium phosphate buffer pH6, 7.5% glycerine. Time points: 0, 3, 6, 24 h Orbitrap Assay 20 μl aliquots of samples from the DON-GSH conjugation assay were mixed with 20 μl acetonitrile in an eppendorf tube, and were centrifuged at 20 000 rcf, for 7.5 min. 15 μl supernatant were taken and mixed with 135 μl $H_2O$ in vials to provide in total a 20× dilution, containing 5% acetonitrile and 5 ppm DON in this dilution. The samples were measured within a few hours, and stored at 4° C. until measurement.

For DON detoxification assays HPLC-MS/MS was used. Samples were measured with LC-HRMS(/MS) using a Vanquish system (Thermo Scientific) coupled to a QExactive HF Orbitrap instrument (Thermo Scientific). For this, 5 μL of cooled diluted supernatant (10° C.) were injected for gradient elution on an Atlantis® column (dC18, 3 μm, 2.1×1500 mm, Waters) with 0.3 mL/min flow rate. The two ramp gradient elution (eluent A: $H_2O$+0.1% FA; eluent B: MeOH+0.1% FA) started increasing eluent B from 3 to 20% within 5.5 minutes after one minute of equilibration followed by an increase from 20 to 100% B within 2.5 minutes.

After 1.5 minutes eluting with 100% B the system was reequilibrated for 3.5 minutes (14 minutes total runtime). Mass spectra were recorded with a resolution of 120,000 (at m/z 200) in full scan mode applying fast polarity switching and a scan range from m/z 100 to 1000. MS/MS fragmentation spectra were recorded in positive mode with a resolution of 30,000 (at m/z 200) and stepped collision energy (25, 35, 45) applying a data dependent method using an inclusion list.

In principle two types of adducts of DON with glutathione are formed nonenzymatically. The Michael adduct (to C10) formation takes place within days, and consequently within an observation period of 24 hours a background is visible. Most enzymes do not enhance the formation of the Michael adduct formation above this background (see below). The plasmid pCA02 is the empty expression vector and is clustering with most (inactive) GSTs. The exceptions are the two wheat enzymes C02 and C12 which clearly enhance Michael adduct formation.

Formation of the Michael adduct "MH1" is shown in FIG. 6.

In contrast, the formation of the epoxide adduct ("MH2" with a different retention time) does not happen to a relevant extent within 24 hours. The empty vector and other enzymes tested above do not give a measurable background, while wheat GSTs C02 and C12 clearly catalyze the formation of the epoxide-adduct. (FIG. 8)

The identity of the peaks was determined by comparison with a standard generated by extended incubation of DON and GSH (for several weeks) as described by Stanic et al. (https://www.ncbi.nlm.nih.gov/pubmed/27548277). In contrast to the human GST enzymes tested by these authors, the C02 and C12 clearly catalyze both formation of the Michael adduct and the opening of the epoxide.

A sample chromatogram is shown in FIG. 9 (reaction with wheat GST C02).

Besides the glutathione adducts also products lacking 2 hydrogen atoms in the DON part are formed in lower amounts by the enzyme, which are most likely the GSH adducts of C3-keto derivatives of DON.

Example 3

It was shown that TrGST-C02 and TrGST-C12 can also open the epoxide of Type A and macrocyclic (type D) trichothecenes. The following compounds lack the conjugated C8-keto feature of type B trichothecenes (required for Michael adduct formation), the adduct formation is therefore due to epoxide opening. Calculations of the expected masses of adducts with the respective compounds are given in the following tables.

TABLE 6

| Name | formula | C | H | N | O | S | neutral mass | [M + H]+ |
|---|---|---|---|---|---|---|---|---|
| Tricho-dermin | C17H24O4 | 17 | 24 | | 4 | | 292.1675 | 293.1747 |
| GSH | C10H17N3O6S | 10 | 17 | 3 | 6 | 1 | 307.0838 | 308.0911 |
| TCM-GSH | | 27 | 41 | 3 | 10 | 1 | 599.2513 | 600.2585 |

TABLE 5

| Name | formula | C | H | N | O | S | neutral mass | [M + H]+ |
|---|---|---|---|---|---|---|---|---|
| T-2 | C24H34O9 | 24 | 34 | 0 | 9 | | 466.2203 | 467.2276 |
| GSH | C10H17N3O6S | 10 | 17 | 3 | 6 | 1 | 307.0838 | 308.0911 |
| T-2-GSH | | 34 | 51 | 3 | 15 | 1 | 773.3041 | 774.3114 |

TABLE 7

| Name | formula | C | H | N | O | S | neutral mass | [M + H]+ |
|---|---|---|---|---|---|---|---|---|
| Roridin A | C29H40O9 | 29 | 40 | | 9 | | 532.2672 | 533.2745 |
| GSH | C10H17N3O6S | 10 | 17 | 3 | 6 | 1 | 307.0838 | 308.0911 |
| ROA-GSH | | 39 | 57 | 3 | 15 | 1 | 839.3510 | 840.3403 |

The invention claimed is:

1. A method for biotransformation of a trichothecene by contacting material contaminated with trichothecenes with an exogenous non-animal glutathione-S-transferase (GST) having substrate specificity for the epoxide ring of the trichothecene, comprising incubating components comprising the material, the GST, and glutathione in an aqueous solution at a pH range of 6 to 9 under conditions wherein glutathione reacts with the epoxide moiety, thereby forming an epoxide adduct, wherein:

(i) the GST has at least 95% sequence identity with SEQ ID NO: 2 or SEQ ID NO: 4, or the GST has an amino acid sequence as defined in (i) and is encoded by a polynucleotide sequence having at least 95% sequence identity with SEQ ID NO: 1 or SEQ ID NO: 3.

2. The method according to claim 1, wherein the trichothecene is selected from the group consisting of type A trichothecenes, type B trichothecenes, type C trichothecenes, and type D trichothecenes, optionally the trichothecene is selected from the group consisting of T-2 toxin, HT-2 toxin, neosolaniol, deoxynivalenol (DON), nivalenol (NIV), trichothecin, 3- and 15-acetyldeoxynivalenol, roridin A and verrucarin A.

3. The method according to claim 1, which comprises decontaminating liquid or solid material or material surface, textile material, filter material, gas masks, or air conditioning systems, or purifying material surfaces, or animal or human surfaces.

4. The method according to claim 1, wherein the GST is the recombinant GST, having the amino acid sequence of SEQ ID NO: 4, or having at least 95%, or at least 99% sequence identity with SEQ ID NO: 4 and having substrate specificity for the epoxide ring of the trichothecene.

5. The method according to claim 1, wherein the GST is encoded by the polynucleotide sequence selected from the group consisting of SEQ ID NO: 1, and SEQ ID NO: 3.

6. The method according to claim 1, wherein the GST is expressed in a host cell.

7. A feed additive or feed material comprising a recombinant exogenous non-animal GST which has substrate specificity for the epoxide ring of a trichothecene, wherein said feed additive or feed material is produced by the method according to claim 1.

8. The feed additive or feed material according to claim 7, comprising a transgenic plant part, transgenic plant tissue, transgenic plant cell, seed or progeny thereof, leaf, stem, root, cotyledon, or hypocotyl, each of the foregoing containing an exogenous GST having substrate specificity for the epoxide ring of the trichothecene.

9. The method according to claim 1, wherein: (i) the GST has at least 99% sequence identity with SEQ ID NO: 2 or SEQ ID NO: 4, or the GST has an amino acid sequence as defined in (i) and is encoded by a polynucleotide sequence having at least 99% sequence identity with SEQ ID NO: 1 or SEQ ID NO: 3.

10. The method according to claim 2, wherein the trichothecene is a type B trichothecene.

11. The method according to claim 10, wherein the type B trichothecene comprises deoxynivalenol (DON), nivalenol (NIV), trichothecin, 3-acetyldeoxynivalenol, or 15-acetyldeoxynivalenol.

* * * * *

SEQUENCE LISTING

<160> NUMBER OF SEQ ID NOS: 51

<210> SEQ ID NO 1
<211> LENGTH: 712
<212> TYPE: DNA
<213> ORGANISM: Triticum aestivum

<400> SEQUENCE: 1

```
aatggccgga ggagatgact tgaagctgct gggcgcttgg gcaagtccat ttgtcaccag     60
ggtgaagctt gcgctgaact tcaagggcct gagcttcgag gatgtcgaag aggaccttag    120
caacaagagc gagctcctcc tcagctcgaa cccggtgcac aagaaggtgc ccgtgctcgt    180
ccacaacgga aaacccattt gcgagtcagt gatcatcgtt cagtacatcg atgaggcgtt    240
cgccggcatc ggccccgctc tccttccctc tgacccctac gaacgcgcca ttgcccgttt    300
ctgggccgcc tacgttgacg ataagctcgt cgccccatgg gtacagtcgt tgagggccaa    360
gacagaggag gagaagtccg aggggcttaa gcagacattt gccgcggtgg agacactgga    420
aggagccctg cgggagtgct ccaagggaga gggctacttt ggtggtgaga ccgtcgggct    480
tgtggacatt tcacttggga gcctgctctc ctggttgaac gcgacagaag tgatgtccgg    540
aaccaagata tttgatcctg ttaagactcc gctcctggca gcgtggatgg agcgctttag    600
caagctcgat gctgccaagg cggcgttgcc agaagttgat agggtggtcg aatttgccaa    660
gaagagacaa gcacaggctg ctgccgccgc cgctgcttca gagaccaagt aa            712
```

<210> SEQ ID NO 2
<211> LENGTH: 236
<212> TYPE: PRT
<213> ORGANISM: Triticum aestivum

<400> SEQUENCE: 2

```
Met Ala Gly Gly Asp Asp Leu Lys Leu Leu Gly Ala Trp Ala Ser Pro
1               5                   10                  15

Phe Val Thr Arg Val Lys Leu Ala Leu Asn Phe Lys Gly Leu Ser Phe
            20                  25                  30

Glu Asp Val Glu Glu Asp Leu Ser Asn Lys Ser Glu Leu Leu Leu Ser
        35                  40                  45

Ser Asn Pro Val His Lys Lys Val Pro Val Leu Val His Asn Gly Lys
```

-continued

```
            50              55              60
Pro Ile Cys Glu Ser Val Ile Ile Val Gln Tyr Ile Asp Glu Ala Phe
65              70              75              80

Ala Gly Ile Gly Pro Ala Leu Leu Pro Ser Asp Pro Tyr Glu Arg Ala
                85              90              95

Ile Ala Arg Phe Trp Ala Ala Tyr Val Asp Asp Lys Leu Val Ala Pro
            100             105             110

Trp Val Gln Ser Leu Arg Ala Lys Thr Glu Glu Glu Lys Ser Glu Gly
            115             120             125

Leu Lys Gln Thr Phe Ala Ala Val Glu Thr Leu Glu Gly Ala Leu Arg
        130             135             140

Glu Cys Ser Lys Gly Glu Gly Tyr Phe Gly Gly Glu Thr Val Gly Leu
145             150             155             160

Val Asp Ile Ser Leu Gly Ser Leu Leu Ser Trp Leu Asn Ala Thr Glu
                165             170             175

Val Met Ser Gly Thr Lys Ile Phe Asp Pro Val Lys Thr Pro Leu Leu
                180             185             190

Ala Ala Trp Met Glu Arg Phe Ser Lys Leu Asp Ala Ala Lys Ala Ala
            195             200             205

Leu Pro Glu Val Asp Arg Val Val Glu Phe Ala Lys Lys Arg Gln Ala
        210             215             220

Gln Ala Ala Ala Ala Ala Ala Ser Glu Thr Lys
225             230             235
```

```
<210> SEQ ID NO 3
<211> LENGTH: 708
<212> TYPE: DNA
<213> ORGANISM: Triticum aestivum

<400> SEQUENCE: 3
atggccggag gagatgactt gaagctgctc ggcgcttggg cgagtccatt tgtcgccagg      60
gtgaagcttg cgctgagctt caagggcctg agcttcgagg atgtcgagga ggacctcagc     120
aacaagagcg agctcctcct cagctcgaac ccggtgcaca agaaggtgcc cgtgctcgtc     180
cacaacggga aacccatttg cgagtcaatg atcatcgttc agtacatcga tgaggcgttc     240
cttgtcggcc cctctcttct tccctctgac ccctacaaac gtgcaattgc ccgttttttgg     300 gccgcctaca ttgacgataa gctcgtcacc ccatgggtac agtcgttgag ggccaagaca     360
gaggaggaga gtctgagggg ggttaagcag acatttgccg ctgtggaaac actggaagga     420
gccctgaggg agtgctccaa gggagagggc tactttggtg gtgagaccgt cgggcttgtg     480
gacatttcac ttgggagcct gctctcctgg ttgattgcga cagaagtgat gtctggaacc     540
aagatctttg atcctgttaa gactccgctc ctggcagcgt ggatgggggcg ctttagcgag     600 ctcgacgctg ccaaggcggc gttgccagaa gttgataggg tggtcgaatt tgccaagaag     660
agacaggcac aggctgatgc cgccgccgct gcttcggaga ccaagtaa               708
```

```
<210> SEQ ID NO 4
<211> LENGTH: 235
<212> TYPE: PRT
<213> ORGANISM: Triticum aestivum

<400> SEQUENCE: 4

Met Ala Gly Gly Asp Asp Leu Lys Leu Leu Gly Ala Trp Ala Ser Pro
1               5               10              15

Phe Val Ala Arg Val Lys Leu Ala Leu Ser Phe Lys Gly Leu Ser Phe
```

-continued

```
            20                  25                  30

Glu Asp Val Glu Glu Asp Leu Ser Asn Lys Ser Glu Leu Leu Leu Ser
        35                  40                  45

Ser Asn Pro Val His Lys Lys Val Pro Val Leu Val His Asn Gly Lys
    50                  55                  60

Pro Ile Cys Glu Ser Met Ile Ile Val Gln Tyr Ile Asp Glu Ala Phe
65                  70                  75                  80

Leu Val Gly Pro Ser Leu Leu Pro Ser Asp Pro Tyr Lys Arg Ala Ile
                85                  90                  95

Ala Arg Phe Trp Ala Ala Tyr Ile Asp Asp Lys Leu Val Thr Pro Trp
            100                 105                 110

Val Gln Ser Leu Arg Ala Lys Thr Glu Glu Glu Lys Ser Glu Gly Val
        115                 120                 125

Lys Gln Thr Phe Ala Ala Val Glu Thr Leu Glu Gly Ala Leu Arg Glu
    130                 135                 140

Cys Ser Lys Gly Glu Gly Tyr Phe Gly Gly Glu Thr Val Gly Leu Val
145                 150                 155                 160

Asp Ile Ser Leu Gly Ser Leu Leu Ser Trp Leu Ile Ala Thr Glu Val
                165                 170                 175

Met Ser Gly Thr Lys Ile Phe Asp Pro Val Lys Thr Pro Leu Leu Ala
            180                 185                 190

Ala Trp Met Gly Arg Phe Ser Glu Leu Asp Ala Ala Lys Ala Ala Leu
            195                 200                 205

Pro Glu Val Asp Arg Val Val Glu Phe Ala Lys Lys Arg Gln Ala Gln
    210                 215                 220

Ala Asp Ala Ala Ala Ala Ala Ser Glu Thr Lys
225                 230                 235
```

```
<210> SEQ ID NO 5
<211> LENGTH: 22
<212> TYPE: DNA
<213> ORGANISM: Artificial Sequence
<220> FEATURE:
<223> OTHER INFORMATION: Primer sequence

<400> SEQUENCE: 5
agaagaagct gcaatatgtg aa                                                    22

<210> SEQ ID NO 6
<211> LENGTH: 20
<212> TYPE: DNA
<213> ORGANISM: Artificial Sequence
<220> FEATURE:
<223> OTHER INFORMATION: Primer sequence

<400> SEQUENCE: 6
ttgtaaatct ttgcccgcag                                                       20

<210> SEQ ID NO 7
<211> LENGTH: 20
<212> TYPE: DNA
<213> ORGANISM: Artificial Sequence
<220> FEATURE:
<223> OTHER INFORMATION: Primer Sequence

<400> SEQUENCE: 7
atctggacga agagcatcag                                                       20

<210> SEQ ID NO 8
```

-continued

```
<211> LENGTH: 20
<212> TYPE: DNA
<213> ORGANISM: Artificial Sequence
<220> FEATURE:
<223> OTHER INFORMATION: Primer sequence

<400> SEQUENCE: 8
gcatcagcca tgatggatac                                                20

<210> SEQ ID NO 9
<211> LENGTH: 22
<212> TYPE: DNA
<213> ORGANISM: Artificial Sequence
<220> FEATURE:
<223> OTHER INFORMATION: Primer sequence

<400> SEQUENCE: 9
gctatggcct gcagagcatc gg                                             22

<210> SEQ ID NO 10
<211> LENGTH: 22
<212> TYPE: DNA
<213> ORGANISM: Artificial Sequence
<220> FEATURE:
<223> OTHER INFORMATION: Primer sequence

<400> SEQUENCE: 10
ggttaaacac ctggcgcgag ct                                             22

<210> SEQ ID NO 11
<211> LENGTH: 22
<212> TYPE: DNA
<213> ORGANISM: Artificial Sequence
<220> FEATURE:
<223> OTHER INFORMATION: Primer sequence

<400> SEQUENCE: 11
ccctgccgat gccaaccaag tt                                             22

<210> SEQ ID NO 12
<211> LENGTH: 22
<212> TYPE: DNA
<213> ORGANISM: Artificial Sequence
<220> FEATURE:
<223> OTHER INFORMATION: Primer sequence

<400> SEQUENCE: 12
tggctatctg ggatcggcgg ag                                             22

<210> SEQ ID NO 13
<211> LENGTH: 714
<212> TYPE: DNA
<213> ORGANISM: Triticum aestivum

<400> SEQUENCE: 13
atggcagctc aaggagacct gaagttgcta ggcttgtcgg tgagcccatt cgtagttcgt     60
gttcgcatgg cgctccacat gaagggcttg agctacgagt atatcaaacg ggacctcttc    120
aacaagagtg agctcctcct caagtccaac ccggtggaga agaaggtgcc catactcatc    180
cacgatggca agaccgtact cgattcttcg gtcatcgtgc agtacatcga cgaagtctgg    240
gccgccatgg ggccgtcgat cctccctgtc gacccctacg agcgcgccac cgccccttc    300 tgggccgcct acgtcgacga caaactattc tccgcttatg tcggtgttaa taaagcagtg    360
acggaggtgg agaggatgga gaaggttagc gagacgcttg cggtgctaga gcaacttgag    420
```

```
gaggcatttg ccaagcattc caacggaaag ggcttcttcg ccggggactc catcgggtac        480
cttgacctcg cagtaggatg ccacttgcac tggctcaagg cgcagtgtaa gatgttcggc        540
gtggtgttcc tcgacgccgg caagactccg ctcttagcga cctgggcgaa acggttcact        600
gagaccgatg cggcgaagga ggtggtacct gacacagacg tggtgatgga gtatgctaag        660
aagcgccagg cttatcgtgt tgctgttgct gcggcggcag cgagtgccaa gtga             714
```

```
<210> SEQ ID NO 14
<211> LENGTH: 237
<212> TYPE: PRT
<213> ORGANISM: Triticum aestivum

<400> SEQUENCE: 14

Met Ala Ala Gln Gly Asp Leu Lys Leu Leu Gly Leu Ser Val Ser Pro
1               5                   10                  15

Phe Val Val Arg Val Arg Met Ala Leu His Met Lys Gly Leu Ser Tyr
                20                  25                  30

Glu Tyr Ile Lys Arg Asp Leu Phe Asn Lys Ser Glu Leu Leu Leu Lys
            35                  40                  45

Ser Asn Pro Val Glu Lys Lys Val Pro Ile Leu Ile His Asp Gly Lys
        50                  55                  60

Thr Val Leu Asp Ser Ser Val Ile Val Gln Tyr Ile Asp Glu Val Trp
65                  70                  75                  80

Ala Ala Met Gly Pro Ser Ile Leu Pro Val Asp Pro Tyr Glu Arg Ala
                85                  90                  95

Thr Ala Pro Phe Trp Ala Ala Tyr Val Asp Asp Lys Leu Phe Ser Ala
                100                 105                 110

Tyr Val Gly Val Asn Lys Ala Val Thr Glu Val Glu Arg Met Glu Lys
            115                 120                 125

Val Ser Glu Thr Leu Ala Val Leu Glu Gln Leu Glu Glu Ala Phe Ala
        130                 135                 140

Lys His Ser Asn Gly Lys Gly Phe Phe Ala Gly Asp Ser Ile Gly Tyr
145                 150                 155                 160

Leu Asp Leu Ala Val Gly Cys His Leu His Trp Leu Lys Ala Gln Cys
                165                 170                 175

Lys Met Phe Gly Val Val Phe Leu Asp Ala Gly Lys Thr Pro Leu Leu
                180                 185                 190

Ala Thr Trp Ala Lys Arg Phe Thr Glu Thr Asp Ala Ala Lys Glu Val
            195                 200                 205

Val Pro Asp Thr Asp Val Val Met Glu Tyr Ala Lys Lys Arg Gln Ala
        210                 215                 220

Tyr Arg Val Ala Val Ala Ala Ala Ala Ser Ala Lys
225                 230                 235
```

```
<210> SEQ ID NO 15
<211> LENGTH: 651
<212> TYPE: DNA
<213> ORGANISM: Triticum aestivum

<400> SEQUENCE: 15
atggcgccgg tgaaggtgtt cgggcaggcc atgtcgccga acgtggcgcg ggtgctggtg        60
ttcctggagg aggccggcgc cgactacgag ctcgtcgacg tcgacttcca ggccaaggag       120
cacaagagcc ccgaccacct tgccagaaac ccgttcgggc aaatccccgc gttccaggac       180
ggtgacctcg ttctcttcga gtcacgagcg gtcgcaaagt acgtggcgcg caagtacaag       240
```

-continued

```
acggacgagg ccgacctgct gagggacggc gaccattcag aagccgccat ggtggacgtg    300
tggacggagg tggaggcgca cacgtacagc gcggccctct cgccgatcgt ctacgagtgt    360
ctcatcttcc ctctcatgca cggcaagccc accgacgaga aggtcgtcga cgagagcctc    420
gggaagctga ggaaagtgct cgaggtctat gaggagcggc tgtccaagca caggtacctg    480 gccgggggatt tcctcagctt cgccgacctc aaccatttcc cctacacctt ctacttcatg    540
gcgacgccgc atggggccct gtttgagtcg tacccgcgcg tgaaggcgtg gtgggagagc    600
atcatgtcca ggccggcgat tcagaagctc agtgcaacca tgacaccatg a              651
```

```
<210> SEQ ID NO 16
<211> LENGTH: 216
<212> TYPE: PRT
<213> ORGANISM: Triticum aestivum

<400> SEQUENCE: 16

Met Ala Pro Val Lys Val Phe Gly Gln Ala Met Ser Pro Asn Val Ala
1               5                   10                  15

Arg Val Leu Val Phe Leu Glu Glu Ala Gly Ala Asp Tyr Glu Leu Val
            20                  25                  30

Asp Val Asp Phe Gln Ala Lys Glu His Lys Ser Pro Asp His Leu Ala
        35                  40                  45

Arg Asn Pro Phe Gly Gln Ile Pro Ala Phe Gln Asp Gly Asp Leu Val
    50                  55                  60

Leu Phe Glu Ser Arg Ala Val Ala Lys Tyr Val Ala Arg Lys Tyr Lys
65                  70                  75                  80

Thr Asp Glu Ala Asp Leu Leu Arg Asp Gly Asp His Ser Glu Ala Ala
            85                  90                  95

Met Val Asp Val Trp Thr Glu Val Glu Ala His Thr Tyr Ser Ala Ala
            100                 105                 110

Leu Ser Pro Ile Val Tyr Glu Cys Leu Ile Phe Pro Leu Met His Gly
        115                 120                 125

Lys Pro Thr Asp Glu Lys Val Val Asp Glu Ser Leu Gly Lys Leu Arg
    130                 135                 140

Lys Val Leu Glu Val Tyr Glu Glu Arg Leu Ser Lys His Arg Tyr Leu
145                 150                 155                 160

Ala Gly Asp Phe Leu Ser Phe Ala Asp Leu Asn His Phe Pro Tyr Thr
                165                 170                 175

Phe Tyr Phe Met Ala Thr Pro His Gly Ala Leu Phe Glu Ser Tyr Pro
            180                 185                 190

Arg Val Lys Ala Trp Trp Glu Ser Ile Met Ser Arg Pro Ala Ile Gln
        195                 200                 205

Lys Leu Ser Ala Thr Met Thr Pro
    210                 215
```

```
<210> SEQ ID NO 17
<211> LENGTH: 690
<212> TYPE: DNA
<213> ORGANISM: Triticum aestivum

<400> SEQUENCE: 17
atgtctccgg tgaaggtgtt cgggcacccg atgttgacaa acgtcgcacg ggtgctgctc     60
ttcctggagg aggtcggcgc tgagtacgag ctcgtgcccc tcgacttcgt agccggcgag    120
cacaagaggc cccaacacgt ccagttaaac ccgtttgcga agatgcctgg gttccaagat    180
```

-continued

```
ggggatctcg tcctgttcga gtcgcgcgcc atcgccaagt acatcctccg caagtacggg    240
gggacagccg gcctggacct cctcggagaa aacagtggaa tcgaagaatt agcaatggtg    300
gacatgtgga cggaggtgga ggcccagcag tactacccag ccatctcgcc ggtggtgttc    360
gagtgcatca tcattccctt catcatccct ggcggtggcg cggcgccgaa ccggagcgtc    420
gtggacgaga gcctggagcg gctgaggggt gtactgggga tctacgaggc ccggctggag    480
aagagcagct acttggccgg ggactccatc agcttcgccg atctgaacca catcccgttc    540
accttctact tcatgaccac cccgtacgcc aaggtgtttg atgagtaccc caaggtgaag    600
gcctggtggg agatgctcat ggccaggccg gcggtgcaga gggtctgcaa gcatatgcct    660
accaagttta agctaggtgc gcagtactag    690
```

<210> SEQ ID NO 18
<211> LENGTH: 229
<212> TYPE: PRT
<213> ORGANISM: Triticum aestivum

<400> SEQUENCE: 18

```
Met Ser Pro Val Lys Val Phe Gly His Pro Met Leu Thr Asn Val Ala
1               5                   10                  15

Arg Val Leu Leu Phe Leu Glu Glu Val Gly Ala Glu Tyr Glu Leu Val
            20                  25                  30

Pro Leu Asp Phe Val Ala Gly Glu His Lys Arg Pro Gln His Val Gln
        35                  40                  45

Leu Asn Pro Phe Ala Lys Met Pro Gly Phe Gln Asp Gly Asp Leu Val
        50                  55                  60

Leu Phe Glu Ser Arg Ala Ile Ala Lys Tyr Ile Leu Arg Lys Tyr Gly
65                  70                  75                  80

Gly Thr Ala Gly Leu Asp Leu Leu Gly Glu Asn Ser Gly Ile Glu Glu
                85                  90                  95

Leu Ala Met Val Asp Met Trp Thr Glu Val Glu Ala Gln Gln Tyr Tyr
            100                 105                 110

Pro Ala Ile Ser Pro Val Val Phe Glu Cys Ile Ile Ile Pro Phe Ile
        115                 120                 125

Ile Pro Gly Gly Gly Ala Ala Pro Asn Arg Ser Val Val Asp Glu Ser
    130                 135                 140

Leu Glu Arg Leu Arg Gly Val Leu Gly Ile Tyr Glu Ala Arg Leu Glu
145                 150                 155                 160

Lys Ser Ser Tyr Leu Ala Gly Asp Ser Ile Ser Phe Ala Asp Leu Asn
                165                 170                 175

His Ile Pro Phe Thr Phe Tyr Phe Met Thr Thr Pro Tyr Ala Lys Val
            180                 185                 190

Phe Asp Glu Tyr Pro Lys Val Lys Ala Trp Trp Glu Met Leu Met Ala
            195                 200                 205

Arg Pro Ala Val Gln Arg Val Cys Lys His Met Pro Thr Lys Phe Lys
    210                 215                 220

Leu Gly Ala Gln Tyr
225
```

<210> SEQ ID NO 19
<211> LENGTH: 669
<212> TYPE: DNA
<213> ORGANISM: Triticum aestivum

<400> SEQUENCE: 19

-continued

```
atggcgggcg agaagggtct ggtgctgctg aacttctggg tgagcccgtt cgggcagcgc       60
tgcctcatcg ctcttgcaga aaaaggcctc ccctacgagt acgtcgaaga gaacctcatg      120
gccggcaaga gcgaccgcct cctccgctcc aaccccatcc acaagaagat cccagtgctc      180
ctccacgacg gccgccccgt caacgagtct ctcatcatcc tcaactacct cgacgacgcc      240
ttcccggaca ccccgtccct cctcccctcc gacccctacg agcgctcgca ggctcgcttc      300
tgggccgact acgtcgacaa gaaggtctac gactgcggca cccggctctg gaagctcaag      360
ggcgagccgc acgcgcaggc gcgggccgag atggtggaaa tcctcaagaa tctggacggg      420
gcgctcgggg ataagtcctt cttcggcggc gatgccttcg ggttcgtcga cgccgcgttc      480
gcgcccttca cgtcgtggtt ccacagctac gagaagtacg gcgagttcag cgtggcggag      540
gtggcgccga gatcgcggc gtgggcaaag cggtgcggcg agcgggagag cgtcgccaag      600
agcctctact cgcctgacaa gatttacgag ttcatcggcg tgctcaagaa gatgcacggc      660
gtcgagtaa                                                             669
```

<210> SEQ ID NO 20
<211> LENGTH: 222
<212> TYPE: PRT
<213> ORGANISM: Triticum aestivum

<400> SEQUENCE: 20

```
Met Ala Gly Glu Lys Gly Leu Val Leu Leu Asn Phe Trp Val Ser Pro
1               5                   10                  15

Phe Gly Gln Arg Cys Leu Ile Ala Leu Ala Glu Lys Gly Leu Pro Tyr
                20                  25                  30

Glu Tyr Val Glu Glu Asn Leu Met Ala Gly Lys Ser Asp Arg Leu Leu
            35                  40                  45

Arg Ser Asn Pro Ile His Lys Lys Ile Pro Val Leu Leu His Asp Gly
        50                  55                  60

Arg Pro Val Asn Glu Ser Leu Ile Ile Leu Asn Tyr Leu Asp Asp Ala
65                  70                  75                  80

Phe Pro Asp Thr Pro Ser Leu Leu Pro Ser Asp Pro Tyr Glu Arg Ser
                85                  90                  95

Gln Ala Arg Phe Trp Ala Asp Tyr Val Asp Lys Lys Val Tyr Asp Cys
                100                 105                 110

Gly Thr Arg Leu Trp Lys Leu Lys Gly Glu Pro His Ala Gln Ala Arg
            115                 120                 125

Ala Glu Met Val Glu Ile Leu Lys Asn Leu Asp Gly Ala Leu Gly Asp
            130                 135                 140

Lys Ser Phe Phe Gly Gly Asp Ala Phe Gly Phe Val Asp Ala Ala Phe
145                 150                 155                 160

Ala Pro Phe Thr Ser Trp Phe His Ser Tyr Glu Lys Tyr Gly Glu Phe
                165                 170                 175

Ser Val Ala Glu Val Ala Pro Lys Ile Ala Ala Trp Ala Lys Arg Cys
            180                 185                 190

Gly Glu Arg Glu Ser Val Ala Lys Ser Leu Tyr Ser Pro Asp Lys Ile
            195                 200                 205

Tyr Glu Phe Ile Gly Val Leu Lys Lys Met His Gly Val Glu
        210                 215                 220
```

<210> SEQ ID NO 21
<211> LENGTH: 654
<212> TYPE: DNA
<213> ORGANISM: Triticum aestivum

<400> SEQUENCE: 21

```
atggggacgg aggcgaaagt gaaggtgttc gggccggcga gatccacctg cgtggcgcgg      60
gtgctggtgt gcctggaaga ggtcggcgcc gagtacgagc tggtgcacgt ccacctcccc     120
gccggcgagc acaagggccc cgcgcatctc gcccgcaccc tctttggcca ggtcccggct     180
ttccaggacg gtgatctcat ccttttcgag tcgcgcgcga tttcgaggta cgtgctccgc     240
aaaggcgcat ccgatctact ccgagaaaac agcctcgccg agtcggcgac ggtggacgcg     300
tggctcgaag ctgagtccca caacttcgac agggccatgt cggcgatcac cttccagtgc     360
ttcgtcgtgc ccatgttcat gggcgggacg actgaccaca aaatcgtcga ggagaacctg     420
gagaagctta aggcggccct cggagtctac gaggagcgtc tgaccaggtt caaatacttg     480
gccggagatt tcatcagcct ggcggacctg agccattgcc ccatggctca ctacctgctg     540
gccagcccct gcgcgtcggt gctcgatgcg tatccgcgtg tgaaggactg ggttgatggg     600
atgatggatc gaccgagcgt gaaaaaggtc atggagctta tggatgcgtc atga          654
```

<210> SEQ ID NO 22
<211> LENGTH: 229
<212> TYPE: PRT
<213> ORGANISM: Triticum aestivum

<400> SEQUENCE: 22

```
Met Ser Pro Val Lys Val Phe Gly His Pro Met Leu Thr Asn Val Ala
1               5                   10                  15

Arg Val Leu Leu Phe Leu Glu Glu Val Gly Ala Glu Tyr Glu Leu Val
            20                  25                  30

Pro Leu Asp Phe Val Ala Gly Glu His Lys Arg Pro Gln His Val Gln
        35                  40                  45

Leu Asn Pro Phe Ala Lys Met Pro Gly Phe Gln Asp Gly Asp Leu Val
    50                  55                  60

Leu Phe Glu Ser Arg Ala Ile Ala Lys Tyr Ile Leu Arg Lys Tyr Gly
65                  70                  75                  80

Gly Thr Ala Gly Leu Asp Leu Leu Gly Glu Asn Ser Gly Ile Glu Glu
                85                  90                  95

Leu Ala Met Val Asp Met Trp Thr Glu Val Glu Ala Gln Gln Tyr Tyr
            100                 105                 110

Pro Ala Ile Ser Pro Val Val Phe Glu Cys Ile Ile Ile Pro Phe Ile
        115                 120                 125

Ile Pro Gly Gly Gly Ala Ala Pro Asn Arg Ser Val Val Asp Glu Ser
    130                 135                 140

Leu Glu Arg Leu Arg Gly Val Leu Gly Ile Tyr Glu Ala Arg Leu Glu
145                 150                 155                 160

Lys Ser Ser Tyr Leu Ala Gly Asp Ser Ile Ser Phe Ala Asp Leu Asn
                165                 170                 175

His Ile Pro Phe Thr Phe Tyr Phe Met Thr Thr Pro Tyr Ala Lys Val
            180                 185                 190

Phe Asp Glu Tyr Pro Lys Val Lys Ala Trp Trp Glu Met Leu Met Ala
        195                 200                 205

Arg Pro Ala Val Gln Arg Val Cys Lys His Met Pro Thr Lys Phe Lys
    210                 215                 220

Leu Gly Ala Gln Tyr
225
```

<210> SEQ ID NO 23
<211> LENGTH: 795
<212> TYPE: DNA
<213> ORGANISM: Triticum aestivum

<400> SEQUENCE: 23
atgacgcatc gatcttttat atattccgca ctccacacta accacagaat cccacggaac        60
cttcaggcac acccacggca gaaaatggcc aacggaggag acgagctgaa gctgctgggc       120
atgtgggcga gcccatacgt ggtcagggtg cagctcgcgc tccacctcaa gggcgtgagc       180
tacgagtacg tcgaggagga cctcgccagc aagagcgagc tcttcctccg ctccaacccg       240
gtgcacaaga cagtcccgat cctcatccac aacggcaagc ccgtctgcga gtcccaggtc       300
atcctccagt acatcgacga ggccttcgcc ggcgtcggcc cgcccctcct ccccgctgac       360
ccctacgagc gcgccgtcgc gcgattctgg gccgcctacg tcgaggacaa gctgctggcg       420
ccgtggggga aggtgttcag ggtgaagacc gacgaggaga gggccgagtg gacgaggcag       480
acggcggcgg cgctgggtcc tctggaggat ggcctcaggg agtgctccaa ggggaagggc       540
ttcttcggcg gcgactgcgt cgggtacgtt gacgtcctgc tcggcagcat ggtgccgtgg       600
gtgcgcgcca ccgagaggct ctccggcgac aagttaatag acgccggcaa ggcccccgctg      660 ctggcggcat ggatggagcg cattagcgag ctcgacgccg ccaaggcggt cttccaggac       720
gtcgacaggt ggttgagta cgccgggca atacaggccc ggctttccgc cgcggctgct       780
gcaagcaccc aataa                                                        795

<210> SEQ ID NO 24
<211> LENGTH: 264
<212> TYPE: PRT
<213> ORGANISM: Triticum aestivum

<400> SEQUENCE: 24

Met Thr His Arg Ser Phe Ile Tyr Ser Ala Leu His Thr Asn His Arg
1               5                   10                  15

Ile Pro Arg Asn Leu Gln Ala His Pro Arg Gln Lys Met Ala Asn Gly
                20                  25                  30

Gly Asp Glu Leu Lys Leu Leu Gly Met Trp Ala Ser Pro Tyr Val Val
            35                  40                  45

Arg Val Gln Leu Ala Leu His Leu Lys Gly Val Ser Tyr Glu Tyr Val
        50                  55                  60

Glu Glu Asp Leu Ala Ser Lys Ser Glu Leu Phe Leu Arg Ser Asn Pro
65                  70                  75                  80

Val His Lys Thr Val Pro Ile Leu Ile His Asn Gly Lys Pro Val Cys
                85                  90                  95

Glu Ser Gln Val Ile Leu Gln Tyr Ile Asp Glu Ala Phe Ala Gly Val
                100                 105                 110

Gly Pro Pro Leu Leu Pro Ala Asp Pro Tyr Glu Arg Ala Val Ala Arg
            115                 120                 125

Phe Trp Ala Ala Tyr Val Glu Asp Lys Leu Leu Ala Pro Trp Gly Lys
        130                 135                 140

Val Phe Arg Val Lys Thr Asp Glu Glu Arg Ala Glu Trp Thr Arg Gln
145                 150                 155                 160

Thr Ala Ala Ala Leu Gly Pro Leu Glu Asp Gly Leu Arg Glu Cys Ser
                165                 170                 175

Lys Gly Lys Gly Phe Phe Gly Gly Asp Cys Val Gly Tyr Val Asp Val
                180                 185                 190

-continued

```
Leu Leu Gly Ser Met Val Pro Trp Val Arg Ala Thr Glu Arg Leu Ser
        195             200             205

Gly Asp Lys Leu Ile Asp Ala Gly Lys Ala Pro Leu Leu Ala Ala Trp
        210             215             220

Met Glu Arg Ile Ser Glu Leu Asp Ala Ala Lys Ala Val Phe Gln Asp
225             230             235             240

Val Asp Arg Val Val Glu Tyr Ala Gly Ala Ile Gln Ala Arg Leu Ser
            245             250             255

Ala Ala Ala Ala Ala Ser Thr Gln
            260

<210> SEQ ID NO 25
<211> LENGTH: 714
<212> TYPE: DNA
<213> ORGANISM: Triticum aestivum

<400> SEQUENCE: 25
atgtcgtcgg ggaagcagga gacggcggcg gtgcgcgtgc tgggcaggtg gccgagcccg        60
ttcgtgatcc gggtgctgat agctcttggg ctcaagggcg tggaccacga gctcgtggag       120
gaggcggcgg gcaacaagag cgagctgctg ctcgcctcca accccgtgca caagaagatc       180
cccgtgctcc tgcaccacgg caggcccgtc tccgagtccc tcatcatcgt ccagtacgtc       240
gacgaggcct gggcctccca agcccggcg ctcatcccgt ccgacccta cgccgcgcg        300 gccgagcggt tctgggccca gtacgtcgac gacaagtttc ctacggcgat ccgggtcctg       360
aggggaaggc tggacggaga caaggaagaa gcggcggctc aggtgtgcgc cgctctgcag       420
cacctggagg tggccttcgt cgagtgcggc caagggaagg attacttcgg cggcgacggc       480
gtcggttacc tggacattgc tctcgggtcg cacctcggat gggtcagggc ggtagagagg       540
atcgctgaaa tcaggctgct cgacgcggcc aaggttccta agctggcggc gtgggcggat       600
cggttctgcg cccacccggc ggtggcgaac gccatgccta acgtggacag gttcgtggag       660
ttcagcgtca agaatgacgg cgttctgaag gcggctagtg ctaattccaa gtga            714

<210> SEQ ID NO 26
<211> LENGTH: 237
<212> TYPE: PRT
<213> ORGANISM: Triticum aestivum

<400> SEQUENCE: 26

Met Ser Ser Gly Lys Gln Glu Thr Ala Ala Val Arg Val Leu Gly Arg
1               5               10              15

Trp Pro Ser Pro Phe Val Ile Arg Val Leu Ile Ala Leu Gly Leu Lys
            20              25              30

Gly Val Asp His Glu Leu Val Glu Glu Ala Ala Gly Asn Lys Ser Glu
        35              40              45

Leu Leu Leu Ala Ser Asn Pro Val His Lys Lys Ile Pro Val Leu Leu
    50              55              60

His His Gly Arg Pro Val Ser Glu Ser Leu Ile Ile Val Gln Tyr Val
65              70              75              80

Asp Glu Ala Trp Ala Ser Gln Ala Pro Ala Leu Ile Pro Ser Asp Pro
            85              90              95

Tyr Ala Arg Ala Ala Glu Arg Phe Trp Ala Gln Tyr Val Asp Asp Lys
            100             105             110

Phe Pro Thr Ala Ile Arg Val Leu Arg Gly Arg Leu Asp Gly Asp Lys
        115             120             125
```

-continued

```
Glu Glu Ala Ala Ala Gln Val Cys Ala Ala Leu Gln His Leu Glu Val
    130                 135                 140

Ala Phe Val Glu Cys Gly Gln Gly Lys Asp Tyr Phe Gly Gly Asp Gly
145                 150                 155                 160

Val Gly Tyr Leu Asp Ile Ala Leu Gly Ser His Leu Gly Trp Val Arg
                165                 170                 175

Ala Val Glu Arg Ile Ala Glu Ile Arg Leu Leu Asp Ala Ala Lys Val
            180                 185                 190

Pro Lys Leu Ala Ala Trp Ala Asp Arg Phe Cys Ala His Pro Ala Val
        195                 200                 205

Ala Asn Ala Met Pro Asn Val Asp Arg Phe Val Glu Phe Ser Val Lys
    210                 215                 220

Asn Asp Gly Val Leu Lys Ala Ala Ser Ala Asn Ser Lys
225                 230                 235
```

```
<210> SEQ ID NO 27
<211> LENGTH: 693
<212> TYPE: DNA
<213> ORGANISM: Triticum aestivum

<400> SEQUENCE: 27
atggccggag cagcaaacga tctgaagcta ctgggcatgt gggcgagccc gtacgtcctg      60
cgggtgcgcc ttgctctcag catcaagagc atcagctacg agtacgcaga ggaggacctc     120
cggcacaaga gcgagctgct cctgcggtca aaccccgtcc acaacaaggt ccccgtgctg     180
atccacgccg gcaagcccgt ctgcgagtcg ctggtcatcc tacagtacat cgacgacgct     240
ttcggcggtg ccggccccgc cctcctcccg gccgatcccc acgagcgcgc cgtcgcccgg     300
ttctgggccg ccttcatcga ggacacgctc gtgaaggcga tgaaccaggc gtcatggagc     360
aagacggagg cggagaaggt ggaggggaac aaacgggcga ctgctgcgtt gaacaccctg     420
gaggcggccc tgaggggatgt ctccaagggg aagcccttct cggggggcga cagcaccggg     480
tatgtggaca tcgtgctcgg cggcctcctc gcggggggtgc gcgccatgga ggcgatgccg     540
ggcgtcaagg ccttcgaccc cgtcacgatg ccgctcctgg ccgcgtgggc ggaccacttc     600
ggcgcgctgg acgcggtggc ggccgtgatg ccggacgtga gcaagctcgt ggagctcttc     660
atcacgatgc acgctgctgt tgcggcaaac taa                                  693
```

```
<210> SEQ ID NO 28
<211> LENGTH: 230
<212> TYPE: PRT
<213> ORGANISM: Triticum aestivum

<400> SEQUENCE: 28

Met Ala Gly Ala Ala Asn Asp Leu Lys Leu Leu Gly Met Trp Ala Ser
1               5                   10                  15

Pro Tyr Val Leu Arg Val Arg Leu Ala Leu Ser Ile Lys Ser Ile Ser
                20                  25                  30

Tyr Glu Tyr Ala Glu Glu Asp Leu Arg His Lys Ser Glu Leu Leu Leu
            35                  40                  45

Arg Ser Asn Pro Val His Asn Lys Val Pro Val Leu Ile His Ala Gly
        50                  55                  60

Lys Pro Val Cys Glu Ser Leu Val Ile Leu Gln Tyr Ile Asp Asp Ala
65                  70                  75                  80

Phe Gly Gly Ala Gly Pro Ala Leu Leu Pro Ala Asp Pro His Glu Arg
                85                  90                  95
```

```
Ala Val Ala Arg Phe Trp Ala Ala Phe Ile Glu Asp Thr Leu Val Lys
            100                 105                 110

Ala Met Asn Gln Ala Ser Trp Ser Lys Thr Glu Ala Glu Lys Val Glu
            115                 120                 125

Gly Asn Lys Arg Ala Thr Ala Ala Leu Asn Thr Leu Glu Ala Ala Leu
        130                 135                 140

Arg Asp Val Ser Lys Gly Lys Pro Phe Phe Gly Gly Asp Ser Thr Gly
145                 150                 155                 160

Tyr Val Asp Ile Val Leu Gly Gly Leu Leu Ala Gly Val Arg Ala Met
                165                 170                 175

Glu Ala Met Pro Gly Val Lys Ala Phe Asp Pro Val Thr Met Pro Leu
            180                 185                 190

Leu Ala Ala Trp Ala Asp His Phe Gly Ala Leu Asp Ala Val Ala Ala
            195                 200                 205

Val Met Pro Asp Val Ser Lys Leu Val Glu Leu Phe Ile Thr Met His
        210                 215                 220

Ala Ala Val Ala Ala Asn
225                 230
```

<210> SEQ ID NO 29
<211> LENGTH: 810
<212> TYPE: DNA
<213> ORGANISM: Triticum aestivum

<400> SEQUENCE: 29

```
atgacgcacg gaggtataca aacaaatgtg aagaatacgg tgtctatcag tgttgcactg     60
atagagcagg ggagaaaaaa aaagacggcg aacgaaacaa tggcagccga aggaggtctg    120
aagctgctcg gcttgacggt gagcccgttc gtgatccgtg tacgcatggc gctgcagatg    180
aaaggcgtcg gctacgagta cgtggagcag gacctgttca ccaagggcga gctcctccgc    240
aagtccaacc cggtgcacat gaaggtcccg gtgctcatcc acgacggcag acccgtctgc    300
gagtcgctgg ccatcgtgca gtacgtcgac gaggcctggg cggccgcggg ccctcgatc    360 ctccccgccg accctacga ccgcgccgcc gctcgcttct gggccgccta cgccgacagc    420
aagctcttgc cggcgtgggt aggcatcatg tgggcggaga cggaggagga gagggcggag    480
aaggtcggcg acacgctcgc ggctatcggc cagttggagg aggcgttcgg gacgtgctcg    540
aacggtaagg ccttcttcgc cggcgactcc gtcgggtacc tagatctcgt cgtcggctcg    600
cagttgctct ggttcgaggt gctgcggaag atgttcggcg tcgtggtcgt tgaggtcggc    660
agggctctgc tcttggccgc gtgggtggag cggtttgggg agactgatac ggccaaggag    720
gtggtgccgg acgttgacac ggcggtggag tacctcaaga agcttcagtc tcgccgggct    780
ggttccacgg ttgcccagct gctgtcgtga                                    810
```

<210> SEQ ID NO 30
<211> LENGTH: 269
<212> TYPE: PRT
<213> ORGANISM: Triticum aestivum

<400> SEQUENCE: 30

```
Met Thr His Gly Gly Ile Gln Thr Asn Val Lys Asn Thr Val Ser Ile
1               5                   10                  15

Ser Val Ala Leu Ile Glu Gln Gly Arg Lys Lys Lys Thr Ala Asn Glu
            20                  25                  30

Thr Met Ala Ala Glu Gly Gly Leu Lys Leu Leu Gly Leu Thr Val Ser
        35                  40                  45
```

```
Pro Phe Val Ile Arg Val Arg Met Ala Leu Gln Met Lys Gly Val Gly
    50              55              60

Tyr Glu Tyr Val Glu Gln Asp Leu Phe Thr Lys Gly Glu Leu Leu Arg
65              70              75              80

Lys Ser Asn Pro Val His Met Lys Val Pro Val Leu Ile His Asp Gly
            85              90              95

Arg Pro Val Cys Glu Ser Leu Ala Ile Val Gln Tyr Val Asp Glu Ala
            100             105             110

Trp Ala Ala Ala Gly Pro Ser Ile Leu Pro Ala Asp Pro Tyr Asp Arg
            115             120             125

Ala Ala Ala Arg Phe Trp Ala Ala Tyr Ala Asp Ser Lys Leu Leu Pro
    130             135             140

Ala Trp Val Gly Ile Met Trp Ala Glu Thr Glu Glu Glu Arg Ala Glu
145             150             155             160

Lys Val Gly Asp Thr Leu Ala Ala Ile Gly Gln Leu Glu Glu Ala Phe
            165             170             175

Gly Thr Cys Ser Asn Gly Lys Ala Phe Phe Ala Gly Asp Ser Val Gly
            180             185             190

Tyr Leu Asp Leu Val Val Gly Ser Gln Leu Leu Trp Phe Glu Val Leu
        195             200             205

Arg Lys Met Phe Gly Val Val Val Val Glu Val Gly Arg Ala Leu Leu
    210             215             220

Leu Ala Ala Trp Val Glu Arg Phe Gly Glu Thr Asp Thr Ala Lys Glu
225             230             235             240

Val Val Pro Asp Val Asp Thr Ala Val Glu Tyr Leu Lys Lys Leu Gln
            245             250             255

Ser Arg Arg Ala Gly Ser Thr Val Ala Gln Leu Leu Ser
        260             265
```

<210> SEQ ID NO 31
<211> LENGTH: 717
<212> TYPE: DNA
<213> ORGANISM: Hordeum vulgare

<400> SEQUENCE: 31

```
atgtcgcagc agccagaaca ggcgccggtg aggctcatca cggcgttcgg cagcccgttc        60
gcgcaccggg tggaggtggc gctcacgctc aaggggggtgc cgtacgagct gctcgtggag       120
gacctggcca gcaagagcga cctgctgctc gcccacaacc ccgtctacca gtcggtcccc       180
gtcctcctcc acggcgaccg cgccgtctgc gactccctcg tcatcgtcga gtacgtcgac       240
gaggccttcc acgacgacga cgggacggcg ccccggcgcc tcctcccggc ggacccctac       300
gaccgcgcca ccgccgcgtt ctgggccgac ttcgtcgcca caagtgctt gaagccgctg       360 tggcagtcga cgtggaccga cggcgaggag caggcgcggc tggcgaggga gaccaaggag       420
ggactggggg tactggaggc acagctcgac gggaagcggt tctttggggg cgaggccctc       480
ggcttcgtcg acctcgccgc ctgcacgctg gctcactggc tcggcgtgct gggggaagtc       540
ggcggggtgc ggctgatgga ggacggcgag taccctgctc tccgccggtg ggccaaggag       600
tacacttccc atgaggtcgt caggcggtcc ctgccgaca gggacgagct cgtcgcctac       660
ttcaccaaaa acaaggagaa gtaccggtcg tcgatgctca gccagcggt gaagtga       717
```

<210> SEQ ID NO 32
<211> LENGTH: 238
<212> TYPE: PRT

-continued

<213> ORGANISM: Hordeum vulgare

<400> SEQUENCE: 32

Met Ser Gln Gln Pro Glu Gln Ala Pro Val Arg Leu Ile Thr Ala Phe
1               5                   10                  15

Gly Ser Pro Phe Ala His Arg Val Glu Val Ala Leu Thr Leu Lys Gly
            20                  25                  30

Val Pro Tyr Glu Leu Leu Val Glu Asp Leu Ala Ser Lys Ser Asp Leu
        35                  40                  45

Leu Leu Ala His Asn Pro Val Tyr Gln Ser Val Pro Val Leu Leu His
    50                  55                  60

Gly Asp Arg Ala Val Cys Asp Ser Leu Val Ile Val Glu Tyr Val Asp
65                  70                  75                  80

Glu Ala Phe His Asp Asp Asp Gly Thr Ala Pro Arg Arg Leu Leu Pro
                85                  90                  95

Ala Asp Pro Tyr Asp Arg Ala Thr Ala Arg Phe Trp Ala Asp Phe Val
            100                 105                 110

Ala Asn Lys Cys Leu Lys Pro Leu Trp Gln Ser Thr Trp Thr Asp Gly
        115                 120                 125

Glu Glu Gln Ala Arg Leu Ala Arg Glu Thr Lys Glu Gly Leu Gly Val
    130                 135                 140

Leu Glu Ala Gln Leu Asp Gly Lys Arg Phe Phe Gly Gly Glu Ala Leu
145                 150                 155                 160

Gly Phe Val Asp Leu Ala Ala Cys Thr Leu Ala His Trp Leu Gly Val
            165                 170                 175

Leu Gly Glu Val Gly Gly Val Arg Leu Met Glu Asp Gly Glu Tyr Pro
            180                 185                 190

Ala Leu Arg Arg Trp Ala Lys Glu Tyr Thr Ser His Glu Val Val Arg
        195                 200                 205

Arg Ser Leu Pro Asp Arg Asp Glu Leu Val Ala Tyr Phe Thr Lys Asn
    210                 215                 220

Lys Glu Lys Tyr Arg Ser Ser Met Leu Lys Pro Ala Val Lys
225                 230                 235

<210> SEQ ID NO 33
<211> LENGTH: 690
<212> TYPE: DNA
<213> ORGANISM: Hordeum vulgare

<400> SEQUENCE: 33
atggatcatc aagaggagaa ggtgaagctt tttggcatgt gggcgagccc ctacgtcctc      60
aaggtgaaat gggcgctgag catcaagggc gtggagtacg agtacctgga ggaggacctg     120
aggaacaaga gcgacgatct cctgaacac aaccccgtgc acaagaaggt ccccgtgctg     180
ctctaccacg gcaagccggt ggcagagtcc gacgtcatcg tcgagttcgt cgacgaggcg     240
tggagccacc gaggcggccg catcctcccc ggcgacccct acgagcgcgc catggctcgt     300
ttctgggtga ggtttgtgca cgacaagctc tcgccgccga tttggaagtg gttcacgacg     360
gcgccaggcg aggaccagga ggccgcgcgg ggggcctccg ttgagcagct gcaggtcctg     420
gaggagttgc tcgccgtcgg cgggaaggag ttcttcgccg gggagagcgt tgggctcgtg     480
gacctgtcgc tcggcgcgat ggcgtacgtg gtcccgatgt acgaggagat cgtcggcgtg     540
aggctggtca ccgaggagag gtttccgtct ctgtcggcgt ggatgggcg gttcttgggc     600 tcgccgccgg tgaaggatca cccgccgcca gtggagaggc tgataccag gtaccgagcc     660

-continued

```
atgcgcgaag cctttctgaa gatgggctag                                      690

<210> SEQ ID NO 34
<211> LENGTH: 229
<212> TYPE: PRT
<213> ORGANISM: Hordeum vulgare

<400> SEQUENCE: 34

Met Asp His Gln Glu Glu Lys Val Lys Leu Phe Gly Met Trp Ala Ser
1               5                   10                  15

Pro Tyr Val Leu Lys Val Lys Trp Ala Leu Ser Ile Lys Gly Val Glu
                20                  25                  30

Tyr Glu Tyr Leu Glu Glu Asp Leu Arg Asn Lys Ser Asp Asp Leu Leu
            35                  40                  45

Glu His Asn Pro Val His Lys Lys Val Pro Val Leu Leu Tyr His Gly
        50                  55                  60

Lys Pro Val Ala Glu Ser Asp Val Ile Val Glu Phe Val Asp Glu Ala
65                  70                  75                  80

Trp Ser His Arg Gly Gly Arg Ile Leu Pro Gly Asp Pro Tyr Glu Arg
                85                  90                  95

Ala Met Ala Arg Phe Trp Val Arg Phe Val His Asp Lys Leu Ser Pro
            100                 105                 110

Pro Ile Trp Lys Trp Phe Thr Thr Ala Pro Gly Glu Asp Gln Glu Ala
            115                 120                 125

Ala Arg Gly Ala Ser Val Glu Gln Leu Gln Val Leu Glu Glu Leu Leu
        130                 135                 140

Ala Val Gly Gly Lys Glu Phe Phe Ala Gly Glu Ser Val Gly Leu Val
145                 150                 155                 160

Asp Leu Ser Leu Gly Ala Met Ala Tyr Val Val Pro Met Tyr Glu Glu
                165                 170                 175

Ile Val Gly Val Arg Leu Val Thr Glu Glu Arg Phe Pro Ser Leu Ser
            180                 185                 190

Ala Trp Met Gly Arg Phe Leu Gly Ser Pro Pro Val Lys Asp His Pro
        195                 200                 205

Pro Pro Val Glu Arg Leu Ile Pro Arg Tyr Arg Ala Met Arg Glu Ala
        210                 215                 220

Phe Leu Lys Met Gly
225

<210> SEQ ID NO 35
<211> LENGTH: 645
<212> TYPE: DNA
<213> ORGANISM: Hordeum vulgare

<400> SEQUENCE: 35
atggcactgc agatgaaacg cgtgggctac gagtacatgg agcaggacct gttcaccaag     60
ggcgagctcc tcctcaagtc caacccggtg cacatgaagg tcccggtgct catccacgac     120
ggcaaatcca tctgcgagtc gctggccatc gtgcagtacg tcgacgaggt ctgggccgcc     180
acgggcacct ccatcctccc cgccgacccc tacgaccgcg ccgccgctcg cttctgggcc     240
gcctacgccg acagcaagct cttgcctgcg tgggtgggca tcatgtgggc ggcgacggag     300
gaggagagag cggagaaggt cggcgacacg ctcgcggcta tcggccaact ggaggaggcg     360
ttcggaaagt gctccaacgg aaagcccttc ttcgccggcg attccgtcgg ctacctcgat     420
ctcgtcgtcg gttcgcagtt gctctggttc gaggtgctgc ggaagatgtt cggcgtcgtg     480
```

-continued

```
gtcattgagg cctgcagggc tcccttcttg gccgcgtggg tgaagcggtt ttgggagact       540
gatacggcga aggcggtggt gccggacgtt ggcacggcgg cggagtacct gaagaagctt       600
cagtctcatc gggctggtgc cacggttgcc cagttgctgt cgtga                       645

<210> SEQ ID NO 36
<211> LENGTH: 214
<212> TYPE: PRT
<213> ORGANISM: Hordeum vulgare

<400> SEQUENCE: 36

Met Ala Leu Gln Met Lys Arg Val Gly Tyr Glu Tyr Met Glu Gln Asp
1               5                   10                  15

Leu Phe Thr Lys Gly Glu Leu Leu Leu Lys Ser Asn Pro Val His Met
                20                  25                  30

Lys Val Pro Val Leu Ile His Asp Gly Lys Ser Ile Cys Glu Ser Leu
            35                  40                  45

Ala Ile Val Gln Tyr Val Asp Glu Val Trp Ala Ala Thr Gly Thr Ser
        50                  55                  60

Ile Leu Pro Ala Asp Pro Tyr Asp Arg Ala Ala Ala Arg Phe Trp Ala
65                  70                  75                  80

Ala Tyr Ala Asp Ser Lys Leu Leu Pro Ala Trp Val Gly Ile Met Trp
                85                  90                  95

Ala Ala Thr Glu Glu Glu Arg Ala Glu Lys Val Gly Asp Thr Leu Ala
                100                 105                 110

Ala Ile Gly Gln Leu Glu Glu Ala Phe Gly Lys Cys Ser Asn Gly Lys
            115                 120                 125

Pro Phe Phe Ala Gly Asp Ser Val Gly Tyr Leu Asp Leu Val Val Gly
        130                 135                 140

Ser Gln Leu Leu Trp Phe Glu Val Leu Arg Lys Met Phe Gly Val Val
145                 150                 155                 160

Val Ile Glu Ala Cys Arg Ala Pro Phe Leu Ala Ala Trp Val Lys Arg
                165                 170                 175

Phe Trp Glu Thr Asp Thr Ala Lys Ala Val Val Pro Asp Val Gly Thr
                180                 185                 190

Ala Ala Glu Tyr Leu Lys Lys Leu Gln Ser His Arg Ala Gly Ala Thr
            195                 200                 205

Val Ala Gln Leu Leu Ser
        210

<210> SEQ ID NO 37
<211> LENGTH: 93
<212> TYPE: DNA
<213> ORGANISM: Hordeum vulgare

<400> SEQUENCE: 37
gaggctgcaa agaaggcggc gccacccatg gaaagcatgt tggaggaggc cgagaagctg        60
cgggctatgt gggctgcggc ggctgccaag taa                                    93

<210> SEQ ID NO 38
<211> LENGTH: 232
<212> TYPE: PRT
<213> ORGANISM: Hordeum vulgare

<400> SEQUENCE: 38

Met Ala Ser Glu Gly Asp Asp Val Lys Val Leu Gly Thr Ala Ala Ser
1               5                   10                  15
```

-continued

```
Met Phe Ala Ile Arg Val Arg Met Ala Leu His Ala Lys Gly Val Ser
        20              25                  30

Tyr Glu Tyr Leu Glu Gln Asp Leu Phe His Lys Gly Glu Leu Leu Leu
        35              40                  45

Ala Ser Asn Pro Val Arg Lys Ala Val Pro Val Leu Ile His Ala Gly
    50              55                  60

Arg Pro Val Cys Glu Ser Leu Ala Ile Val Glu Tyr Ile Asp Glu Val
65                  70                  75                  80

Trp Ala Gly Ala Ala Ser Leu Leu Pro Ala Asp Pro Tyr Asp Arg Ala
                85                  90                  95

Val Ala Arg Phe Trp Ala Ala Tyr Val Asp Asp Lys Ala Val Pro Thr
            100                 105                 110

Trp Ile Gly Ile Met Arg Ala Ala Thr Glu Glu Asp Arg Ala Glu Arg
            115                 120                 125

Leu Ala Ala Ala Leu Ala Ala Val Ala Pro Leu Glu Asp Ala Phe Ala
        130                 135                 140

Gln Cys Ser Gly Gly Lys Ala Phe Phe Ala Gly Asp Ser Ile Gly Tyr
145                 150                 155                 160

Val Asp Leu Ala Leu Gly Cys Asn Leu Phe Trp Ile Glu Ala Leu Arg
                165                 170                 175

His Met Phe Gly Ile Thr Val Ile Asp Ala Gly Arg Thr Pro Arg Leu
            180                 185                 190

Ala Ala Trp Ala Glu Arg Phe Val Glu Thr Glu Ala Ala Lys Lys Ala
            195                 200                 205

Ala Pro Pro Met Glu Ser Met Leu Glu Glu Ala Glu Lys Leu Arg Ala
        210                 215                 220

Met Trp Ala Ala Ala Ala Ala Lys
225                 230
```

```
<210> SEQ ID NO 39
<211> LENGTH: 708
<212> TYPE: DNA
<213> ORGANISM: Hordeum vulgare

<400> SEQUENCE: 39
atggcaggag gcggcgaggg cgagctgaag ctgctgggcg tgtggacgag cccgttcgtc      60
atccgggtgc gcgtggtgct caacctcaag tcgctgccgt acgagtacgt ggaggagaac     120
ctgggcagca agagcgcgct cctcctgggc tccaacccgg tgcaccagag cgtgccggtc     180
ctcctccacg gcggccgccc cgtgaacgag tcccaggtca tcgtgcagta catcgacgag     240
gtctgggcgg gggtcggccc gtcggtgctc ccggccgacc cctacgagcg cgccgtggcg     300
cgcttctggg cggcgtacgt cgacgacaag gtcgggtcgg cgtggacggg gatgctcttc     360
tcgtgcaaga cggaggagga gagggcggag ccgtgtccc gcgccgtggc ggcgctggag      420
accctggagg cgcgctcgc ggagtgctcc gggggaagc cgttcttcgg cggcgacgcc       480
atcgggttcg tcgacgtcgt gctcggcggc tacctcgggt ggttcggggc gatcgacaag     540
atcatcgggc gccggctgat cgacccggcg aggacgccgc tgctggccag gtgggaggag     600
tggttccgcg cggcggacgc ggccaagggc gtcgtgccgg acgacgccga caagatgctc     660
gacttcttgc ccaccctgct cgcttggatc gcctccaagg ccaagtga                 708
```

```
<210> SEQ ID NO 40
<211> LENGTH: 235
<212> TYPE: PRT
<213> ORGANISM: Hordeum vulgare
```

<400> SEQUENCE: 40

```
Met Ala Gly Gly Gly Glu Gly Glu Leu Lys Leu Leu Gly Val Trp Thr
1               5                   10                  15

Ser Pro Phe Val Ile Arg Val Arg Val Val Leu Asn Leu Lys Ser Leu
            20                  25                  30

Pro Tyr Glu Tyr Val Glu Glu Asn Leu Gly Ser Lys Ser Ala Leu Leu
        35                  40                  45

Leu Gly Ser Asn Pro Val His Gln Ser Val Pro Val Leu Leu His Gly
        50                  55                  60

Gly Arg Pro Val Asn Glu Ser Gln Val Ile Val Gln Tyr Ile Asp Glu
65                  70                  75                  80

Val Trp Ala Gly Val Gly Pro Ser Val Leu Pro Ala Asp Pro Tyr Glu
                85                  90                  95

Arg Ala Val Ala Arg Phe Trp Ala Ala Tyr Val Asp Asp Lys Val Gly
            100                 105                 110

Ser Ala Trp Thr Gly Met Leu Phe Ser Cys Lys Thr Glu Glu Glu Arg
            115                 120                 125

Ala Glu Ala Val Ser Arg Ala Val Ala Ala Leu Glu Thr Leu Glu Gly
        130                 135                 140

Ala Leu Ala Glu Cys Ser Gly Gly Lys Pro Phe Phe Gly Gly Asp Ala
145                 150                 155                 160

Ile Gly Phe Val Asp Val Val Leu Gly Gly Tyr Leu Gly Trp Phe Gly
                165                 170                 175

Ala Ile Asp Lys Ile Ile Gly Arg Arg Leu Ile Asp Pro Ala Arg Thr
                180                 185                 190

Pro Leu Leu Ala Arg Trp Glu Glu Trp Phe Arg Ala Ala Asp Ala Ala
            195                 200                 205

Lys Gly Val Val Pro Asp Asp Ala Asp Lys Met Leu Asp Phe Leu Pro
        210                 215                 220

Thr Leu Leu Ala Trp Ile Ala Ser Lys Ala Lys
225                 230                 235
```

```
<210> SEQ ID NO 41
<211> LENGTH: 18
<212> TYPE: DNA
<213> ORGANISM: Artificial Sequence
<220> FEATURE:
<223> OTHER INFORMATION: Primer sequence

<400> SEQUENCE: 41
ccggacaaaa tggggtcg                                              18

<210> SEQ ID NO 42
<211> LENGTH: 21
<212> TYPE: DNA
<213> ORGANISM: Artificial Sequence
<220> FEATURE:
<223> OTHER INFORMATION: Primer sequence

<400> SEQUENCE: 42
ttattcaatg gaagtcacgt c                                          21

<210> SEQ ID NO 43
<211> LENGTH: 39
<212> TYPE: DNA
<213> ORGANISM: Artificial Sequence
<220> FEATURE:
<223> OTHER INFORMATION: Primer sequence
```

```
<400> SEQUENCE: 43
aatctctact tccaaggcca tatggccgga ggagatgac                    39

<210> SEQ ID NO 44
<211> LENGTH: 29
<212> TYPE: DNA
<213> ORGANISM: Artificial Sequence
<220> FEATURE:
<223> OTHER INFORMATION: Primer sequence

<400> SEQUENCE: 44
gggcgacgag cttatcgtca acgtaggcg                               29

<210> SEQ ID NO 45
<211> LENGTH: 28
<212> TYPE: DNA
<213> ORGANISM: Artificial Sequence
<220> FEATURE:
<223> OTHER INFORMATION: Primer sequence

<400> SEQUENCE: 45
tgacgataag ctcgtcgccc catgggta                               28

<210> SEQ ID NO 46
<211> LENGTH: 47
<212> TYPE: DNA
<213> ORGANISM: Artificial Sequence
<220> FEATURE:
<223> OTHER INFORMATION: Primer sequence

<400> SEQUENCE: 46
aagcttgtcg acggagctcg aattcttact tggtctctga agcagcg          47

<210> SEQ ID NO 47
<211> LENGTH: 23
<212> TYPE: DNA
<213> ORGANISM: Artificial Sequence
<220> FEATURE:
<223> OTHER INFORMATION: Primer sequence

<400> SEQUENCE: 47
ccttacacac acagatctag atg                                    23

<210> SEQ ID NO 48
<211> LENGTH: 23
<212> TYPE: DNA
<213> ORGANISM: Artificial Sequence
<220> FEATURE:
<223> OTHER INFORMATION: Primer sequence

<400> SEQUENCE: 48
caagaacaga aatacggatt tcc                                    23

<210> SEQ ID NO 49
<211> LENGTH: 30
<212> TYPE: DNA
<213> ORGANISM: Artificial Sequence
<220> FEATURE:
<223> OTHER INFORMATION: Primer sequence

<400> SEQUENCE: 49
gggtgacgag cttatcgtca atgtaggcgg                             30

<210> SEQ ID NO 50
```

-continued

```
<211> LENGTH: 28
<212> TYPE: DNA
<213> ORGANISM: Artificial Sequence
<220> FEATURE:
<223> OTHER INFORMATION: Primer sequence

<400> SEQUENCE: 50
tgacgataag ctcgtcaccc catgggta                                              28

<210> SEQ ID NO 51
<211> LENGTH: 45
<212> TYPE: DNA
<213> ORGANISM: Artificial Sequence
<220> FEATURE:
<223> OTHER INFORMATION: Primer sequence

<400> SEQUENCE: 51
aagcttgtcg acggagctcg aattctactt ggtctccgaa gcagc                          45
```